United States Patent
Hutter et al.

(10) Patent No.: US 12,270,784 B2
(45) Date of Patent: Apr. 8, 2025

(54) DETECTOR FOR DETECTING ANALYTES IN GAS PHASE COMPRISING POROUS DIELECTRIC OR SEMICONDUCTING SORBENT AND CORRESPONDING DETECTION METHOD

(71) Applicant: SENSORHUT LTD, Cambridge (GB)

(72) Inventors: Tanya Hutter, Cambridge (GB); William Thomas Winter, Cambridge (GB)

(73) Assignee: SENSORHUT LTD, Cambridge (GB)

( * ) Notice: Subject to any disclaimer, the term of this patent is extended or adjusted under 35 U.S.C. 154(b) by 0 days.

(21) Appl. No.: 18/538,368

(22) Filed: Dec. 13, 2023

(65) Prior Publication Data

US 2024/0230592 A1   Jul. 11, 2024

Related U.S. Application Data

(63) Continuation of application No. 17/608,667, filed as application No. PCT/GB2020/050996 on Apr. 22, 2020, now Pat. No. 11,892,429.

(30) Foreign Application Priority Data

May 7, 2019   (GB) ..................................... 1906433

(51) Int. Cl.
*G01N 27/64* (2006.01)
*G01N 1/24* (2006.01)
(Continued)

(52) U.S. Cl.
CPC ............. *G01N 27/64* (2013.01); *G01N 1/24* (2013.01); *G01N 1/4022* (2013.01); *G01N 1/405* (2013.01); *G01N 1/42* (2013.01); *G01N 1/44* (2013.01)

(58) Field of Classification Search
CPC ............................ G01N 27/62; G01N 27/623
See application file for complete search history.

(56) References Cited

U.S. PATENT DOCUMENTS 7,299,711 B1 *  11/2007  Linker ................. G01N 1/2214
                                                   73/863.23
2007/0077176 A1   4/2007  Lambert et al.
(Continued)

FOREIGN PATENT DOCUMENTS

GB       1046628 A      10/1966
WO   WO-2015/151537 A1  10/2015
(Continued)

OTHER PUBLICATIONS

*14 Common Types of Porous Materials*, Materials Weekly, May 25, 2019, (8 pages), (online), [Retrieved from the Internet Oct. 28, 2021] <URL: https://www.meetyoucarbide.com/14-common-types-of-porous-materials/>.
(Continued)

*Primary Examiner* — Tung X Nguyen
(74) *Attorney, Agent, or Firm* — Alston & Bird LLP

(57) ABSTRACT

A detector for, and a method of, detecting analytes in gases in described. The detector comprises a sorbent for sorbing therein and/or thereon and/or desorbing therefrom, an analyte included in a gas exposed thereto, at a zeroth temperature, pressure ($T_0$, $P_0$), a controller arranged to change the zeroth temperature, pressure ($T_0$, $P_0$) to a first temperature, pressure ($T_1$, $P_1$) according to a first equation, to desorb and/or sorb at least some of the analyte; and a sensor arranged to sense at least some of the analyte and to output a response corresponding to the sensed analyte. The response comprises and/or is a characteristic response of the analyte.

20 Claims, 16 Drawing Sheets

(51) Int. Cl.
  *G01N 1/40* (2006.01)
  *G01N 1/42* (2006.01)
  *G01N 1/44* (2006.01)

(56) References Cited

U.S. PATENT DOCUMENTS

| | | |
|---|---|---|
| 2008/0184886 A1 | 8/2008 | Tufts et al. |
| 2009/0317916 A1 | 12/2009 | Ewing et al. |
| 2013/0171687 A1 | 7/2013 | Moularat et al. |
| 2015/0168330 A1 | 6/2015 | Gryska et al. |
| 2016/0018373 A1 | 1/2016 | Pagé et al. |
| 2016/0096793 A1 | 4/2016 | Filipovic et al. |
| 2016/0146765 A1 | 5/2016 | Ovadia et al. |
| 2017/0189882 A1 | 7/2017 | Eisele et al. |
| 2017/0212069 A1 | 7/2017 | Nakao et al. |
| 2019/0025271 A1 | 1/2019 | Yan et al. |
| 2020/0166493 A1 | 5/2020 | Nojiri et al. |
| 2020/0393432 A1* | 12/2020 | Swanson .............. G01N 27/404 |
| 2022/0236222 A1 | 7/2022 | Hutter et al. |

FOREIGN PATENT DOCUMENTS

| | | |
|---|---|---|
| WO | WO-2018/079174 A1 | 5/2018 |
| WO | WO-2019/031260 A1 | 2/2019 |

OTHER PUBLICATIONS

Abdulrasheed, A.A. et al. "Surface Modification of Activated Carbon for Adsorption of $SO_2$ and $NO_x$: A Review of Existing and Emerging Technologies," *Renewable and Sustainable Energy Reviews*, vol. 94, pp. 1067-1085, Jul. 1, 2018, DOI: https://doi.org/10.1016/j.rser.2018.07.011.

Alfeel, Faten et al. *Using AFM to Determine the Porosity in Porous Silicon*, Journal of Materials Science and Engineering A, vol. 2, No. 9A, pp. 579-583, Sep. 10, 2012.

Arora, Meenakshi et al. "Surface Modification of Natural Zeolite by Chitosan and Its Use for Nitrate Removal in Cold Regions," *Cold Regions Science and Technology*, vol. 62, Issues 2-3, pp. 92-97, Jul. 2010, DOI: 10.1016/j.coldregions.2010.03.002.

Attard, Gary et al. *Surfaces*, Aug. 13, 1998, Section 2.7, pp. 71-75, Oxford University Press, ISBN: 0198556861.

Barbosa, Gustavo P. et al. "Design and Characterization of Chitosan-Zeolite Composite Films—Effect of Zeolite Type and Zeolite Dose on the Film Properties," *Materials Science and Engineering: C*, vol. 60, pp. 246-254, Mar. 2016, DOI: 10.1016/j.msec.2015.11.034.

Brinker, C.J. et al. *Sol-Gel Strategies for Controlled Porosity Inorganic Materials*, Journal of Membrane Science, vol. 94, pp. 85-102, Sep. 19, 1994, DOI: 10.1016/0376-7388(93)E0129-8.

*Bulletin of the American Physical Society*, APS March Meeting 2012, vol. 57, No. 1, Feb. 27-Mar. 2, 2012, Boston, Massachusetts, (1 page), (online), [Retrieved from the Internet Oct. 29, 2021] <URL: https://meetings.aps.org/Meeting/MAR12/Session/W33.12>.

Espinal, Laura. *Porosity and Its Measurement*, Characterization of Materials, Oct. 15, 2002, pp. 1-9.

European Examination Report for Great Britain Application No. GB1906433.6, dated Aug. 25, 2021, (5 pages), Intellectual Property Office, South Wales, United Kingdom.

International Searching Authority, International Search Report and Written Opinion for International Application No. PCT/GB2020/050996, dated Jul. 27, 2020, (17 pages), European Patent Office, Rijswijk, Netherlands.

Klient, Ch. et al. *Thermal Desorption Spectroscopy on Silicon*, Surface Science, vol. 231, (Year: 1990), pp. 177-187.

Lee, Seo Hyeon et al. *A Mini Review: Recent Advances In Surface Modification of Porous Silicon*, Materials, vol. 11, No. 2557, pp. 1-14, Dec. 15, 2018, DOI: 10.3390/ma11122557.

Liu, W.B. et al. "A General Dealloying Strategy to Nanoporous Intermetallics, Nanoporous Metals With Bimodel, and Unimodal Pore Size Distributions," *Corrosion Science*, vol. 58, pp. 133-138, Feb. 2, 20212, DOI: 10.1016/j.corsci.2012.01.023.

*Mesoporous Silica*, American Elements, (7 pages), (online), [Retrieved from the Internet Oct. 28, 2021] <URL: https://www.americanelements.com/mesoporous-silica-7631-86-9>.

Mummey, M.J. et al. *Decomposition of NO on Clean Pt Near Atmospheric Pressures*, Surface Science, vol. 109, (Year: 1981), pp. 43-59.

Neouze, Marie-Alexandra et al. "Surface Modification and Functionalization of Metl and Metal Oxide Nanoparticles by Organic Ligands," *Monatshefte fur Chemie*, vol. 139, pp. 183-195, Feb. 12, 2008, DOI: 10.1007/s00706-007-0775-2.

*NORIT® SX Plus CAT*, Millipore Sigma, (online), (5 pages), [Retrieved from the Internet Oct. 29, 2021] <URL: https://www.sigmaaldrich.com/US/en/product/aldrich/901937>.

Paes, Tiago Franca et al. *Simple Method for Measuring the Porosity, Thickness and Refractive Index of Porous Silicon, Based on the Fabry-Pérot Interference Spectrum*, Revista Brasileira de Aplicações de Vácuo, vol. 35, No. 117, pp. 117-122, Feb. 21, 2017, DOI:10.17563/rbav.v35i3.1044.

Shafeeyan, Mohammad et al. *A Review of Surface Modification of Activated Carbon for Carbon Dioxide*, Journal of Analytical and Applied Pyrolysis, vol. 89, pp. 143,151, Aug. 19, 2010, DOI: 10.1016/j/jaap.2010.07.006.

Shafer, M.W. et al. "The Chemistry of and Physics With Porous Sol-Gel Glasses," *Journal of Applied Physics*, vol. 61, No. 12, pp. 5438-5446, Jun. 15, 1987, DOI: https://doi.org/10.1063/1.338285.

Sinkó, Katalin. *Influence of Chemical Conditions on the Nanoporous Structure of Silicate Aerogels*, Materials, vol. 3, No. 1, pp. 704-740, Jan. 26, 2010, DOI: 10.3390/ma3010704.

*Smart Membranes*, Nanoporous Alumina, (1 page), (online), [Retrieved from the Internet Oct. 28, 2021] <URL: http://www.smartmembranes.de/en/products/nanoporous-alumina/>.

United Kingdom Search Report for United Kingdom Application No. GB1906433.6, dated Jul. 8, 2019, (7 pages), Intellectual Property Office, South Wales, United Kingdom.

Valden, M. et al. *Heterogeneity in the Surface Structure of a Cu{100}-c(2×2)-Pd Surface Alloy*, Chemical Physical Letters, vol. 228, Oct. 14, 1994, pp. 519-526.

Vilela, Sérgio M.F. et al. "A Robust Monolithic Metal-Organic Framework With Hierarchical Porosity," *ChemComm*, vol. 54, pp. 13088-13091, Oct. 25, 2018, DOI: 10.1039/c8cc07252c.

Wada, Tatsuaki et al. *A Thermal Desorption Analysis for the Adsorption of $CO_2$ on GaAs Photocathodes*, Surface Science, vol. 285, (Year: 1993), pp. 188-1996.

Yan, Zhang et al. "The Surface Modification of Zeolite 4A and Its Effect on the Water-Absorption Capability of Starch-G-Poly (Acrylic Acid) Composite," *Clays and Clay Minerals*, vol. 62, No. 3, pp. 211-213, Jun. 2014, DOI: 10.1346/CCMN.2014.0620305.

U.S. Appl. No. 17/608,667, filed Nov. 3, 2021, Allowed.

\* cited by examiner

DETECTOR FOR DETECTING ANALYTES IN GAS PHASE COMPRISING POROUS DIELECTRIC OR SEMICONDUCTING SORBENT AND CORRESPONDING DETECTION METHOD

CROSS-REFERENCE TO RELATED APPLICATIONS

The present application is a continuation of and claims priority to and the benefit of U.S. application Ser. No. 17/608,667, filed Nov. 3, 2021, which application further is a National Stage Application, filed under 35 U.S.C. § 371, of International Application No. PCT/GB2020/050996, filed Apr. 22, 2020, which international application claims priority to and the benefit of Great Britain Application No. 1906433.6, filed May 7, 2019; the contents of both of which as are hereby incorporated by reference in their entireties.

BACKGROUND

Related Field

The present invention relates to detectors for and methods of detecting analytes in gases.

Related Art

Some compounds, such as volatile organic compounds (VOCs), in the atmosphere present hazards to life at trace (low ppb) levels. For example, for environmental applications, guideline threshold values in indoor air are 81 ppb for formaldehyde, 1.9 ppb for naphthalene and 1.6 ppb or lower for benzene. It is expected that these guideline threshold values will be lowered—for some compounds, there are no safe exposure limits. Furthermore, other compounds, for example emission and/or greenhouse gases such as $CO_2$, $SO_2$ and NOx, are also relevant for environmental applications while other compounds, such as $NH_3$ and $H_2S$, are relevant for industrial applications, for example. Detection of explosive vapours, for security applications, is hampered by the low vapour pressure of explosives. For example, 2,4,6-trinitrotoluene (TNT) has a vapour pressure of $7.7 \times 10^{-6}$ mbar at ambient temperature while RDX has a vapour pressure of just $5.9 \times 10^{-9}$ mbar at ambient temperature. Hence, there is a need to reliably quantitatively and/or quantitatively detect such compounds (i.e. analytes) at low ppb levels, particularly to improve speed, sensitivity and/or selectivity of detection thereof.

Furthermore, these environmental and security applications require field-deployable, typically miniaturised, detectors, particularly for monitoring purposes, such as ubiquitous monitoring for rural, residential, commercial, industrial, transport and/or high risk locations. Typically, field-deployable detectors should be fast, simple, sensitive, reliable, robust and cost-effective.

Hence, there is a need to improve detection of analytes in gases.

BRIEF SUMMARY

It is one aim of the present invention, amongst others, to provide a detector for, and a method of, detecting analytes in gases which at least partially obviates or mitigates at least some of the disadvantages of the prior art, whether identified herein or elsewhere. For instance, it is an aim of embodiments of the invention to provide a field-deployable detector having improved selectivity of trace analyte detection, compared with conventional detectors. For instance, it is an aim of embodiments of the invention to provide a method of detecting analytes in gases having improved sensitivity while suitable for unattended, for example remote, analysis, such as for monitoring.

A first aspect provides a detector for detecting analytes in gases, comprising: a first sorbent of a set of sorbents, preferably wherein the first sorbent comprises and/or is an adsorbent, for sorbing, preferably adsorbing, therein and/or thereon and/or desorbing therefrom, a first analyte of a set of analytes included in a first gas of a set of gases exposed thereto, at a zeroth temperature, pressure $(T_0, P_0)$ of a set of temperatures, pressures (T, P);
  a controller arranged to change the zeroth temperature, pressure $(T_0, P_0)$ to a first temperature, pressure $(T_1, P_1)$ of the set of temperatures, pressures (T, P) according to a first equation of a set of equations, to desorb and/or sorb at least some of the first analyte; and
  a sensor arranged to sense at least some of the first analyte and to output a first response of a set of responses corresponding to the sensed first analyte;
  wherein the first response comprises and/or is a first characteristic response of a set of characteristic responses of the first analyte.

A second aspect provides a method of detecting analytes in gases, comprising: exposing a first sorbent of a set of sorbents, preferably wherein the first sorbent comprises and/or is an adsorbent, to a first gas of a set of gases, at a zeroth temperature, pressure $(T_0, P_0)$ of a set of temperatures, pressures (T, P);
  sorbing, preferably adsorbing, by the first sorbent, therein and/or thereon, and/or desorbing therefrom, a first analyte of a set of analytes included in the first gas;
  desorbing and/or sorbing at least some of the first analyte by controlling a change from the zeroth temperature, pressure $(T_0, P_0)$ to a first temperature, pressure $(T_1, P_1)$ of the set of temperatures, pressures (T, P) according to a first equation of a set of equations; and
  sensing at least some of the first analyte and outputting a first response of a set of responses corresponding to the sensed first analyte;
  wherein the first response comprises and/or is a first characteristic response of a set of characteristic responses of the first analyte.

A third aspect provides use of microporous and/or mesoporous silica, a zeolite, activated carbon and/or a metal organic framework, MOF, as an adsorbent for an analyte in a detector.

A fourth aspect provides use of temperature ramping to selectively adsorb or desorb an analyte, respectively to or from an adsorbent in a detector.

According to the present invention there is provided a detector, as set forth in the appended claims. Also provided is a method of detecting. Other features of the invention will be apparent from the dependent claims, and the description that follows.

Detector

The first aspect provides a detector for detecting analytes in gases, comprising: a first sorbent of a set of sorbents, preferably wherein the first sorbent comprises and/or is an adsorbent, for sorbing, preferably adsorbing, therein and/or thereon and/or desorbing therefrom, a first analyte of a set of analytes included in a first gas of a set of gases exposed thereto, at a zeroth temperature, pressure $(T_0, P_0)$ of a set of temperatures, pressures (T, P);

a controller arranged to change the zeroth temperature, pressure ($T_0$, $P_0$) to a first temperature, pressure ($T_1$, $P_1$) of the set of temperatures, pressures (T, P) according to a first equation of a set of equations, to desorb and/or sorb at least some of the first analyte; and a sensor arranged to sense at least some of the first analyte and to output a first response of a set of responses corresponding to the sensed first analyte;

wherein the first response comprises and/or is a first characteristic response of a set of characteristic responses of the first analyte.

In this way, the detector has improved selectivity of trace analyte detection, compared with conventional detectors.

In a first mode of operation, the first sorbent behaves as a pre-concentrator, thereby sorbing therein and/or thereon the first analyte, included in the first gas at a relatively lower concentration, at the zeroth temperature, pressure ($T_0$, $P_0$). Subsequently, the pre-concentrated first analyte is desorbed when the zeroth temperature, pressure ($T_0$, $P_0$) is changed to the first temperature, pressure ($T_1$, $P_1$), for example by heating from $T_0$ to $T_1$ (i.e. $T_1$ is greater than $T_0$) and/or reducing the pressure from $P_0$ to $P_1$ (i.e. $P_1$ is less than $P_0$). The desorbed first analyte is then sensed by the sensor at a relatively higher concentration. Since the desorbed first analyte is sensed by the sensor at the relatively higher concentration, thereby increasing relatively the first response, a sensitivity of detection of the first analyte is increased. Furthermore, since the pre-concentrated first analyte is desorbed when the zeroth temperature, pressure ($T_0$, $P_0$) is changed to the first temperature, pressure ($T_1$, $P_1$) according to the first equation, for example a predetermined heating curve and/or a predetermined pressure decrease curve, the pre-concentrated first analyte is desorbed during a particular temperature and/or pressure range, corresponding to a particular section of the first equation, and/or at a particular rate, thereby providing the first characteristic response. This characteristic first response provides improved selectivity, since different analytes may be distinguished by their respective characteristic responses for the first equation, thereby enabling classification and/or identification of the first analyte.

In a second mode of operation, the first sorbent behaves as a getter, thereby sorbing therein and/or thereon the first analyte, included in the first gas at a relatively higher concentration, when the zeroth temperature, pressure ($T_0$, $P_0$) is changed to the first temperature, pressure ($T_1$, $P_1$), for example by cooling from $T_0$ to $T_1$ (i.e. $T_1$ is less than $T_0$) and/or increasing the pressure from $P_0$ to $P_1$ (i.e. $P_1$ is greater than $P_0$), such that the first analyte is now included in the first gas at a relatively lower concentration. The lowered concentration of the first analyte is then sensed by the sensor. Since the pre-concentrated first analyte is sorbed when the zeroth temperature, pressure ($T_0$, $P_0$) is changed to the first temperature, pressure ($T_1$, $P_1$) according to the first equation, for example a predetermined cooling curve and/or a predetermined pressure increase curve, the pre-concentrated first analyte is sorbed during a particular temperature and/or pressure range, corresponding to a particular section of the first equation, and/or at a particular rate, thereby providing the first characteristic response. This characteristic first response provides improved selectivity, since different analytes may be distinguished by their respective characteristic responses for the first equation, thereby enabling identification of the first analyte.

Furthermore, since the operation of the detector is by, at least in part, changing the zeroth temperature, pressure ($T_0$, $P_0$) to a first temperature, pressure ($T_1$, $P_1$), such operation is compatible with unattended, for example remote, analysis, such as environmental and/or security monitoring. In addition, since the detector comprises the first sorbent, the controller and the sensor, the detector may be field-deployable.

It should be understood that the detector is for detecting analytes in gases, for example quantitatively and/or qualitatively. Such detectors are also known as gas detectors, analysers, instruments or sensors. In one example, the detector is a field-deployable detector, optionally comprising a power supply such as a battery and/or a photovoltaic cell. In one example, the detector has dimensions of at most 15 cm length by 15 cm width by 5 cm height i.e. relatively compact, such as a small detector, for example a hand-portable or hand-held detector or a wall- or ceiling-mountable detector. In one example, the detector comprises and/or is an Internet of Things (IoT) detector (also known as a smart detector). In one example, the detector has dimensions of at most 60 cm length by 60 cm width by 60 cm height i.e. a medium detector, for example a bench-top detector. In one example, the detector has dimensions of at most 120 cm length by 120 cm width by 120 cm height or larger i.e. a large detector, for example a floor-standing detector. The medium and/or large detectors may include a mass spectrometer as the sensor, for example. In one example, the detector is a chip detector i.e. integrating the first sorbent, the controller and the sensor on a chip, such as a micro detector.

Sorbent

The detector comprises the first sorbent of the set of sorbents, preferably wherein the first sorbent comprises and/or is an adsorbent.

The IUPAC defines sorption as a process by which a substance (sorbate) is sorbed (adsorbed or absorbed) on or in another substance (sorbent) while desorption is defined as the converse of adsorption, i.e. the decrease in the amount of adsorbed substance. The IUPAC defines adsorption as an increase in the concentration of a dissolved substance at the interface of a condensed and a liquid phase due to the operation of surface forces. Adsorption can also occur at the interface of a condensed and a gaseous phase. In contrast, the IUPAC defines absorption as a process of one material (absorbate) being retained by another (absorbent); this may be the physical solution of a gas, liquid, or solid in a liquid, attachment of molecules of a gas, vapour, liquid, or dissolved substance to a solid surface by physical forces, etc. In one preferred example, the first sorbent comprises and/or is an adsorbent (i.e. not an absorbent).

It should be understood that the first sorbent comprises and/or is a porous material, particularly a porous material having a high porosity. The number of pores and/or the number density of pores (i.e., porosity) will vary for different porous materials. Porous materials can be classified as low porosity, middle porosity, or high porosity based on the number of pores and/or the number density of pores. Generally, porous materials with low and middle porosity have closed pores, which behave like a phase of impurity. For porous materials with high porosity, there are two different cases according to various morphologies of the pore and the continuous solid phase. In one example, the first sorbent comprises and/or is a porous material, particularly a porous material having a high porosity. In the first case, the continuous solid constructs a two-dimensional array of polygons; the pore is isolated in space, taking on polygonal columniations accordingly; and the cross-sectional shape of the pore is commonly triangle, quadrangle, or hexagon. This structure looks similar to the hexagonal cell of a honeycomb, and such two-dimensional porous materials are called honeycomb materials. Porous materials with directional pores, which are called lotus-type porous materials, have a similar structure as honeycomb materials, but the cross-sectional shape of the pores for these materials is circular or elliptic, and the pore often cannot run through it, resulting in less uniformity of distribution and a lower density of the array. In one example, the first sorbent comprises and/or is a porous material, having a two-dimensional array of polygons and/or directional pores. In the second case, the continuous solid presents a three-dimensional reticulated structure, and such porous materials can be termed three-dimensional reticulated foamed materials. These materials have connective pores that are of a typical open cell structure. In the third case, the continuous solid shows the cell wall structure of pores of sphericity, elliptical sphericity, or polyhedron shape, and such three-dimensional porous materials can be called bubble-like foamed materials. Within these materials, the cell wall may separate many isolated closed pores or cells, forming a closed-cell, bubble-like foamed substance. The cell wall may make up open-cell, bubble-like foamed material as well. In the literature, three-dimensional, reticulated foamed materials are referred to as "open-cell foamed materials," closed-cell, bubble-like foamed materials are called "closed-cell foamed materials," and open-cell, bubble-like foamed materials are "half open-cell foamed materials." In one example, the first sorbent comprises and/or is a three-dimensional reticulated foamed material (i.e. comprising open pores). In one example, the first sorbent has a porosity in a range from 40 vol. % to 99.9 vol. %, preferably in a range from 45 vol. % to 99 vol. %, more preferably in a range from 50 vol. % to 95 vol. %, by volume of the first sorbent. Generally, the porosity may be determined as described by Espinal, L. (2012) Porosity and its Measurement, Characterization of Materials, edited by Elton N. Kaufmann, John Wiley & Sons, Inc. The porosity may be determined according to one or more of ASTM B922-10 Standard Test Method for Metal Powder Specific Surface Area by Physical Adsorption—Committee B09 on Metal Powder and Metal Powder Products; ASTM C1069-09 Standard Test Method for Specific Surface Area of Alumina or Quartz by Nitrogen Adsorption—Committee C21 on Ceramic Whitewares and Related Products; ASTM C1274-10 Standard Test Method for Advanced Ceramic Specific Surface Area by Physical Adsorption—Committee C28 on Advanced Ceramics; ASTM D1993-03 (2008) Standard Test Method for Precipitated Silica—Surface Area by Multipoint BET Nitrogen—Committee D11 on Rubber; ASTM D3663-03 (2008) Standard Test Method for Surface Area of Catalysts and Catalyst Carriers—Committee D32 on Catalysts; ASTM D4222-03 (2008) Standard Test Method for Determination of Nitrogen Adsorption and Desorption Isotherms of Catalysts and Catalyst Carriers by Static Volumetric Measurements—Committee D32 on Catalyst; ASTM D4365-95 (2008) Standard Test Method for Determining Micropore Volume and Zeolite Area of a Catalyst-Committee D32 on Catalysts; ASTM D4567-03 (2008) Standard Test Method for Single-Point Determination of Specific Surface Area of Catalysts and Catalyst Carriers Using Nitrogen Adsorption by Continuous Flow Method—Committee D32 on Catalysts; ASTM D4641-12 Standard Practice for Calculation of Pore Size Distributions of Catalysts and Catalysts Carriers from Nitrogen Desorption Isotherms—Committee D32 on Catalysts; ASTM D4780-12 Standard Test Method for Determination of Low Surface Area of Catalysts and Catalyst Carriers by Multipoint Krypton Adsorption-Committee D32 on Catalysts; ASTM D5604-96 (2012) Standard Test Method for Precipitated Silica—Surface Area by Single Point B.E.T. Nitrogen Adsorption-Committee D11 on Rubber; ASTM D6556-10 Standard Test Method for Carbon Black Total and External Surface Area by Nitrogen Adsorption—Committee D24 on Carbon Black. ASTM D1993-03(2008) is preferred. The porosity may be determined as described by Paes, T. F. Beloto, A. F., Galvão, E. C. S. and Berni, L. A. (2017) Simple method for measuring the porosity, thickness and refractive index of porous silicon, based on the Fabry-Perot interference spectrum, Revista Brasileira de Aplições de Vácuo, 35, 117, doi: 10.17563/rbav.v35i3.1044, as described by Alfeel, F., Awad, F., Alghoraibi, I. and Qamar, F. (2012) Using AFM to Determine the Porosity in Porous Silicon, Journal of Materials Science and Engineering, 2, 579-583 or gravimetrically. It should be understood that the first sorbent has a relatively large specific surface area (typically expressed in $m^2/g$ or $m^2/cm^3$, for example), thereby increasing an amount of the first analyte that may be sorbed, preferably adsorbed, thereby. Generally, it is desirable to increase the specific surface area, so as to increase an amount of sorbed first analyte. However, as the specific surface area is increased, time for the first analyte to diffuse into and/or out of the first sorbent increases, thereby increasing a latency of the detector and/or a width of the first response, such as a peak (also known as spike) width. The specific surface area may be determined by Brunauer-Emmett-Teller (BET) Surface Area Analysis or Barrett-Joyner-Halenda (BJH) Pore Size and Volume Analysis, for example. The specific surface area may be determined according to ISO 9277:2010 Determination of the specific surface area of solids by gas adsorption—BET method. Generally, the BET surface area is equal to total surface area if the pores are ≥2 nm and if the pores are open. Generally, total surface area is the actual "total" surface area of the porous material, and as in BET, it provides the surface area that it calculates based on the adsorption of a gas on the substance exposed surface, withholding some assumptions: the adsorption is monolayer; the adsorption is specific to one molecule per adsorption site; and all the adsorption sites have equal accessibility to the adsorbing gas molecules and the adsorption of all molecules is identical. BET analysis provides precise specific surface area evaluation of materials by nitrogen multilayer adsorption measured as a function of relative pressure using a fully automated analyser. The technique encompasses external area and pore area evaluations to determine the total specific surface area in $m^2/g$ yielding important information in studying the effects of surface porosity and particle size in many applications. BJH analysis can also be employed to determine pore area and specific pore volume using adsorption and desorption techniques. This technique characterises pore size distribution independent of external area due to particle size of the sample. In one example, the first sorbent has a specific surface area in a range from 50 $m^2/g$ to 10,000 $m^2/g$, preferably in a range from 200 $m^2/g$ to 5,000 $m^2/g$, more preferably in a range from 400 $m^2/g$ to 2,500 $m^2/g$. For example, mesoporous ruthenium oxide may have a specific surface are of 68 $m^2/g$. For example, mesoporous $MnO_2$ with an average pore size of 3-4 nm may have a BET surface area of 429 $m^2/g$. For example, mesoporous silica particles may have a specific surface area of 400-600 $m^2/g$ at an average pore diameter of 5 nm, a BET surface area of 923 $m^2/g$ at a pore volume of 0.92 $cm^3/g$ and at an average pore diameter of 6.8 nm and a specific surface area of 1030-1070 $m^2/g$ with a pore volume of 0.81-0.85 $cm^3/g$. For example, periodic mesoporous organosilica nanocubes may have a specific surface area of 1,880 $m^2/g$.

For example, mesoporous carbon may have a specific surface area of 2,079 m$^2$/g. For example, a zirconium-based MOF may have a BET area of 6,552 m$^2$/g.

Generally, the relatively lower thermal conductivity of porous materials is beneficial for applications as thermal insulators. In contrast, a relatively higher thermal conductivity of the first sorbent is preferred, thereby accelerating a rate of heating and/or cooling of the first sorbent. In one example, the first sorbent has a thermal conductivity at room temperature in a range from 0.01 Wm$^{-1}$K$^{-1}$ to 1.0 Wm$^{-1}$K$^{-1}$, preferably in a range from 0.05 Wm$^{-1}$K$^{-1}$ to 0.7 Wm$^{-1}$K$^{-1}$, more preferably in a range from 0.1 Wm$^{-1}$K$^{-1}$ to 0.5 Wm$^{-1}$K$^{-1}$. For example, the thermal conductivity of mesoporous silica particles prepared as fine powder and heat treated between 150 and 700 degrees C. is in a range from 0.03 to 0.08 Wm$^{-1}$K$^{-1}$. For example, the average thermal conductivity of cubic mesoporous silica films is 0.30±0.02 Wm$^{-1}$K$^{-1}$. For example, the average thermal conductivity of hexagonal mesoporous silica films is 0.20±0.01 Wm$^{-1}$K$^{-1}$. For example, a typical monolithic silica aerogel has a total thermal conductivity of ~0.017 Wm$^{-1}$K$^{-1}$.

In contrast, the thermal conductivity of bulk silica is in a range from 1.3 Wm$^{-1}$K$^{-1}$ to 1.5 Wm$^{-1}$K$^{-1}$ at room temperature, for example 1.38 Wm$^{-1}$K$^{-1}$ for silica having a bulk density of 2.203 gcm$^{-3}$.

In one example, the first sorbent comprises and/or is an adsorbent, for example a nanoporous adsorbent such as a microporous adsorbent or mesoporous adsorbent such as porous silicon, silica or alumina, an oxygen-containing material such as a zeolite, a carbon-based material such as activated carbon, a metal organic framework, MOF, a nanostructured metal and/or a porous glass. In one example, the first sorbent comprises and/or is a microporous and/or mesoporous dielectric or semiconducting material such as silica or silicon, a zeolite, activated carbon and/or a metal organic framework, MOF Generally, nanoporous materials comprise a regular organic or inorganic framework supporting a regular, porous structure. The size of the pores is generally 100 nanometers or smaller. Most nanoporous materials can be classified as bulk materials or membranes. Activated carbon and zeolites are two examples of bulk nanoporous materials, while cell membranes can be thought of as nanoporous membranes. A porous medium or a porous material is a material containing pores (voids). The skeletal portion of the material is often called the 'matrix' or 'frame'. The pores are typically filled with a fluid (liquid or gas). There are many natural nanoporous materials, but artificial (i.e. synthetic) materials can also be manufactured. One method of doing so is to combine polymers with different melting points, so that upon heating one polymer degrades. A nanoporous material with consistently sized pores has the property of letting only certain substances pass through, while blocking others.

Nanoporous materials can be subdivided into 3 categories, set out by IUPAC: microporous materials, having pores with diameters in a range from 0.2 nm to 2 nm; mesoporous materials, having pores with diameters in a range from 2 nm to 50 nm; and macroporous materials, having pores with diameters in a range from 50 nm to 1000 nm. In one example, the first sorbent comprises and/or is microporous material, having pores with diameters in a range from 0.2 nm to 2 nm or a mesoporous material, having pores with diameters in a range from 2 nm to 50 nm. Pore diameter may be measured using electron microscopy, for example scanning electron microscopy. Other techniques are known.

Typical mesoporous materials include some types of silica and alumina. Mesoporous oxides of niobium, tantalum, titanium, zirconium, cerium and tin are also known.

Porous silicon may be formed via stain etching, using hydrofluoric acid, nitric acid and water, or through use of an anodization cell, such as employing a platinum cathode and a silicon wafer anode immersed in a hydrogen fluoride electrolyte. The porous silicon may be dried such as by supercritical drying, freeze drying, pentane drying or slow evaporation, to reduce risk of cracking during drying. The surface of porous silicon may be modified to improve stability, for example. Often, freshly etched porous silicon may be unstable due to the rate of its oxidation by the atmosphere. Following the formation of porous silicon, its surface is covered with covalently bonded hydrogen. Although the hydrogen coated surface is sufficiently stable when exposed to inert atmosphere for a short period of time, prolonged exposure render the surface prone to oxidation by atmospheric oxygen. The oxidation promotes instability in the surface and is undesirable for many applications. An approach that can be taken is through thermal oxidation, involving heating the porous silicon to high temperatures of 800 or 1000° C. to promote oxidation, providing porous silica having good stability to aging and electronic surface passivation.

Porous silica may be formed by oxidation of porous silicon, either thermally or chemically, as described above, and is available commercially, for example from American Elements (USA) at https://www.americanelements.com/mesoporous-silica-7631-86-9.

Porous alumina may be formed using electrochemical etching, for example as described in Dusan Losic and Abel Santos 'Nanoporous Alumina' Springer Series in Materials Science, DOI 10.1007/978-3-319-20334-8, and is available commercially, for example from SmartMembranes GmbH (DE) at http://www.smartmembranes.de/en/products/nanoporous-alumina/.

Porous glasses and porous silica-based glasses may be formed by sol-gel processing, for example as described by Brinker, C. J., Sehgal, R., Hietala, S. L., Deshpande, R. D., Smith, D. M., Loy, D., and Ashley, C. S. (1994) Sol-Gel Strategies for Controlled Porosity Inorganic Materials, Journal of Membrane Science, 94. 85-102, doi:10.1016/0376-7388(93)E0129-8 or Shafer, M. W., Awschalom, D. D., Warnock, J. and Ruben, G. (1987) The Chemistry of and Physics with Porous Sol-Gel Glasses, Journal of Applied Physics, 61, 5438-5446, doi:10.1063/1.338285.

Aerogels, for example silica and silicate aerogels, may be formed as described by Sinko, K. (2010) Influence of Chemical Conditions on Nanoporous Structure of Silicate Aerogels, Materials, 3, 704-740, doi:10.3390/ma3010704.

Zeolites are microporous, aluminosilicate minerals commonly used as commercial adsorbents and catalysts. Zeolites occur naturally but are also produced industrially. 245 unique zeolite frameworks have been identified and over 40 naturally occurring zeolite frameworks are known. The zeolite structural group (Nickel-Strunz classification) includes:

09.GA.—Zeolites with T$_5$O$_{10}$ units (T=combined Si and Al)—fibrous zeolites Natrolite framework (NAT): gonnardite, natrolite, mesolite, paranatrolite, scolecite, tetranatrolite Edingtonite framework (EDI): edingtonite, kalborsite
Thomsonite framework (THO): thomsonite-series 09.GB.—Chains of single connected 4-membered rings Analcime framework (ANA): analcime, leucite, pollucite, wairakite Laumontite (LAU), yugawaralite (YUG), goosecreekite (GOO), montesommaite (MON)

09.GC.—Chains of doubly connected 4-membered rings
Phillipsite framework (PHI): harmotome, phillipsite-series
Gismondine framework (GIS): amicite, gismondine, garronite, gobbinsite Boggsite (BOG), merlinoite (MER), mazzite-series (MAZ), paulingite-series (PAU), perlialite (Linde type L framework, zeolite L, LTL)

09.GD.—Chains of 6-membered rings—tabular zeolites
Chabazite framework (CHA): chabazite-series, herschelite, willhendersonite and SSZ-13
Faujasite framework (FAU): faujasite-series, Linde type X (zeolite X, X zeolites),
Linde type Y (zeolite Y, Y zeolites)
Mordenite framework (MOR): maricopaite, mordenite
Offretite-wenkite subgroup 09.GD.25 (Nickel-Strunz, 10 ed): offretite (OFF), wenkite (WEN)
Bellbergite (TMA-E, Aiello and Barrer; framework type EAB), bikitaite (BIK), erionite-series (ERI), ferrierite (FER), gmelinite (GME), levyne-series (LEV), dachiardite-series (DAC), epistilbite (EPI)

09.GE.—Chains of $T_{10}O_{20}$ tetrahedra (T=combined Si and Al)
Heulandite framework (HEU): clinoptilolite, heulandite-series
Stilbite framework (STI): barrerite, stellerite, stilbite-series
Brewsterite framework (BRE): brewsterite-series
Others
Cowlesite, pentasil (also known as ZSM-5, framework type MFI), tschernichite (beta polymorph A, disordered framework, BEA), Linde type A framework (zeolite A, LTA)

In one example, the first sorbent comprises and/or is a zeolite having a structural group according to the Nickel-Strunz classification, as described above.

Mesoporous carbon is typically used for energy storage devices. Activated carbon is typically composed of a carbon framework having both mesoporosity and microporosity, depending on synthesis conditions. Activated carbons are internally porous microcrystalline, non-graphitic forms of carbon. The activated carbons possess large surface area (~1000 m²/g) and pore volumes which make them useful for applications in energy storage devices, catalysis, and for removal of impurities from gases and liquids. Activated carbon may be formed by chemical pre-processing followed by mechanical filtering, as described in http://meetings.aps.org/Meeting/MAR12/Session/W33.12, and is available commercially, for example from Sigma Aldrich (now Merck) at https://www.sigmaaldrich.com/catalog/product/aldrich/901937?lang=en&region=GB.

Metal-organic frameworks (MOFs) are a class of compounds consisting of metal ions or clusters coordinated to organic ligands to form one-, two-, or three-dimensional structures. MOFs are a subclass of coordination polymers, with the special feature that they are often porous. The organic ligands included are sometimes referred to as 'struts', one example being 1,4-benzenedicarboxylic acid (BDC). More formally, a metal-organic framework is a coordination network with organic ligands containing potential voids. A coordination network is a coordination compound extending, through repeating coordination entities, in one dimension, but with cross-links between two or more individual chains, loops, or spiro-links, or a coordination compound extending through repeating coordination entities in two or three dimensions; and finally a coordination polymer is a coordination compound with repeating coordination entities extending in one, two, or three dimensions. In some cases, the MOF pores are stable during elimination of the guest molecules (often solvents) and may be refilled with other compounds. MOFs may be formed as described by Vilela, S. M. F., Salcedo-Abraira, P., Micheron, L., Solla, E. L., Yot, P. G. and Horcajada, P. (2018) Robust Monolithic Metal-Organic Framework with Hierarchical Porosity, Chemical Communications, 54, doi:10.1039/C8CC07252C.

Nanoporous metals and nanoporous intermetallics may be formed as described by Liu, W. B., Zhang, S.C., Li, N., Zheng, J. W., An, S.S. and Xing, Y. (2012) A general dealloying strategy to nanoporous intermetallics, nanoporous metals with bimodal, and unimodal pore size distributions, Corrosion Science, 58, 133-138, doi:10.1016/j.corsci.2012.01.023.

In one example, the first sorbent comprises and/or is a porous material according to MCM series, SBA series, HMM series, TUD series, FSM series, KIT series, CMK series, FDU series, ZSM series, AlPO series, SAPO series, MSU series, HMS series and/or APM series, as described by https://www.meetyoucarbide.com/single-post/14-Common-Types-Of-Porous-Materials.

Mesoporous materials may also be formed as described by Wei Li, Jun Liu and Dongyuan Zhao (2016) Mesoporous materials for energy conversion and storage devices, Nature Reviews Materials volume 1, Article number: 16023.

In one example, the first sorbent does not comprise polydimethylsiloxane (PDMS) and/or divinylbenzene (DVB), for example PDMS/DVB fibres such as 65 µm PDMS/DVB fused silica 24Ga solid-phase microextraction (SPME) fibre assemblies available from Supelco, Bellefonte, PA (USA). PDMS, also known as dimethylpolysiloxane or dimethicone, belongs to a group of polymeric organosilicon compounds that are commonly referred to as silicones. That is, in one example, PDMS and/or DVB are explicitly disclaimed.

In one example, the first sorbent has a thickness in a range from 100 nm to 10 mm, preferably in a range from 5 µm to 5 mm, more preferably in a range from 25 µm to 2 mm, for example 50 µm.

In one example, the first sorbent has an outer surface area, exposable to the first gas, in a range from 1 mm² to 100 cm², preferably in a range from 10 mm² to 10 cm², more preferably in a range from 2.5 cm² to 7.5 cm², for example 5 cm². It should be understood that the outer surface area of the first sorbent is the macroscopic surface area, for example visible with a naked eye, as contrasted with the total surface area of the first sorbent. For example, a 1 cm by 1 cm plate of porous silica, having a mass of 1 g, has an (upper) outer surface area of 1 cm² and may have a total surface area of 50 m² or more.

In one example, the first sorbent comprises a planar shape, for example a plate or a disk, so as to enhance compactness. In one example, the first sorbent comprises a folded shape, for example a serpentine shape, so as to increase a flow path of the first gas thereacross. In one example, the first sorbent is arranged as louvres or slats, such that the first gas to flow therebetween. In one example, the first sorbent comprises directional pores and is arranged such that the first gas flows along the directional pores, through the first sorbent.

In one example, the first sorbent comprises a surface modifier for modifying adsorption of the first analyte thereon. In this way, the first sorbent may be modified to increase or decrease a rate and/or amount of the first analyte adsorbed and/or desorbed thereby. That is, the first sorbent may be chemically functionalised. Generally, the surface of the first sorbent may be modified by attaching a chemical species thereto (for example, by covalent bonding and/or physisorption), by coating (for example with a polymer, an oxide layer, a dye and/or a receptor) and/or chemically modifying the surface without using a coating (for example, by surface oxidation). For example, porous silicon may be modified as described in Lee, S. H., Kang, J. S. and Kim, D. (2018) A Mini-Review: Recent Advances in Surface Modification of Porous Silicon, Material, 11, 2557, doi:10.3390/ma11122557, such as by hydrosilylation, carbonization, oxidation, and/or hydrolytic condensation. For example, activated carbon may be surface modified with gaseous ammonia to affect adsorption of $CO_2$, as described by Shafeeyan, M. S., Daud, W. M. A. W., Houshmand, A. and Shamiri, A. (2010) A review of surface modification of activated carbon for carbon dioxide, Journal of Analytical and Applied Pyrolysis, 89, 143-151, doi:10.1016/j.jaap.2010.07.006. For example, activated carbon may be surface modified to affect adsorption of $SO_2$ and $NO_x$, as described by Abdulrasheed, A. A., Jalil, A. A., Triwahyono, S., Zaini, M. A. A., Gambo, Y. and Ibrahim, M. (2018) Surface modification of activated carbon for adsorption of $SO_2$ and $NO_x$: A review of existing and emerging technologies, Renewable and Sustainable Energy Reviews, 94, 1067-1085, doi: 10.1016/j.rser.2018.07.011. For example, natural zeolite may be surface modified, as described by Arora, M., Eddy, N. K., Mumford, K. A., Baba, J. M. and Stevens, G. W. (2010) Surface modification of natural zeolite by chitosan and its use for nitrate removal in cold regions, Cold Regions Science and Technology, 62, 92-97, doi: 10.106/j.coldregions.2010.03.002. For example, zeolite 4A may be surface modified, as described by Yan, Z., Lin., Z., Kai, M. and Ghozhu, M. (2014) The surface modification of zeolite 4A and its effect on the water-absorption capability of starch-g-poly (acrylic acid) composite. For example, metal and metal oxide nanoparticles may be surface modified, as described by Neouze, M. A. and Schubert, U. (2008) Surface modification and functionalization of metal and metal oxide particles by organic ligands, Montash Chem 139, 183-195 doi: 10.1007/s00706-007-0775-2. Other surface modification processes are known.

In one example, the set of sorbents includes S sorbents, wherein S is a natural number greater than 1, for example 2, 3, 4, 5, 6, 7, 8, 9, 10 or more. For example, each sorbent may be selected to sorb, preferably adsorb, a particular compound. Each sorbent may be as described above with respect to the first sorbent.

First Gas

In one example, the first gas comprises and/or is an inert gas, for example He, Ar, $N_2$, and/or mixtures thereof, such as 99.99% $N_2$ or better, for example for laboratory applications. In one example, the first gas comprises and/or is air (for example, for environmental and/or security applications). In one example, the first gas is substantially static or static. In one example, the first gas comprises and/or is ambient air (i.e. moves according to ambient environment). In one example, the first gas is actively flowed, for example pumped.

Controller

The detector comprises the controller arranged to change the zeroth temperature, pressure ($T_0$, $P_0$) to the first temperature, pressure ($T_1$, $P_1$) of the set of temperatures, pressures (T, P) according to the first equation of the set of equations, to desorb and/or sorb at least some of the first analyte.

In one example, the controller comprises and/or is a processor, a computer comprising a processor and a memory, an embedded a logic controller such as a programmable logic controller (PLC) and/or System on a Chip (SoC) such as a Field Programmable Gate Array (FPGA) or an Application Specific Integrated Circuit (ASIC), having instructions thereon which when performed by the controller, change the zeroth temperature, pressure ($T_0$, $P_0$) to the first temperature, pressure ($T_1$, $P_1$) of the set of temperatures, pressures (T, P) according to the first equation of the set of equations. In one example, the first equation of the set of equations is stored in a memory of the controller. In one example, the controller comprises an interface, for example a Serial Communication Interfaces (SCI) such as RS-232, RS-422 and/or RS-485, a Synchronous Serial Communication Interface such as I2C, SPI, SSC and/or ESSI (Enhanced Synchronous Serial Interface), a Universal Serial Bus (USB) interface, a Multi Media Cards such as an SD card and/or a Compact Flash, a network interface such as an Ethernet and/or a LonWorks interface, a fieldbus such as a CAN-Bus, LIN-Bus and/or a PROFIBUS, a Discrete IO (also known as a General Purpose Input/Output (GPIO) interface), Analog to Digital/Digital to Analog (ADC/DAC) interface and/or a wireless interface such as an RF-based interface such as Bluetooth, Bluetooth low energy, ANT, ZigBee, RF4CE, NFC, and/or Wi-Fi, and/or an IR interface, thereby providing unidirectional or bidirectional communication. In this way, the controller may receive the first equation of the set of equations, for example from a server, and/or transmit the first response, for example to the server.

In one example, the controller is arranged to change only the zeroth temperature ($T_0$) to the first temperature ($T_1$). That is, the controller may be arranged to change only temperature, for example by heating and/or cooling, without directly changing pressure. It should be understood that changing the temperature may result in a change of pressure. However, such a change in pressure is not controlled by the controller (i.e. pressure change not relevant to operation of the detector). In one example, the controller is arranged to change only the zeroth temperature ($T_0$) to the first temperature ($T_1$) at a substantially constant pressure or a constant pressure such that the zeroth pressure ($P_0$) is substantially the same as the first pressure ($P_1$), for example ambient pressure. It should be understood that the ambient pressure may change.

In one example, the controller is arranged to change only the zeroth pressure ($P_0$) to the first pressure ($P_1$). That is, the controller may be arranged to change only pressure, for example by increasing and/or decreasing the pressure, without directly changing temperature. It should be understood that changing the pressure may result in a change of temperature. However, such a change in temperature is not controlled by the controller (i.e. temperature change not relevant to operation of the detector). In one example, the controller is arranged to change only the zeroth pressure ($P_0$) to the first pressure ($P_1$) at a substantially constant temperature or a constant temperature such that the zeroth temperature ($T_0$) is substantially the same as the first temperature ($T_1$), for example ambient temperature. It should be understood that the ambient temperature may change.

Equations

The detector comprises the controller arranged to change the zeroth temperature, pressure ($T_0$, $P_0$) to the first temperature, pressure $(T_1, P_1)$ of the set of temperatures, pressures $(T, P)$ according to the first equation of the set of equations.

It should be understood that the first equation thus defines how, over time, the zeroth temperature, pressure $(T_0, P_0)$ is changed to the first temperature, pressure $(T_1, P_1)$. In one preferred example, the first equation comprises and/or is linear ramp (upwards and/or downwards) between the zeroth temperature, pressure $(T_0, P_0)$ and the first temperature, pressure $(T_1, P_1)$, for example with respect to temperature T and/or pressure P. In one example, the first equation comprises and/or is non-linear ramp (upwards and/or downwards), for example a curve, between the zeroth temperature, pressure $(T_0, P_0)$ and the first temperature, pressure $(T_1, P_1)$, for example with respect to temperature T and/or pressure P. In one example, the first equation comprises one or more hold time periods, before, during and/or after a linear or non-linear ramp, during which temperature T and/or pressure P are constant. In one example, the first equation comprises one or more steps, before, during and/or after a linear or non-linear ramp, during which temperature T and/or pressure P are increased stepwise. In one example, the first equation is pre-determined (i.e. fixed). In one example, the first equation is user-determined (for example, selectable and/or programmable).

In one example, the zeroth temperature $T_0$ is in a range from 0° C. to 300° C., preferably in a range from 1° C. to 250° C., more preferably in a range from 1° C. to 200° C., even more preferably in a range from 2° C. to 150° C., most preferably in a range from 3° C. to 100° C., for example 5° C. In one example, the first temperature $T_1$ is in a range from 0° C. to 300° C., preferably in a range from 10° C. to 250° C., more preferably in a range from 20° C. to 200° C., even more preferably in a range from 30° C. to 150° C., most preferably in a range from 40° C. to 100° C., for example 50° C. In one example, the second temperature $T_2$ is in a range from 0° C. to 300° C., preferably in a range from 10° C. to 250° C., more preferably in a range from 20° C. to 200° C., even more preferably in a range from 30° C. to 150° C., most preferably in a range from 40° C. to 100° C., for example 50° C.

In one example, the zeroth pressure $P_0$ is in a range from 1 mbar to 10,000 mbar, preferably in a range from 5 mbar to 5,000 mbar, more preferably in a range from 10 mbar to 1,000 mbar. In one example, the first pressure $P_1$ is in a range from 0.1 mbar to 10,000 mbar, preferably in a range from 1 mbar to 2,500 mbar, more preferably in a range from 10 mbar to 500 mbar. In one example, the second pressure $P_2$ is in a range from 0.1 mbar to 10,000 mbar, preferably in a range from 1 mbar to 2,500 mbar, more preferably in a range from 10 mbar to 500 mbar.

In one example, the first equation comprises and/or is linear ramp (upwards and/or downwards) between the zeroth temperature, pressure $(T_0, P_0)$ and the first temperature, pressure $(T_1, P_1)$, with respect to temperature T, wherein the linear ramp is in a range from 0.1° C./min to 500° C./min, preferably in a range from 1° C./min to 150° C./min, more preferably in a range from 1° C./min to 50° C./min, most preferably in a range from 3° C./min to 25° C./min, for example 4° C./min, 5° C./min, 6° C./min, 7° C./min, 8° C./min, 9° C./min or 10° C./min. In one example, a duration of the linear ramp is from 0.01 s to 10,000 s, preferably in a range from 0.1 s to 5,000 s, more preferably in a range from 1 s to 1,000 s. In one example, the first equation comprises and/or is non-linear ramp (upwards and/or downwards), with respect to temperature T, wherein the non-linear ramp is as described with respect to the linear-ramp.

In one example, the first equation comprises and/or is linear ramp (upwards and/or downwards) between the zeroth temperature, pressure $(T_0, P_0)$ and the first temperature, pressure $(T_1, P_1)$, with respect to pressure P, wherein the linear ramp is in a range from 1 mbar/s to 1000 mbar/s, preferably in a range from 10 mbar/s to 100 mbar/s. In one example, a duration of the linear ramp is from 0.01 s to 10,000 s, preferably in a range from 0.1 s to 5,000 s, more preferably in a range from 1 s to 1,000 s. In one example, the first equation comprises and/or is non-linear ramp (upwards and/or downwards), with respect to pressure P, wherein the non-linear ramp is as described with respect to the linear-ramp.

In one example, the first equation comprises one or more hold time periods, before, during and/or after a linear or non-linear ramp, during which temperature T and/or pressure P are constant, wherein a hold time period is in a range from 1 s to 60 minutes, preferably in a range from 0.5 minutes to 30 minutes, more preferably in a range from 2 minutes to 15 minutes, for example 5 minutes or 10 minutes.

Sensor

The detector comprises the sensor arranged to sense at least some of the first analyte and to output the first response of the set of responses corresponding to the sensed first analyte.

In one example, the detector comprises a set of sensors including the sensor (i.e. a first sensor of the set of sensors). In this way, sensors appropriate for different analytes may be included.

In one example, the sensor comprises and/or is a photoionization detector, PID, an electrochemical detector, an optical detector, for example an IR or a UV detector and/or an ion spectrometer, for example a mass spectrometer or an ion mobility spectrometer, a catalytic bead detector, a semiconductor detector, an ultrasonic detector, a holographic detector or a mechanical resonance gas sensor, such as a microcantilever sensor or MEMS mass sensor. Other sensors are known. In one example, the sensor comprises and/or is a broadband analyte detector such as a PID, an electrochemical detector for example of amperometric and/or potentiometric type, a metal oxide sensor (MOx) for sensing change of conductivity (c.f. chemical reaction), an optical sensor for example a UV portable spectrometer and/or a portable or micro-gas chromatograph (µGC) that combines micro column with MOx and/or PID.

In one example, the sensor is provided by a Peltier heater/cooler. For example, an amount of the first analyte desorbed from the first sorbent may be determined from an amount of heat input by the Peltier heater/cooler during desorption, since desorption is typically an endothermic process. Similarly, an amount of the first analyte sorbed on and/or the first sorbent may be determined. In one example, the sensor is provided by a mass balance.

First Response

It should be understood that the first response is a signal generated and output by the sensor in response to sensing the first analyte, for example a value, a voltage, a current.

In one example, the first response corresponds to a height of a signal, for example at a particular time, and/or an area of a signal (i.e. integrated height over time), for example for a particular time period. The first response may be optionally processed, for example by smoothing and/or background-subtraction. Background-subtracted may also be known as baseline-subtracted. The set of responses may comprise responses at different times and/or for different time periods.

The first response comprises and/or is the first characteristic response of the set of characteristic responses of the first analyte.

This characteristic first response provides improved selectivity, since different analytes may be distinguished by their respective characteristic responses for the first equation, thereby enabling classification (i.e. class or type of analyte, such as class of VOC or class of explosive, for example) and/or identification (i.e. unique identification) of the first analyte. It should be understood that the first response may be thus specific to the first analyte (and/or of a class of the first analyte). In other words, the first response may provide a fingerprint for the first analyte. In one preferred example, the first response comprises and/or is a profile (or shape) of a signal generated by the sensor as a function of time (i.e. acquisition or measurement or analysis time).

Temperature and Pressure

The first sorbent is for sorbing, preferably adsorbing, therein and/or thereon and/or desorbing therefrom, the first analyte of the set of analytes included in the first gas of the set of gases exposed thereto, at the zeroth temperature, pressure $(T_0, P_0)$ of the set of temperatures, pressures $(T, P)$ and the controller is arranged to change the zeroth temperature, pressure $(T_0, P_0)$ to the first temperature, pressure $(T_1, P_1)$ of the set of temperatures, pressures $(T, P)$.

It should be understood that the zeroth temperature, pressure $(T_0, P_0)$ merely refers to a term in the set of temperatures, pressures $(T, P)$ that precedes that term otherwise regarded as the first term i.e. the first temperature, pressure $(T_1, P_1)$. It should be understood that the set of temperatures, pressures $(T, P)$ refers to unique temperature-pressure $(T, P)$ pairs, noting that the same temperature $(P)$ may be paired with a plurality of pressures $(P)$ and vice versa. When heating from $T_0$ to $T_1$, $T_1$ is greater than $T_0$ while conversely, when cooling from $T_0$ to $T_1$, $T_1$ is less than $T_0$. Similarly, when reducing the pressure from $P_0$ to $P_1$, $P_1$ is less than $P_0$ while conversely, when increasing the pressure from $P_0$ to $P_1$, $P_1$ is greater than $P_0$. Note that the temperature may be changed at constant pressure. Similarly, the pressure may be changed at constant temperature.

Analytes

The first sorbent is for sorbing, preferably adsorbing, therein and/or thereon and/or desorbing therefrom, the first analyte of the set of analytes included in a first gas of a set of gases exposed thereto, at a zeroth temperature, pressure $(T_0, P_0)$ of a set of temperatures, pressures $(T, P)$.

In one example, the first analyte is a VOC. Directive 2010/75/EU of the European Parliament and the Council on industrial emissions (the Industrial Emissions Directive or IED) defines that 'volatile organic compound' means any organic compound as well as the fraction of creosote, having at 293.15 K a vapour pressure of 0.01 kPa or more, or having a corresponding volatility under the particular conditions of use. 'Organic compound' means any compound containing at least the element carbon and one or more of hydrogen, halogens, oxygen, sulphur, phosphorus, silicon or nitrogen, with the exception of carbon oxides and inorganic carbonates and bicarbonates. Other definitions are known. In one example, the first analyte is a VOC selected from List 1.

In one example, the set of analytes comprises N analytes, where N is a natural number greater than 1, for example 2, 5, 10, 20, 50, 100, 200, 500 or more. In one example, the set of analytes comprises N VOCs selected from List 1. In one example, the set of analytes comprises all the VOCs selected from List 1.

PROPANE, N-BUTANE, N-PENTANE, N-HEXANE, N-HEPTANE, N-OCTANE, N-NONANE, N-DECANE, N-UNDECANE, N-DODECANE, N-TRIDECANE, N-TETRADECANE, N-PENTADECANE, N-C16, N-C17, N-C18, N-C19, N-C20, N-C21, N-C22, ISOBUTANE, NEOPENTANE, ISOPENTANE, BRANCHED C5 ALKANES, 2, 2-DIMETHYL BUTANE, 2, 3-DIMETHYL BUTANE, 2-METHYL PENTANE, 3-METHYLPENTANE, BRANCHED C6 ALKANES, 2, 2, 3-TRIMETHYL BUTANE, 2, 2-DIMETHYL PENTANE, 2, 3-DIMETHYL PENTANE, 2, 4-DIMETHYL PENTANE, 2-METHYL HEXANE, 3, 3-DIMETHYL PENTANE, 3-METHYL HEXANE, BRANCHED C7 ALKANES, 2, 2, 3, 3-TETRAMETHYL BUTANE, 2, 2, 4-TRIMETHYL PENTANE, 2, 2-DIMETHYL HEXANE, 2, 3, 4-TRIMETHYL PENTANE, 2, 3-DIMETHYL HEXANE, 2,4-DIMETHYL HEXANE, 2, 5-DIMETHYL HEXANE, 2-METHYL HEPTANE, 3-METHYL HEPTANE, 4-METHYL HEPTANE, BRANCHED C8 ALKANES, 2, 2, 5-TRIMETHYL HEXANE, 2, 3, 5-TRIMETHYL HEXANE, 2, 4-DIMETHYL HEPTANE, 2-METHYL OCTANE, 3, 3-DIETHYL PENTANE, 3, 5-DIMETHYL HEPTANE, 4-ETHYL HEPTANE, 4-METHYL OCTANE, BRANCHED C9 ALKANES, 2, 4-DIMETHYL OCTANE, 2, 6-DIMETHYL OCTANE, 2-METHYL NONANE, 3, 4-DIETHYL HEXANE, 3-METHYL NONANE, 4-METHYL NONANE, 4-PROPYL HEPTANE, BRANCHED C10 ALKANES, 2, 6-DIMETHYL NONANE, 3, 5-DIETHYL HEPTANE, 3-METHYL DECANE, 4-METHYL DECANE, BRANCHED C11 ALKANES, 2, 6-DIETHYL OCTANE, 3, 6-DIMETHYL DECANE, 3-METHYL UNDECANE, 5-METHYL UNDECANE, BRANCHED C12 ALKANES, 3, 6-DIMETHYL UNDECANE, 3, 7-DIETHYL NONANE, 3-METHYL DODECANE, 5-METHYL DODECANE, BRANCHED C13 ALKANES, 3, 7-DIMETHYL DODECANE, 3, 8-DIETHYL DECANE, 3-METHYL TRIDECANE, 6-METHYL TRIDECANE, BRANCHED C14 ALKANES, 3, 7-DIMETHYL TRIDECANE, 3, 9-DIETHYL UNDECANE, 3-METHYL TETRADECANE, 6-METHYL TETRADECANE, BRANCHED C15 ALKANES, 3-METHYL PENTADECANE, 4, 8-DIMETHYL TETRADECANE, 7-METHYL PENTADECANE, BRANCHED C16 ALKANES, BRANCHED C17 ALKANES, BRANCHED C18 ALKANES, CYCLOPROPANE, CYCLOBUTANE, CYCLOPENTANE, CYCLOHEXANE, C6 CYCLOALKANES, ISOPROPYL CYCLOPROPANE, METHYLCYCLOPENTANE, 1, 3-DIMETH. CYCLOPENTANE, CYCLOHEPTANE, C7 CYCLOALKANES, ETHYL CYCLOPENTANE, METHYLCYCLOHEXANE, 1, 3-DIMETHYL CYCLOHEXANE, CYCLOOCTANE, C8 CYCLOALKANES, ETHYLCYCLOHEXANE, PROPYL CYCLOPENTANE, C9 BICYCLOALKANES, 1, 1, 3-TRIMETHYL CYCLOHEXANE, 1-ETH.-4-METH. CYCLOHEXANE, PROPYL CYCLOHEXANE, C9 CYCLOALKANES, C10 BICYCLOALKANES, 1, 3-DIETHYL-CYCLOHEXANE, 1, 4-DIETHYL-CYCLOHEXANE, 1-METH.-3-ISOPR. CYCLOHEXANE, BUTYL CYCLOHEXANE, C10 CYCLOALKANES, C11 BICYCLOALKANES, 13-DIETH-5-ME. CYCLOHEXANE, 1-ETHYL-2-PROPYL CYCLOHEXANE, PENTYL CYCLOHEXANE, C11 CYCLOALKANES, C12 BICYCLOALKANES, C12 CYCLOALKANES, 1, 3, 5-TRIETHYL CYCLOHEXANE, 1-METH.4-PENTYL CYCLOHEXANE, HEXYL CYCLOHEXANE, C13 BICYCLOALKANES, 13-DIETH-5-PENT CYCLOHEXANE, 1-METH.-2-HEXYL-CYCLOHEXANE, HEPTYL CYCLOHEXANE, C13 CYCLOALKANES, C14 BICYCLOALKANES, 13-DIPROP-5-ETH CYCLOHEXANE,

1-METH.4-HEPTYL CYCLOHEXANE, OCTYL CYCLOHEXANE, C14 CYCLOALKANES, C15 BICYCLOALKANES, 135-TRIPROPYL CYCLOHEXANE, 1-METHYL-2-OCTYL CYCLOHEXANE, NONYL CYCLOHEXANE, C15 CYCLOALKANES, 1, 3-PROP.-5-BUTYL CYCLOHEXANE, 1-METHYL-4-NONYL CYCLOHEXANE, DECYL CYCLOHEXANE, C16 CYCLOALKANES, ETHENE, PROPENE, 1-BUTENE, 1-PENTENE, 3-METHYL-1-BUTENE, 1-HEXENE, 3, 3-DIMETHYL-1-BUTENE, 3-METHYL-1-PENTENE, 4-METHYL-1-PENTENE, 1-HEPTENE, 1-OCTENE, 1-NONENE, 1-DECENE, 1-UNDECENE, 1-DODECENE, 1-TRIDECENE, 1-TETRADECENE, 1-PENTADECENE, C4 TERMINAL ALKENES, ISOBUTENE, 2-METHYL-1-BUTENE, C5 TERMINAL ALKENES, 2, 3-DIMETHYL-1-BUTENE, 2-ETHYL-1-BUTENE, 2-METHYL-1-PENTENE, C6 TERMINAL ALKENES, 2, 3, 3-TRIMETHYL-1-BUTENE, C7 TERMINAL ALKENES, 3-METHYL-2-ISOPROPYL-1-BUTENE, C8 TERMINAL ALKENES, C9 TERMINAL ALKENES, C10 TERMINAL ALKENES, C11 TERMINAL ALKENES, C12 TERMINAL ALKENES, C13 TERMINAL ALKENES, C14 TERMINAL ALKENES, C15 TERMINAL ALKENES, CIS-2-BUTENE, C4 ALKENES, C4 INTERNAL ALKENES, TRANS-2-BUTENE, 2-PENTENE, 2-METHYL-2-BUTENE, CIS-2-PENTENE, C5 ALKENES, C5 INTERNAL ALKENES, TRANS-2-PENTENE, 2, 3-DIMETHYL-2-BUTENE, 2-HEXENE, 2-METHYL-2-PENTENE, CIS-2-HEXENE, CIS-3-HEXENE, CIS-3-METHYL-2-HEXENE, C6 ALKENES, C6 INTERNAL ALKENES, TRANS-2-HEXENE, TRANS-3-HEXENE, TRANS 3-METHYL-2-HEXENE, TRANS 4-METHYL-2-HEXENE, 2, 3-DIMETHYL-2-HEXENE, 2-HEPTENES, CIS-3-HEPTENE, C7 ALKENES, C7 INTERNAL ALKENES, TRANS-2-HEPTENE, TRANS-3-HEPTENE, TRANS 4, 4-DIMETHYL-2-PENTENE, 3-OCTENES, CIS-4-OCTENE, C8 ALKENES, C8 INTERNAL ALKENES, TRANS 2, 2-DIMETHYL 3-HEXENE, TRANS 2, 5-DIMETHYL 3-HEXENE, TRANS-3-OCTENE, TRANS-4-OCTENE, 2, 4, 4-TRIMETHYL-2-PENTENE, 3-NONENES, C9 ALKENES, C9 INTERNAL ALKENES, TRANS-4-NONENE, 3, 4-DIETHYL-2-HEXENE, C10 3-ALKENES, C10 ALKENES, C10 INTERNAL ALKENES, CIS-5-DECENE, TRANS-4i-DECENE, C11 3-ALKENES, C11 ALKENES, C11 INTERNAL ALKENES, TRANS-5-UNDECENE, C12 2-ALKENES, C12 3-ALKENES, C12 ALKENES, C12 INTERNAL ALKENES, TRANS-5-DODECENE, C13 3-ALKENES, C13 ALKENES, C13 INTERNAL ALKENES, TRANS-5-TRIDECENE, C14 3-ALKENES, C14 ALKENES, C14 INTERNAL ALKENES, TRANS-5-TETRADECENE, C15 3-ALKENES, C15 ALKENES, C15 INTERNAL ALKENES, TRANS-5-PENTADECENE, CYCLOPENTENE, 1-METHYL CYCLOPENTENE, CYCLOHEXENE, 1-METHYL CYCLOHEXENE, 4-METHYL CYCLOHEXENE, 1, 2-DIMETHYL CYCLOHEXENE, 1, 3-BUTADIENE, ISOPRENE, C6 CYCLIC OR DI-OLEFINS, C7 CYCLIC OR DI-OLEFINS, C8 CYCLIC OR DI-OLEFINS, C9 CYCLIC OR DI-OLEFINS, C10 CYCLIC OR DI-OLEFINS, C11 CYCLIC OR DI-OLEFINS, C12 CYCLIC OR DI-OLEFINS, C13 CYCLIC OR DI-OLEFINS, C14 CYCLIC OR DI-OLEFINS, C15 CYCLIC OR DI-OLEFINS, CYCLOPENTADIENE, A-PINENE, B-PINENE, 3-CARENE, D-LIMONENE, SABINENE, TERPENE, STYRENE, A-METHYL STYRENE, C9 STYRENES, C10 STYRENES, BENZENE, TOLUENE, ETHYL BENZENE, C9 MONOSUB. BENZENES, ISOPROPYL BENZENE (CUMENE), N-PROPYL BENZENE, C10 MONOSUB. BENZENES, N-BUTYL BENZENE, S-BUTYL BENZENE, C11 MONOSUB. BENZENES, C12 MONOSUB. BENZENES, C13 MONOSUB. BENZENES, C8 DISUB. BENZENES, M-XYLENE, O-XYLENE, P-XYLENE, C9 DISUB. BENZENES, C10 DISUB. BENZENES, C11 DISUB. BENZENES, C12 DISUB. BENZENES, C13 DISUB. BENZENES, ISOMERS OF ETHYLBENZENE, 1, 2, 3-TRIMETHYL BENZENE, 1, 2, 4-TRIMETHYL BENZENE, 1, 3, 5-TRIMETHYL BENZENE, ISOMERS OF PROPYLBENZENE, C9 TRISUB. BENZENES, ISOMERS OF BUTYLBENZENE, C10 TRISUB. BENZENES, C10 TETRASUB. BENZENES, ISOMERS OF PENTYLBENZENE, C11 TRISUB. BENZENES, C11 TETRASUB. BENZENES, C11 PENTASUB. BENZENES, ISOMERS OF HEXYLBENZENE, C12 TRISUB. BENZENES, C12 TETRASUB. BENZENES, C11 PENTASUB. BENZENES, C12 HEXAASUB. BENZENES, C13 TRISUB. BENZENES, INDAN, NAPHTHALENE, TETRALIN, 1-METHYL NAPHTHALENE, 2-METHYL NAPHTHALENE, METHYL NAPHTHALENES, C11 TETRALIN OR INDANE, 2, 3-DIMETHYL NAPHTH., C12 MONOSUB. NAPHTH., C12 DISUB. NAPHTHALENES, DIMETHYL NAPHTHALENES, C13 MONOSUB. NAPHTH., C13 DISUB. NAPHTHALENES, C13 TRISUB. NAPHTHALENES, ACETYLENE, METHYL ACETYLENE, 2-BUTYNE, ETHYL ACETYLENE, METHANOL, ETHANOL, ISOPROPYL ALCOHOL, N-PROPYL ALCOHOL, ISOBUTYL ALCOHOL, N-BUTYL ALCOHOL, S-BUTYL ALCOHOL, T-BUTYL ALCOHOL, CYCLOPENTANOL, 2-PENTANOL, 3-PENTANOL, PENTYL ALCOHOL, CYCLOHEXANOL, 1-HEXANOL, 2-HEXANOL, 1-HEPTANOL, 1-OCTANOL, 2-OCTANOL, 2-ETHYL-1-HEXANOL, 3-OCTANOL, 4-OCTANOL, 8-METHYL-1-NONANOL (ISODECYL ALCOHOL), ETHYLENE GLYCOL, PROPYLENE GLYCOL, 1, 2-BUTANEDIOL, GLYCEROL, 2-METHYL-2,4-PENTANEDIOL, 1, 2-DIHYDROXY HEXANE, DIMETHYL ETHER, TRIMETHYLENE OXIDE, TETRAHYDROFURAN, DIETHYL ETHER, DIMETHOXY METHANE, ALPHA-METHYLTETRAHYDROFURAN, TETRAHYDROPYRAN, ETHYL ISOPROPYL ETHER, METHYL N-BUTYL ETHER, METHYL T-BUTYL ETHER, ETHYL N-BUTYL ETHER, ETHYL T-BUTYL ETHER, METHYL T-AMYL ETHER, DI N-PROPYL ETHER, 2-BUTYL TETRAHYDROFURAN, DI-N-BUTYL ETHER, DI-ISOBUTYL ETHER, DI-N-PENTYL ETHER, 2-METHOXYETHANOL, 2-METHOXY-1-PROPANOL, 2-ETHOXYETHANOL, 1-METHOXY-2-PROPANOL, 2-PROPOXYETHANOL, 3-ETHOXY-1-PROPANOL, 3-METHOXY-1-BUTANOL, 1-ETHOXY-2-PROPANOL, DIETHYLENE GLYCOL, 3 METHOXY-3 METHYL-BUTANOL, 2-BUTOXYETHANOL, 1-PROPOXY-2-PROPANOL, 2-(2-METHOXYETHOXY) ETHANOL, N-BUTOXY-2-PROPANOL, 1-TERT-BUTOXY-2-PROPANOL, 2-TERT-BUTOXY-1-PROPANOL, 2-(2-ETHOXYETHOXY) ETOH, DIPROPYLENE GLYCOL, DIPROPYLENE GLYCOL METHYL ETHER, 2-(2-BUTOXYETHOXY)-ETOH, TRIPROPYLENE GLYCOL MONOMETHYL ETHER, METHYL FORMATE, ETHYL FORMATE, N-PROPYL FORMATE, ETHYL ACETATE, METHYL PROPIONATE, N-BUTYL FORMATE, ETHYL PROPIONATE, ISOPROPYL ACETATE, METHYL BUTYRATE, METHYL ISOBUTYRATE, PROPYL ACETATE, N-BUTYL ACETATE, ETHYL BUTYRATE, ISOBUTYL ACETATE, METHYL PIVALATE, N-PROPYL PROPIONATE, S-BUTYL ACETATE, T-BUTYL

ACETATE, BUTYL PROPIONATE, AMYL ACETATE, N-PROPYL BUTYRATE, N-BUTYL BUTYRATE, ISOBUTYL ISOBUTYRATE, N-HEXYL ACETATE, 2-METHYLPENTYL ACETATE, 3-METHYLPENTYL ACETATE, 4-METHYLPENTYL ACETATE, 2, 3-DIMETHYLBUTYL ACETATE, N-HEPTYL ACETATE, 2-METHYLHEXYL ACETATE, 3-METHYLHEXYL ACETATE, 4-METHYLHEXYL ACETATE, 5-METHYLHEXYL ACETATE, 3-ETHYLPENTYL ACETATE, 2,4-DIMETHYLPENTYL ACETATE, ISOAMYL ISOBUTYRATE, N-OCTYL ACETATE, 2-ETHYL-HEXYL ACETATE, 3, 4-DIMETHYLHEXYL ACETATE, 3, 5-DIMETHYLHEXYL ACETATE, 3-ETHYLHEXYL ACETATE, 4-METHYLHEPTYL ACETATE, 4, 5-DIMETHYLHEXYL ACETATE, 5-METHYLHEPTYL ACEATE, 3-METHYLHEPTYL ACEATE, 2,4-DIMETHYLHEXYL ACETATE, N-NONYL ACETATE, 2-METHYLOCTYL ACETATE, 4-METHYLOCTYL ACETATE, 5-METHYLOCTYL ACETATE, 3-ETHYLHEPTYL ACETATE, 3, 6-DIMETHYLHEPTYL ACETATE, 3, 5-DIMETHYLHEPTYL ACETATE, 4, 5-DIMETHYLHEPTYL ACETATE, 4, 6-DIMETHYLHEPTYL ACETATE, 2,4-DIMETHYLHEPTYL ACETATE, 2, 3-DIMETHYLHEPTYL ACETATE, 2, 5-DIMETHYLHEPTYL ACETATE, 2, 3, 5-TEIMETHYLHEXYL ACETATE, 3, 6-DIMETHYLOCTYL ACETATE, 4, 6-DIMETHYLOCTYL ACETATE, 3-ISOPROPYLHEPTYL ACETATE, 4, 7-DIMETHYLNONYL ACETATE, 3, 5, 7-TRIMETHYLOCTYL ACETATE, 3-ETHYL-6-METHYLOCTYL ACETATE, 3, 6, 8-TRIMETHYLNONYL ACETATE, 3, 5, 7-TRIMETHYLNONYL ACETATE, 2, 3, 5, 7-TETRAMETHYLOCTYL ACETATE, 2, 4, 6, 8-TETRAMETHYLNONYL ACETATE, 4, 7, 9-TRIMETHYLDECYL ACETATE, 3-ETHYL-6, 7-DIMETHYLNONYL ACETATE, 5-ETHYL-3, 6, 8-TRIMETHYLNONYL ACETATE, 2, 3, 5, 6, 8-PENTAAMETHYLNONYL ACETATE, DIMETHYL CARBONATE, PROPYLENE CARBONATE, METHYL LACTATE, ETHYL LACTATE, 2-METHOXYETHYL ACETATE, METHYL ISOPROPYL CARBONATE, 2-METHYOXY-1-PROPYL ACETATE, 2-ETHOXYETHYL ACETATE, 1-METHOXY-2-PROPYL ACETATE, DIMETHYL SUCCINATE, ETHYLENE GLYCOL DIACETATE, ETHYL 3-ETHOXY PROPIONATE, DIISOPROPYL CARBONATE, DIMETHYL GLUTARATE, 2-BUTOXYETHYL ACETATE, DIMETHYL ADIPATE, SUBSTITUTED C7 ESTER (C12), TEXANOL ISOMERS, 3-HYDROXY-2, 2, 4-TRIMETHYLPENTYL-1-ISOBUTYRATE, 1-HYDROXY-2, 2, 4-TRIMETHYLPENTYL-3-ISOBUTYRATE, SUBSTITUTED C9 ESTER (C12), ETHYLENE OXIDE, PROPYLENE OXIDE, 1, 2-EPOXYBUTANE, FORMIC ACID, ACETIC ACID, ACRYLIC ACID, PROPIONIC ACID, METHYL ACRYLATE, VINYL ACETATE, 2-METHYL-2-BUTENE-3-OL, ETHYL ACRYLATE, METHYL METHACRYLATE, BUTYL METHACRYLATE, ISOBUTYL METHACRYLATE, FURAN, FORMALDEHYDE, ACETALDEHYDE, PROPIONALDEHYDE, BUTANAL, 2-METHYLPROPANAL, C4 ALDEHYDES, PENTANAL (VALERALDEHYDE), 2, 2-DIMETHYLPROPANAL (PIVALDEHYDE), 3-METHYLBUTANAL (ISOVALERALDEHYDE), C5 ALDEHYDES, GLUTARALDEHYDE, HEXANAL, C6 ALDEHYDES, HEPTANAL, C7 ALDEHYDES, OCTANAL, C8 ALDEHYDES, GLYOXAL, METHYL GLYOXAL, ACROLEIN, CROTONALDEHYDE, METHACROLEIN, HYDROXY METHACROLEIN, CYCLOBUTANONE, METHYL ETHYL KETONE, CYCLOPENTANONE, C5 CYCLIC KETONES, 3-PENTANONE, C5 KETONES, 2-PENTANONE, CYCLOHEXANONE, C6 CYCLIC KETONES, C6 KETONES, 4-METHYL-2-PENTANONE, METHYL N-BUTYL KETONE, METHYL T-BUTYL KETONE, C7 CYCLIC KETONES, 2-METHYL-3-HEXANONE, 2-HEPTANONE, DI-ISOPROPYL KETONE, C7 KETONES, C8 CYCLIC KETONES, 2-OCTANONE, C8 KETONES, C9 CYCLIC KETONES, 2-NONANONE, DI-ISOBUTYL KETONE (2, 6-DIMETHYL-4-HEPTANONE), C9 KETONES, C10 CYCLIC KETONES, 2-DECANONE, C10 KETONES, BIACETYL, METHYLVINYL KETONE, HYDROXY ACETONE, METHOXY ACETONE, DIACETONE ALCOHOL, PHENOL, ALKYL PHENOLS, M-CRESOL, O-CRESOL, P-CRESOL, NITROBENZENE, PARA TOLUENE ISOCYANATE, METHYLENE DIPHENYLENE DIISOCYANATE, DIMETHYL AMINE, ETHYL AMINE, TRIMETHYL AMINE, ETHANOLAMINE, DIMETHYLAMINOETHANOL, DIETHANOL AMINE, TRIETHANOLAMINE, N-METHYL-2-PYRROLIDONE, METHYL CHLORIDE, VINYL CHLORIDE, ETHYL CHLORIDE, METHYL BROMIDE, 1, 1-DICHLOROETHANE, 1, 2-DICHLOROETHANE, ETHYL BROMIDE, CHLOROFORM, N-PROPYL BROMIDE, 1, 1, 2-TRICHLOROETHANE, N-BUTYL BROMIDE, 1, 2-DIBROMOETHANE, TRANS-1, 2-DICHLOROETHENE, 2-(CL-METHYL)-3-CL-PROPENE, TRICHLOROETHYLENE, MONOCHLOROBENZENE, BENZOTRIFLUORIDE, P-DICHLOROBENZENE, P-TRIFLUOROMETHYL-CL-BENZENE, BASE ROG MIXTURE, TLEV EXHAUST RFA, TLEV EXHAUST PHASE 2, TLEV EXHAUST LPG, TLEV EXHAUST CNG, TLEV EXHAUST E-85, TLEV EXHAUST M-85, FINAL LEV RFA, FINAL LEV PHASE 2, MINERAL SPIRITS D (TYPE II-C), MINERAL SPIRITS A (TYPE I-B, 91% ALKANES), MINERAL SPIRITS B (TYPE II-C), MINERAL SPIRITS C (TYPE II-C), EXXON EXXOL® D95 FLUID, EXXON ISOPAR® M FLUID, OXO-HEXYL ACETATE, OXO-HEPTYL ACETATE, OXO-OCTYL ACETATE, OXO-NONYL ACETATE, OXO-DECYL ACETATE, OXO-DODECYL ACETATE, OXO-TRIDECYL ACETATE

List 1: VOCs.

In one example, the first analyte is an explosive compound, for example a nitrogen-explosive compound. Nitrogen-explosive compounds may be classified under three structural categories: (i) nitroaromatic compounds; (ii) nitrate esters; and (iii) nitrammnes. Examples of nitrosubstituted hydrocarbons are nitromethane, trinitrobenzene (TNB), trinitrotoluene (TNT) and pentantiroaniline. Nitroglycerine (NG), ethylene glycol dinitrate (EGDN) and pentaerythritol tetranitrate (PETN) are nitrate esters. A list of the typical nitrogen-containing explosives is given in Table 1.

In one example, the set of analytes comprises N analytes, where N is a natural number greater than 1, for example 2, 5, 10, 20, 50, 100, 200, 500 or more. In one example, the set of analytes comprises N explosive compounds selected from Table 1. In one example, the set of analytes comprises all the explosive compounds selected from Table 1.

TABLE 1

Explosive compounds.

| Compound name | Abbreviation | Formula | Class | CAS no. | Vapor pressure |
|---|---|---|---|---|---|
| Cyclotrimethylene trinitramine | RDX | $C_3H_6N_6O_6$ | Nitramine | 121-82-4 | Low |
| Cyclotetramethylene tetranitramine | HMX | $C_4H_8N_8O_8$ | Nitramine | 2691-41-0 | Low |
| 2-Nitrotoluene | 2-NT | $C_7H_7NO_2$ | Nitraromatic | 88-72-2 | High |
| 3-Nitrotoluene | 3-NT | $C_7H_7NO_2$ | Nitraromatic | 99-08-1 | High |
| 4-Nitrotoluene | 4-NT | $C_7H_7NO_2$ | Nitraromatic | 99-99-0 | High |
| 2,3-Dinitrotoluene | 2,3-DNT | $C_7H_6N_2O_4$ | Nitroaromatic | 602-01-7 | High |
| 2,4-Dinitrotoluene | 2,4-DNT | $C_7H_6N_2O_4$ | Nitroaromatic | 121-14-2 | High |
| 2,5-Dinitrotoluene | 2,5-DNT | $C_7H_6N_2O_4$ | Nitroaromatic | 619-15-8 | High |
| 2,6-Dinitrotoluene | 2,6-DNT | $C_7H_6N_2O_4$ | Nitroaromatic | 606-20-2 | Low |
| 2,4,6-Trinitrotoluene | TNT | $C_7H_5N_3O_6$ | Nitroaromatic | 118-96-7 | Moderate-low |
| Nitroglycerine | NG | $C_3H_5N_3O_9$/ $CH_2(ONO_2)$—$CH(ONO_2)$—$CH_2(ONO_2)$ | Nitrate ester | 55-63-0 | High |
| Pentaerythritol tetranitrate | PETN | $C_5H_8N_4O_{12}$/$C(CH_2ONO_2)_4$ | Nitrate ester | 78-11-5 | Low |
| Ethylene glycol dinitrate | EGDN | $C_2H_4N_2O_6$/$NO_2$—$OCH_2CH_2O$—$NO_2$ | Nitrate ester | 628-96-6 | High |

In one example, the first analyte comprises and/or is a biohazard or a chemical weapon, for example dimethyl methylphosphonate (DMMP).

In one example, the first analyte is a semi-volatile compound. Generally, the term 'semi-volatile compounds' refers to organic compounds that possess Henry's law constants (H) in the range of $10^{-5}$ —$3 \times 10^{-7}$ atm·m$^3$/mol and demonstrate higher boiling points, usually greater than that of water with correspondingly low vapor pressure from $10^{-14}$-$10^{-4}$ atm. The H range is defined as volatility from liquid to air. For example, the 'semi-volatile' contaminant grouping is composed of compounds with broad chemical properties and structural features. Examples of semi-volatiles compounds include hydrocarbons, aldehydes, ethers, esters, phenols, organic acids, ketones, amines, amides, nitroaromatics, polychlorinated biphenyls (PCBs) (also known as Aroclors), polycyclic aromatic hydrocarbons (PAHs), phthalate esters, nitrosamines, halo ethers and trihalomethanes.

In one example, the set of analytes comprises N analytes, where N is a natural number greater than 1, for example 2, 5, 10, 20, 50, 100, 200, 500 or more. In one example, the set of analytes comprises N semi-volatile compounds, as exemplified above. In one example, the set of analytes comprises all the semi-volatile compounds, as exemplified above.

In one example, the first analyte is an emission compound and/or a greenhouse gas, for example as defined by European Environment Agency EEA) Indicator Assessment IND-112-en (published 22 Nov. 2018) such as CO, $NH_3$, NMVOCs, $SO_x$ and $NO_x$, as defined by EEA IND-366-en (published 16 Oct. 2018) such as sulphur dioxide/oxides ($SO_2$/$SO_x$), nitrogen oxides ($NO_x$), non-methane volatile organic compounds (NMVOCs) and ammonia ($NH_3$) and/or as defined by IND-2-en (published 20 Mar. 2019) including greenhouse gases included in the Kyoto Protocol (KPG) (carbon dioxide ($CO_2$), methane ($CH_4$), nitrous oxide ($N_2O$), and three (groups of) fluorinated gases (HFC, PFC, $SF_6$); greenhouse gases in the Montreal Protocol (MPG) cover three other groups of fluorinated gases: CFCs, HCFCs and $CH_3CCl_3$; and in addition, other forcing agents and greenhouse gases that are not included in global treaties but are dealt with at a regional level (e.g. under the UNECE Convention on Long Range Transboundary Air Pollution), here called non-protocol gases (NPG), including tropospheric ozone ($O_3$), aerosols such as black carbon, sulphate and water vapour.

In one example, the set of analytes comprises N analytes, where N is a natural number greater than 1, for example 2, 5, 10, 20, 50, 100, 200, 500 or more. In one example, the set of analytes comprises N emission compounds and/or a greenhouse gases, as exemplified above. In one example, the set of analytes comprises all the emission compounds and/or a greenhouse gases, as exemplified above.

In one example, the set of analytes comprises N analytes, where N is a natural number greater than 1, for example 2, 5, 10, 20, 50, 100, 200, 500 or more. In one example, the set of analytes comprises N analytes selected from VOCs, explosive compounds, biohazards, chemical weapons, semi-volatile compounds, emission compounds and/or greenhouse gases, as described above i.e. mixtures of these analytes. For example, detecting of analytes in outdoor air may include sensing a mixture of emission compounds, greenhouse gases, semi-volatile compounds and VOCs.

Comparing

In one example, the controller is arranged to compare the first response with a set of reference responses and optionally match the first response with a first reference response of the set of reference responses. In this way, the first analyte may be identified, by comparison and optionally matching the first response with the first reference response i.e. library matching. In one example, the controller comprises the set of reference responses.

Baseline Response

In one example, the detector is arranged to obtain a first baseline response of a set of baseline responses at the zeroth temperature, pressure ($T_0$, $P_0$) and wherein the controller is arranged to modify the first response based, at least in part, on the obtained first baseline response. In this way, the first response may be corrected for drift of the sensor, for example. Particularly, while the sensor may drift with time, temperature and/or pressure, obtaining (i.e. sensing) the first baseline response prior, preferably immediately prior, to changing the zeroth temperature, pressure ($T_0$, $P_0$) to the first temperature, pressure ($T_1$, $P_1$) reduces an effect of the drift.

Heater Cooler

In one example, the detector comprises a heater and/or cooler arranged to heat and/or cool the first sorbent and/or the sorbed first analyte to the first temperature, pressure ($T_1$, $P_1$). In one example, the heater is arranged to heat the first gas, for example a heated surface such as heater coil in a flow path of the first gas and/or an infrared (IR) source, thereby indirectly heating the first sorbent and causing desorption of the sorbed first analyte therefrom. In one example, the heater is arranged to heat (i.e. directly) the first sorbent, thereby directly heating the first sorbent and causing desorption of the sorbed first analyte therefrom. In one example, the cooler is arranged to cool the first gas, for example a cooled surface such as chiller coil in a flow path of the first gas, thereby indirectly cooling the first sorbent and causing sorption, preferably adsorption, of the first analyte therein and/or thereon. In one example, the cooler is arranged to cool (i.e. directly) the first sorbent, thereby directly cooling the first sorbent and causing sorption of the first analyte therein and/or thereon.

In one example, the detector comprises a cooler arranged to cool the first sorbent to the zeroth temperature.

In one example, the heater is thermally coupled to the first sorbent, preferably in contact therewith. In one example, the heater comprises a resistive heater, for example a heater wire such as a Pt heater wire or track, provided on and/or in the first sorbent, for example on a reverse surface thereof. It should be understood that the reverse surface is opposed to a surface of the first sorbent exposed to the first gas. In one example, the cooler is thermally coupled to the first sorbent, preferably in contact therewith. In one example, the cooler comprises a chiller coil provided on and/or in the first sorbent, for example on a reverse surface thereof. In one example, the detector comprises a Peltier heater/cooler thermally coupled to the first sorbent, preferably in contact therewith.

In one example, the detector comprises a heatsink, for example thermally coupled to the heater and/or cooler.

In one example, the controller is arranged to change the zeroth temperature, pressure ($T_0$, $P_0$) to the first temperature, pressure ($T_1$, $P_1$) according to a first survey equation of a set of survey equations, before changing the zeroth temperature, pressure ($T_0$, $P_0$) to the first temperature, pressure ($T_1$, $P_1$) according to the first equation. That is, the first survey equation may provide responses from a rapid scan of the analytes included in the first gas and the first equation may be selected according to the included analytes and/or according to respective concentrations of the included analytes.

In one example, the detector comprises a pump arranged to flow the first gas across and/or through the first sorbent. In this way, a flow rate of the first gas across and/or through the first sorbent may be controlled, thereby providing active sorption and/or desorption. For example, during sorption, the flow rate of the first gas across and/or through the first sorbent may be relatively higher while during desorption, so as to increase an amount of the first analyte exposed to the first sorbent. In contrast, when sensing the first analyte, the flow rate of the first gas may be relatively lower or even stilled (i.e. no flow), so as to increase a value of the first response, since the desorbed analyte is less or not diluted by flowing first gas.

In one example, a flow rate of the first gas is in a range from 0 (i.e. no flow or no active flow) to 10 SLM, preferably in a range from 0.0001 to 2 SLM, more preferably in a range from 0.0005 to 1 SLM, for example 0.05 SLM.

In one example, the detector does not comprise a pump arranged to flow the first gas across and/or through the first sorbent. In other words, flow of the first gas across and/or through the first sorbent is not controlled by the detector, thereby providing passive sorption and/or desorption. For example, flow of the first gas across and/or through the first sorbent may be according to ambient conditions. In this way, the detector comprises fewer components, particularly moving components, reducing cost, complexity and/or size thereof while increasing robustness.

In one example:
- the first sorbent is for sorbing, preferably adsorbing, therein and/or thereon, a second analyte of the set of analytes included in the first gas of a set of gases exposed thereto, at the zeroth temperature, pressure ($T_0$, $P_0$);
- the controller is arranged to change the first temperature, pressure ($T_1$, $P_1$) to a second temperature, pressure ($T_2$, $P_2$) of the set of temperatures, pressures ($T$, $P$) according to a second equation of the set of equations, to desorb at least some of the sorbed, preferably adsorbed, second analyte from the first sorbent;
- the detector is arranged to detect at least some of the desorbed second analyte and to output a second response of the set of responses corresponding to the sensed second analyte;
- wherein the second response comprises and/or is a first characteristic response of a set of characteristic responses of the second analyte.

In this way, both the first analyte and the second analyte are detected by the detector. Since the respective responses of the first analyte and the second analyte are characteristic thereof, the first analyte and the second analyte may be distinguished. Note that the pressure and/or the temperature may remain constant or not controlled, as discussed previously. In one example, $P_0 \approx P_1 \approx P_2$ and $T_0 < T_1 \geq T_2$. In one example, $P_0 \approx P_1 \approx P_2$ and $T_0 > T_1 \geq T_2$. In one example, $P_0 > P_0 \geq P_0$ and $T_0 \approx T_1 \approx T_2$. In one example, $P_0 < P_0 \approx P_0$ and $T_0 \approx T_1 \approx T_2$.

Housing

In one example, the detector comprises a housing, comprising a chamber arranged to receive the first gas therein, wherein the first sorbent and the sensor are in fluid communication with the chamber. In one example, the housing comprises a gas inlet and/or a gas outlet respectively in fluid communication with the chamber, for example via respective passageways. In one example, the first sorbent and/or the sensor are coupled to the housing, for example using seals such as O-rings, to seal the first sorbent and/or the sensor against the housing such that gas flow is restricted to a path defined by the gas inlet and the gas outlet via the chamber and/or such that gas is contained within the chamber. In one example, the housing is an open housing, thereby exposing the first sorbent and/or the sensor directly to ambient first gas, for example air.

In one example, the first sorbent is arranged relatively proximal to the sensor, for example confronting the sensor, so as to reduce a volume (i.e. a dead volume) between the first sorbent and the sensor. In one example, the first sorbent and the sensor are fluidically coupled via a capillary or a tube, so as to reduce a volume (i.e. a dead volume) between the first sorbent and the sensor. In one example, a volume (i.e. a dead volume) between the first sorbent and the sensor is at most 500 ml, preferably at most 50 ml, more preferably at most 10 ml, even more preferably at most 1 ml, most preferably at most 0.1 ml.

Method

The second aspect provides a method of detecting analytes in gases, comprising: exposing a first sorbent of a set of sorbents, preferably wherein the first sorbent comprises and/or is an adsorbent, to a first gas of a set of gases, at a zeroth temperature, pressure ($T_0$, $P_0$) of a set of temperatures, pressures (T, P);

sorbing, preferably adsorbing, by the first sorbent, therein and/or thereon, and/or desorbing therefrom, a first analyte of a set of analytes included in the first gas;

desorbing and/or sorbing at least some of the first analyte by controlling a change from the zeroth temperature, pressure ($T_0$, $P_0$) to a first temperature, pressure ($T_1$, $P_1$) of the set of temperatures, pressures (T, P) according to a first equation of a set of equations; and sensing at least some of the first analyte and outputting a first response of a set of responses corresponding to the sensed first analyte;

wherein the first response comprises and/or is a first characteristic response of a set of characteristic responses of the first analyte.

The exposing, the first sorbent, the set of sorbents, the first gas, the set of gases, the zeroth temperature, pressure ($T_0$, $P_0$), the set of temperatures, pressures (T, P), the first analyte, the set of analytes, the desorbing, the sorbing, the change from the zeroth temperature, pressure ($T_0$, $P_0$) to the first temperature, pressure ($T_1$, $P_1$), the first temperature, pressure ($T_1$, $P_1$), the first equation, the set of equations, the sensing, the first response, the set of responses, the first characteristic response and/or the set of characteristic responses of the first analyte may be as described with respect to the first aspect.

In one example, the method comprises:

exposing the first sorbent, preferably wherein the first sorbent comprises and/or is the adsorbent, to the first gas at the zeroth temperature, pressure ($T_0$, $P_0$);

sorbing, preferably adsorbing, by the first sorbent thereon, the first analyte;

desorbing at least some of the first analyte by controlling the change from the zeroth temperature, pressure ($T_0$, $P_0$) to the first temperature, pressure ($T_1$, $P_1$) according to the first equation by heating from $T_0$ to $T_1$ (i.e. $T_1$ is greater than $T_0$) and/or by reducing pressure from $P_0$ to $P_1$ (i.e. $P_1$ is less than $P_0$); and sensing at least some of the first analyte and outputting the first response;

wherein the first response comprises and/or is the first characteristic response of the first analyte.

In other words, this is the first mode of operation, as described with respect to the first aspect.

In one example, the method comprises:

exposing the first sorbent, preferably wherein the first sorbent comprises and/or is the adsorbent, to the first gas at the zeroth temperature, pressure ($T_0$, $P_0$);

sorbing, preferably adsorbing, at least some of the first analyte by controlling the change from the zeroth temperature, pressure ($T_0$, $P_0$) to the first temperature, pressure ($T_1$, $P_1$) according to the first equation by cooling from $T_0$ to $T_1$ (i.e. $T_1$ is less than $T_0$) and/or increasing the pressure from $P_0$ to $P_1$ (i.e. $P_1$ is greater than $P_0$); and sensing at least some of the first analyte and outputting the first response;

wherein the first response comprises and/or is the first characteristic response of the first analyte.

In other words, this is the second mode of operation, as described with respect to the first aspect.

In one example, the method comprises comparing the first response with a set of reference responses and optionally matching the first response with a first reference response of the set of reference responses.

In one example, the method comprises obtaining at least a part of the set of reference responses, for example by detecting respective first responses from a first analyte at a plurality of concentrations for a particular first gas for the same first equation (i.e. under the same conditions) and/or for example by detecting respective first responses from a first analyte at a same of concentrations for a particular first gas for different first equation (i.e. under different conditions). In this way, a reference library may be provided.

In one example, the method comprises obtaining a first baseline response of a set of baseline responses at the zeroth temperature, pressure ($T_0$, $P_0$) and modifying the first response based, at least in part, on the obtained first baseline response.

In one example, the method comprises controlling only the change the zeroth temperature ($T_0$) to the first temperature, pressure ($T_1$).

In one example, the method comprises controlling only the change from the zeroth pressure ($P_0$) to the first pressure ($P_1$).

In one example, the method comprises changing the zeroth temperature, pressure ($T_0$, $P_0$) to the first temperature, pressure ($T_1$, $P_1$) according to a first survey equation of a set of survey equations, before changing the zeroth temperature, pressure ($T_0$, $P_0$) to the first temperature, pressure ($T_1$, $P_1$) according to the first equation.

In one example, the method comprises cooling the first sorbent to the zeroth temperature.

In one example, the method comprises flowing the first gas across and/or through the first sorbent.

In one example, the method comprises: sorbing, preferably adsorbing, by the first sorbent, therein and/or thereon, a second analyte of the set of analytes included in the first gas of a set of gases exposed thereto, at the zeroth temperature, pressure ($T_0$, $P_0$);

desorbing at least some of the sorbed, preferably adsorbed, second analyte from the first sorbent by changing the first temperature, pressure ($T_1$, $P_1$) to a second temperature, pressure ($T_2$, $P_2$) of the set of temperatures, pressures (T, P) according to a second equation of the set of equations; and sensing at least some of the desorbed second analyte and outputting a second response of the set of responses corresponding to the sensed second analyte;

wherein the second response comprises and/or is a first characteristic response of a set of characteristic responses of the second analyte.

In one example, the method comprises:

sorbing, preferably adsorbing, by the first sorbent, therein and/or thereon, and/or desorbing therefrom, N analytes of a set of analytes included in the first gas;

desorbing and/or sorbing at least some of the N analytes by controlling the change from the zeroth temperature, pressure ($T_0$, $P_0$) to the first temperature, pressure ($T_1$, $P_1$) of the set of temperatures, pressures (T, P) according to the first equation of the set of equations, optionally by controlling the change from the zeroth temperature, pressure ($T_0$, $P_0$) to M temperatures, pressures ($T_M$, $P_M$) of the set of temperatures, pressures (T, P) according to P equations respectively of the set of equations; and sensing at least some of the N analytes and outputting N responses of a set of responses corresponding to the sensed N analytes;

wherein the N responses comprise and/or are N characteristic responses of the set of characteristic responses of the N analytes;

wherein M, N and P are independently or dependently natural number greater than 1 for example 2, 3, 4, 5, 6, 7, 8, 9, 10, 50, 100, 500, 1000 or more.

In other words, the method may be for detecting N analytes included in the first gas. The N analytes may be as described with respect to the first aspect.

Use

The third aspect provides use of microporous and/or mesoporous silica, a zeolite, activated carbon and/or a metal organic framework, MOF, as an adsorbent for an analyte in a detector. The use, the microporous and/or mesoporous silica, a zeolite, activated carbon and/or a metal organic framework, MOF, the adsorbent, the analyte and/or the detector may be as described with respect to the first aspect.

The fourth aspect provides use of temperature ramping to selectively adsorb or desorb an analyte, respectively to or from an adsorbent in a detector. The use, the microporous and/or mesoporous silica, a zeolite, activated carbon and/or a metal organic framework, MOF, the adsorbent, the analyte and/or the detector may be as described with respect to the first aspect.

Definitions

Throughout this specification, the term "comprising" or "comprises" means including the component(s) specified but not to the exclusion of the presence of other components.

The term "consisting essentially of" or "consists essentially of" means including the components specified but excluding other components except for materials present as impurities, unavoidable materials present as a result of processes used to provide the components, and components added for a purpose other than achieving the technical effect of the invention, such as colourants, and the like.

The term "consisting of" or "consists of" means including the components specified but excluding other components.

Whenever appropriate, depending upon the context, the use of the term "comprises" or "comprising" may also be taken to include the meaning "consists essentially of" or "consisting essentially of", and also may also be taken to include the meaning "consists of" or "consisting of".

The optional features set out herein may be used either individually or in combination with each other where appropriate and particularly in the combinations as set out in the accompanying claims. The optional features for each aspect or exemplary embodiment of the invention, as set out herein are also applicable to all other aspects or exemplary embodiments of the invention, where appropriate. In other words, the skilled person reading this specification should consider the optional features for each aspect or exemplary embodiment of the invention as interchangeable and combinable between different aspects and exemplary embodiments.

BRIEF DESCRIPTION OF THE FIGURES

For a better understanding of the invention, and to show how exemplary embodiments of the same may be brought into effect, reference will be made, by way of example only, to the accompanying diagrammatic Figures, in which.

DETAILED DESCRIPTION OF VARIOUS EMBODIMENTS

Figure 1:
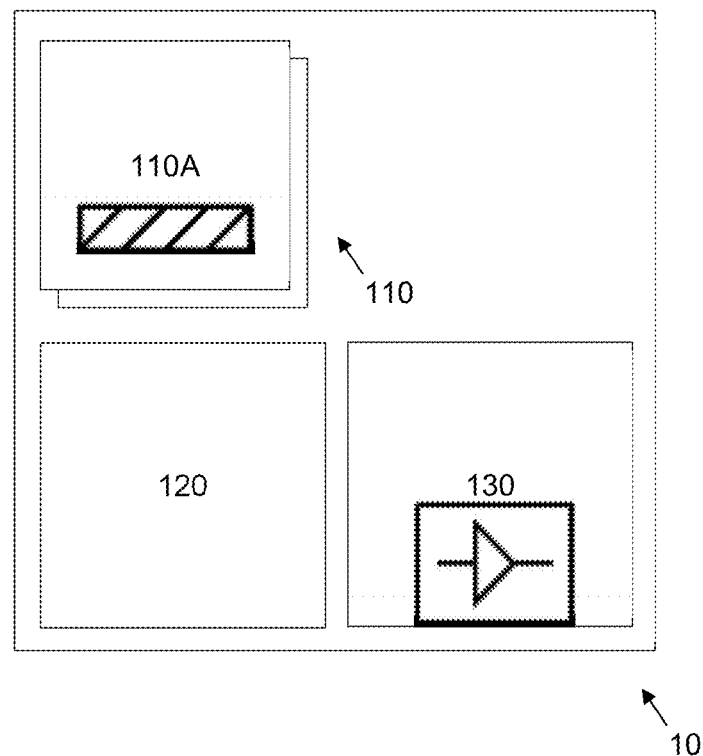
FIG. 1 schematically depicts a detector according to an exemplary embodiment.

FIG. 1 schematically depicts a detector 10 according to an exemplary embodiment. The detector 10 is for detecting analytes in gases. The detector 10 comprises a first sorbent 110A of a set of sorbents 100, preferably wherein the first sorbent 110A comprises and/or is an adsorbent, for sorbing, preferably adsorbing, therein and/or thereon and/or desorbing therefrom, a first analyte of a set of analytes included in a first gas of a set of gases exposed thereto, at a zeroth temperature, pressure ($T_0$, $P_0$) of a set of temperatures, pressures (T, P). The detector 10 comprises a controller 120 arranged to change the zeroth temperature, pressure ($T_0$, $P_0$) to a first temperature, pressure ($T_1$, $P_1$) of the set of temperatures, pressures (T, P) according to a first equation of a set of equations, to desorb and/or sorb at least some of the first analyte. The detector 10 comprises a sensor 130 arranged to sense at least some of the first analyte and to output a first response of a set of responses corresponding to the sensed first analyte; wherein the first response comprises and/or is a first characteristic response of a set of characteristic responses of the first analyte.

The detector 10 may be as described above with respect to the first aspect.

Figure 2:
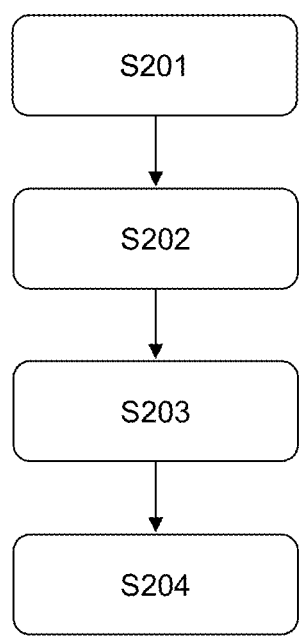
FIG. 2 schematically depicts a method according to an exemplary embodiment.

FIG. 2 schematically depicts a method according to an exemplary embodiment. The method is of detecting analytes in gases.

At S201, a first sorbent of a set of sorbents, preferably wherein the first sorbent comprises and/or is an adsorbent, is exposed to a first gas of a set of gases, at a zeroth temperature, pressure ($T_0$, $P_0$) of a set of temperatures, pressures (T, P).

At S202, the first sorbent sorbs, preferably adsorbs, therein and/or thereon, and/or desorbs therefrom, a first analyte of a set of analytes included in the first gas.

At S203, at least some of the first analyte is desorbed and/or sorbed by controlling a change from the zeroth temperature, pressure ($T_0$, $P_0$) to a first temperature, pressure ($T_1$, $P_1$) of the set of temperatures, pressures (T, P) according to a first equation of a set of equations.

At S204, at least some of the first analyte is sensed and a first response of a set of responses corresponding to the sensed first analyte is output. The first response comprises and/or is a first characteristic response of a set of characteristic responses of the first analyte.

The method may be as described above with respect to the second aspect.

Experimental

Introduction

The challenge of many sensors for airborne explosive is the accurate detection of extremely low concentrations. A goal of this work is to test nanoporous material (i.e. a first sorbent) as a pre-concentrator for a commercially available sensor and to measure the improvement in the sensitivity. For this purpose, a PID sensor is used; however, similar improvements could be assumed for other sensors.

This work details a method of using a detector comprising the nanoporous material to enhance the sensitivity of a PID sensor, which is a broadband VOC sensor. The temperature of the porous material is lowered to enhance the VOCs adsorption from a gas flow onto the material. The temperature is then raised up to desorb all the adsorbed VOCs at the same time, leading to a peak (i.e. a first response) in the concentration in the proximity of the nanoporous material. The size and/or shape of this peak can then be analysed to determine the concentration and/or identity of the VOC.

This method is found to give a gain of 50 to 70 times the steady-state change in signal of the sensor. This method has a further advantage that the zero point of the sensor is not required. This means that drifts in the zero point over the lifetime of the sensor do not lead to measurement errors. The shape of the peak also depends on the particular VOC, indicating that it should be possible to perform some degree of classification.

The detector comprises the porous material that acts as a VOC storage medium, the PID sensor, a Peltier heater/cooler and Peltier controller to set the temperature of the porous material. The temperature control is coordinated by a controller with the measurements from the sensor which also relates the update rate of the sensor to the time constants associated with adsorbing/desorbing the VOC and storing enough VOC to enhance the gain.

This work starts with an overview of the method, the analysis of the data and the detector. The effects of concentration for two different VOCs (limonene and IPA) are compared to a more traditional use of the sensor to demonstrate the gain in sensitivity.

The effect of the time spent gathering VOCs is also tested showing that the technique does eventually saturate at long enough dwell times. A slower increase in temperature demonstrates that VOCs have different response characteristics which might be used for VOC classification.

Description of Measurement Process

A constant flow of gas containing a VOC (i.e. a first analyte of a set of analytes included in a first gas of a set of gases) is passed through a chamber containing a porous media on a Peltier heater/cooler and a broadband VOC PID sensor. In this report the first sorbent is porous silica etched into a silicon wafer and the VOC sensor is an Alphasense PID-AH, available from Alphasense Limited (UK).

Charge Phase

During the charge phase, the first sorbent is exposed to the first analyte of the set of analytes included in the first gas of the set of gases, at a zeroth temperature, pressure ($T_0$, $P_0$) of a set of temperatures, pressures (T, P), thereby sorbing therein the first analyte.

In more detail, the temperature of the Peltier is dropped so that the VOCs can deposit (particularly, adsorb) on the porous media. It is expected that VOCs will continue to deposit until an equilibrium with the VOC concentration in the gas is reached. The constant flow through the chamber keeps the source concentration of VOC (nearly) constant. The quantity of VOC which deposits on the porous media should be related to the surface area of the porous media, the dwell time at this temperature, the concentration of the VOC in the carrier gas and the surface chemistry between the porous media and the VOC. In this report the same sample of porous material is used throughout, so the surface area and the surface chemistry (with respect to the different VOCs) is fixed.

Measure Phase

During the measure phase, the zeroth temperature, pressure ($T_0$, $P_0$) is changed to a first temperature, pressure ($T_1$, $P_1$) of the set of temperatures, pressures (T, P) according to a first equation of a set of equations, to desorb at least some of the first analyte.

The temperature is then increased to evaporate the VOCs from the porous media. If this evaporation takes place over a short period of time then the concentration of VOC in the chamber should peak well above the concentration of VOC in the carrier gas. This excess concentration will gradually be removed by the constant gas flow. The size and shape of the peak in concentration should depend on the quantity of VOC released from the porous media and the sensitivity of the VOC sensor to the particular VOC. The change in temperature should be as fast as possible so as to increase the peak concentration, as the continuous gas flow will start to remove the excess VOCs.

Ideally the VOC is entirely evaporated (desorbed from the nanoporous material) at this temperature to gain the maximum response. It is possible to check that this is the case by having a further increase in temperature—if the VOC has been completely evaporated then this second increase in temperature will not release any further VOCs and there will be no resulting peak in concentration. If classification of VOCs is desired rather than the absolute sensitivity then a series of levels could be used to determine the temperatures at which the VOC evaporates. An alternative approach to classification is to ramp the temperature gradually to measure at which temperatures the peak occurs.

Figure 3:
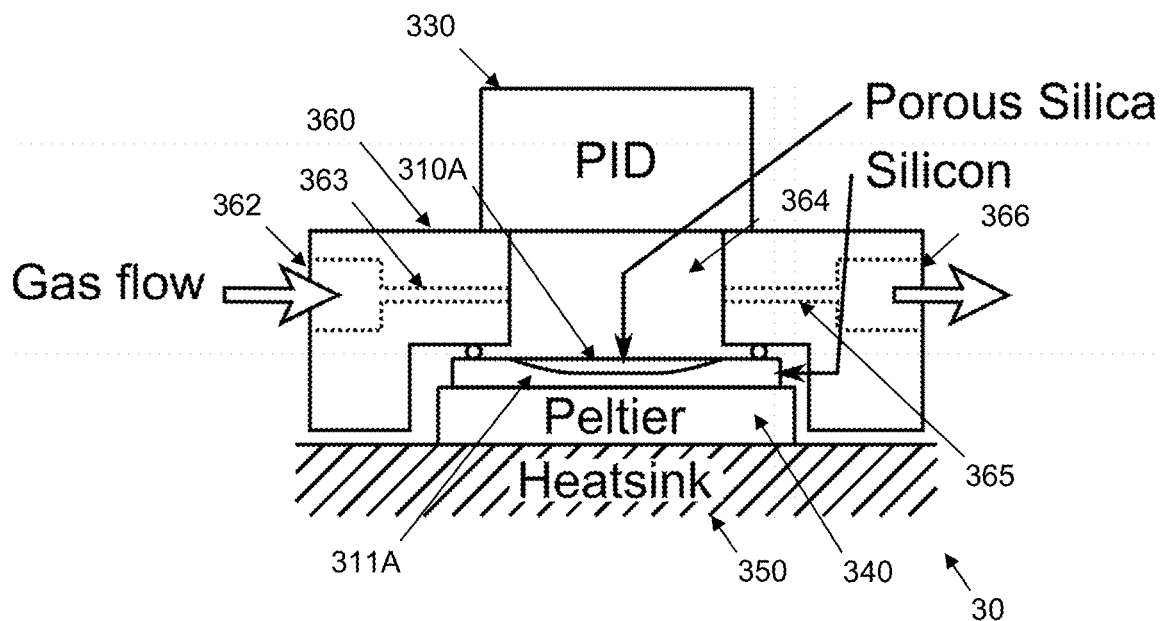
FIG. 3 schematically depicts a detector according to an exemplary embodiment.

FIG. 3 schematically depicts a detector 30 according to an exemplary embodiment. The detector 30 is for detecting analytes in gases. The detector 30 comprises a first sorbent 310A of a set of sorbents 300 (not shown), preferably wherein the first sorbent 310A comprises and/or is an adsorbent, for sorbing, preferably adsorbing, therein and/or thereon and/or desorbing therefrom, a first analyte of a set of analytes included in a first gas of a set of gases exposed thereto, at a zeroth temperature, pressure ($T_0$, $P_0$) of a set of temperatures, pressures (T, P). The detector 30 comprises a controller 320 (not shown) arranged to change the zeroth temperature, pressure ($T_0$, $P_0$) to a first temperature, pressure ($T_1$, $P_1$) of the set of temperatures, pressures (T, P) according to a first equation of a set of equations, to desorb and/or sorb at least some of the first analyte. The detector 30 comprises a sensor 330 arranged to sense at least some of the first analyte and to output a first response of a set of responses corresponding to the sensed first analyte; wherein the first response comprises and/or is a first characteristic response of a set of characteristic responses of the first analyte.

Figure 4:
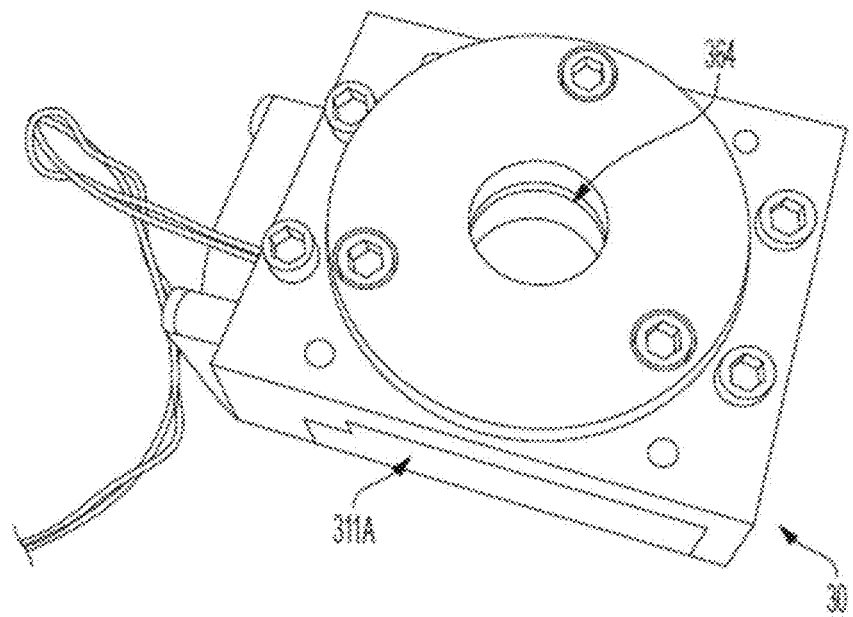
FIG. 4 shows a photograph of a detector according to an exemplary embodiment.

In more detail, the detector 30 comprises: a silicon wafer 311A with an etched and oxidised porous silica layer 310A to act as the concentrator (i.e. the first sorbent 310A), having a thickness of 50 μm and a porosity of about 50%; an Alphasense PID-AH sensor (i.e. the sensor 330) as the broadband VOC sensor; the controller 320 (as described below); a Peltier 340 (i.e. a heater/cooler) and heatsink 350 to control the temperature of the porous silica 310A; and a PEEK cell (i.e. a housing 360) to contain the gas flow and mount the PID 330, silicon 311A/porous silica wafer 310A and the Peltier 340 (FIGS. 3 and 4).

The PEEK cell comprises a gas inlet 362 in fluid communication with a cylindrical chamber 364 via an inlet passageway 363, extending radially therefrom, at a first end of the housing 360, and a gas outlet 366 in fluid communication with the chamber 364 via an outlet passageway 365, extending radially therefrom, at a second end of the housing 360, diametrically opposed to the first end of the housing 360. The first sorbent 310A and the sensor 330 are arranged at opposed ends of the cylindrical chamber 364, in fluid communication therewith. The housing 360 has a diameter of 1.5 cm and a height of 0.5 cm, such that a volume between the first sorbent 310A and the sensor 330 is about 0.88 ml. Seals, for example O-rings, seal the first sorbent 310A and the sensor 330 against the housing 360 such that gas flow is restricted to a path defined by the gas inlet 362 and the gas outlet 366 via the chamber 364.

The porous silica was fabricated from a boron-doped silicon wafer with a resistivity of 0.01-0.02 Ωcm and (100) crystal orientation. Silicon was electrochemically etched in a 1:1 mixture of 48% hydrofluoric acid and ethanol under a current density of 120 mA/cm$^2$, 288 cycles of 2 sec on 3 sec off. The sample was then thermally oxidised in a furnace under 50 sccm $O_2$ flow for 16 hours at a temperature of 800° C. The final sample was 50 μm thick and had about 50% porosity.

The gas was generated using an Owlstone Oven Vapour Generator, available from Owlstone Limited (UK), with a gas dilution rig to control the concentration and flowrate of the VOCs. This also provides a purge gas (99.99% $N_2$) containing no VOCs to help clear the sensor and to provide background readings. The gas flow was controlled to be 0.050 SLM.

The system is controlled by the controller via software which coordinates the detector, logs the measurements (i.e. responses) and analyses the results.

FIG. 3 schematically depicts a detector according to an exemplary embodiment. In more detail, FIG. 3 shows a cross-section of the detector comprising the porous media, Peltier and broadband VOC sensor.

FIG. 4 shows a photograph of a detector according to an exemplary embodiment. In more detail, FIG. 4 shows a photograph of the detector housing. The PID has been replaced with a glass window allowing an internal region of the cell to be seen.

Figure 5A:
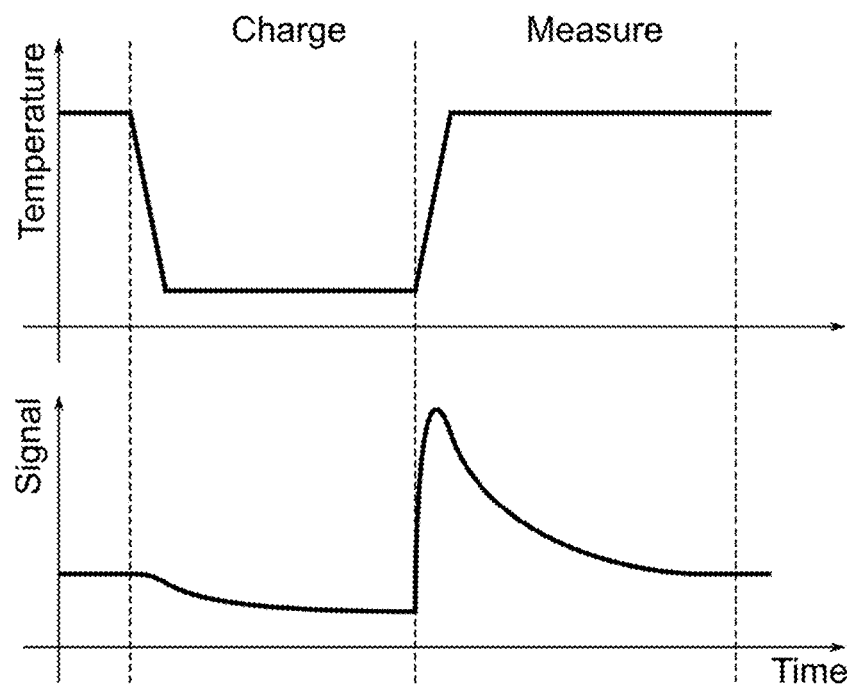
FIG. 5A shows a graph of temperature as a function of time and a corresponding graph of first response as a function of time for a detector and a method according to an exemplary embodiment.

FIG. 5A shows a graph of temperature as a function of time and a corresponding graph of first response as a function of time for a detector and a method according to an exemplary embodiment. In more detail, FIG. 5A is an illustration of the enhancement effect, as described above with respect to the first mode of operation. VOCs deposit from the gas flow onto the porous media during the charge phase when the temperature is low. During the measure phase the temperature is increased, releasing the VOCs and causing a peak in the VOC concentration (i.e. the first characteristic response), during the measure phase. This extra concentration is gradually removed by the gas flow.

Figure 5B:
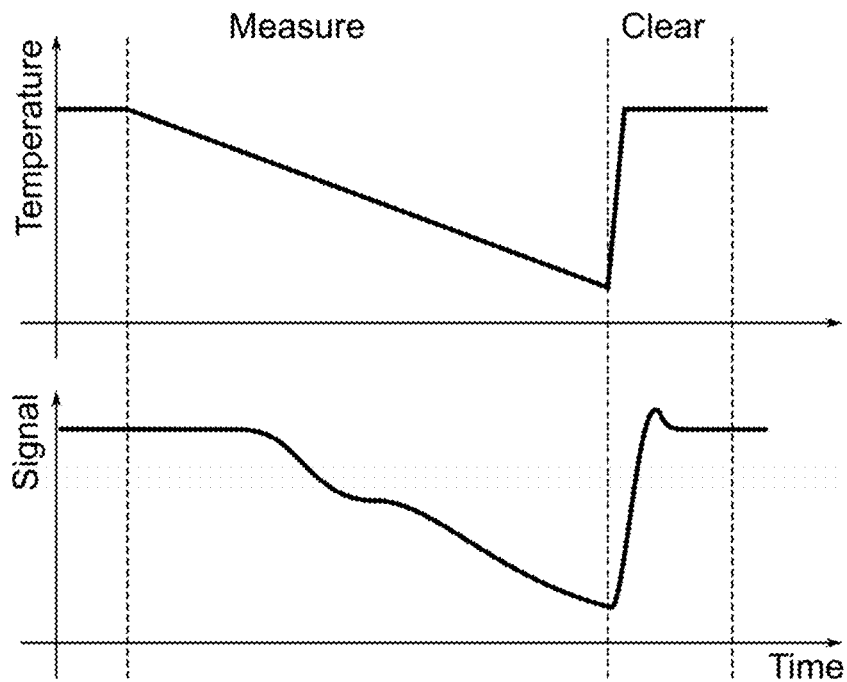
FIG. 5B shows a graph of temperature as a function of time and a corresponding graph of first response as a function of time for a detector and a method according to an exemplary embodiment.

FIG. 5B shows a graph of temperature as a function of time and a corresponding graph of first response as a function of time for a detector and a method according to an exemplary embodiment. In more detail, FIG. 5B is an illustration of the sorption effect, as described above with respect to the second mode of operation. Particularly, the first characteristic response is measured during the measure phase, during which the temperature is ramped linearly downwards relatively slowly. During the clear phase, the temperature is heated relatively quickly and a relatively small positive response is due to desorption of the relatively small amount of the first analyte sorbed in and/or on the first sorbent.

Figure 5C:
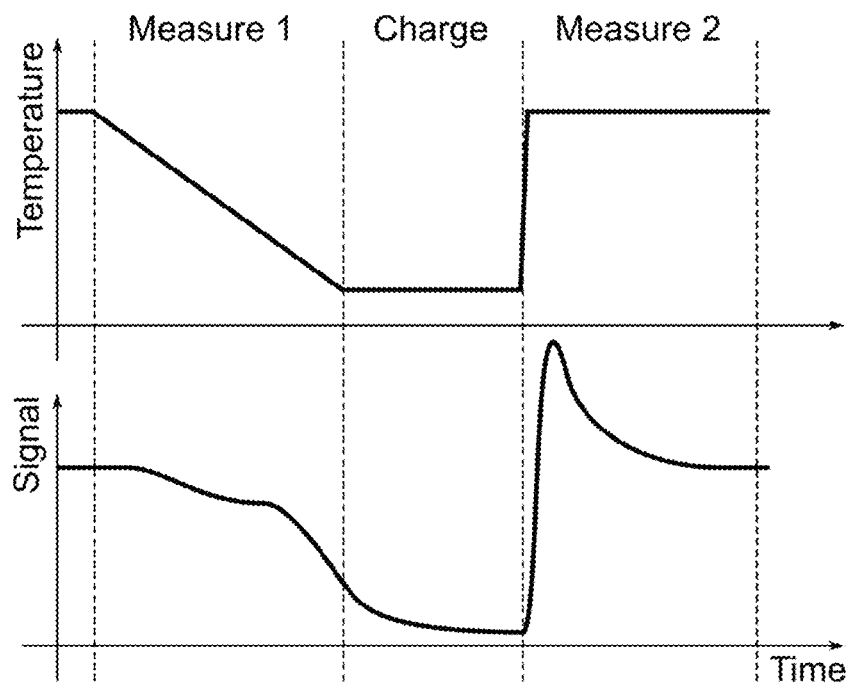
FIG. 5C shows a graph of temperature as a function of time and a corresponding graph of first response as a function of time for a detector and a method according to an exemplary embodiment.

FIG. 5C shows a graph of temperature as a function of time and a corresponding graph of first response as a function of time for a detector and a method according to an exemplary embodiment. FIG. 5C includes both the second mode of operation and the first mode of operation, successively, as described with respect to FIGS. 5B and 5A, respectively. A hold period at a relatively low temperature after the second mode of operation and before the first mode of operation results in sorption of a relatively large amount of the first analyte sorbed in and/or on the first sorbent, such that a relatively large positive response is observed during the second measure phase.

Analysis of Measurements

The standard method of using the PID-AH VOC sensor is to determine in advance the output voltage without any VOC present and compare this to the output voltage in the presence of the VOC. The difference in voltage is linearly related to the concentration of the VOC, though the constant of proportionality varies between different VOCs. A more sensitive measurement (lower detection limit) may be achieved by taking multiple readings to more accurately determine the output voltage, thus the longer the measurement period the more sensitive the overall measurement. This depends on the zero-VOC voltage being stable and known to a sufficient accuracy. In practice, this is not the case, so for the purposes of this work the zero-VOC voltage was determined each time a traditional measurement was taken. This is possible because a VOC-free carrier gas is available. If such a carrier gas is not available, a different approach is required, as described below.

Two algorithms for analysing the response are presented.

Figure 6:
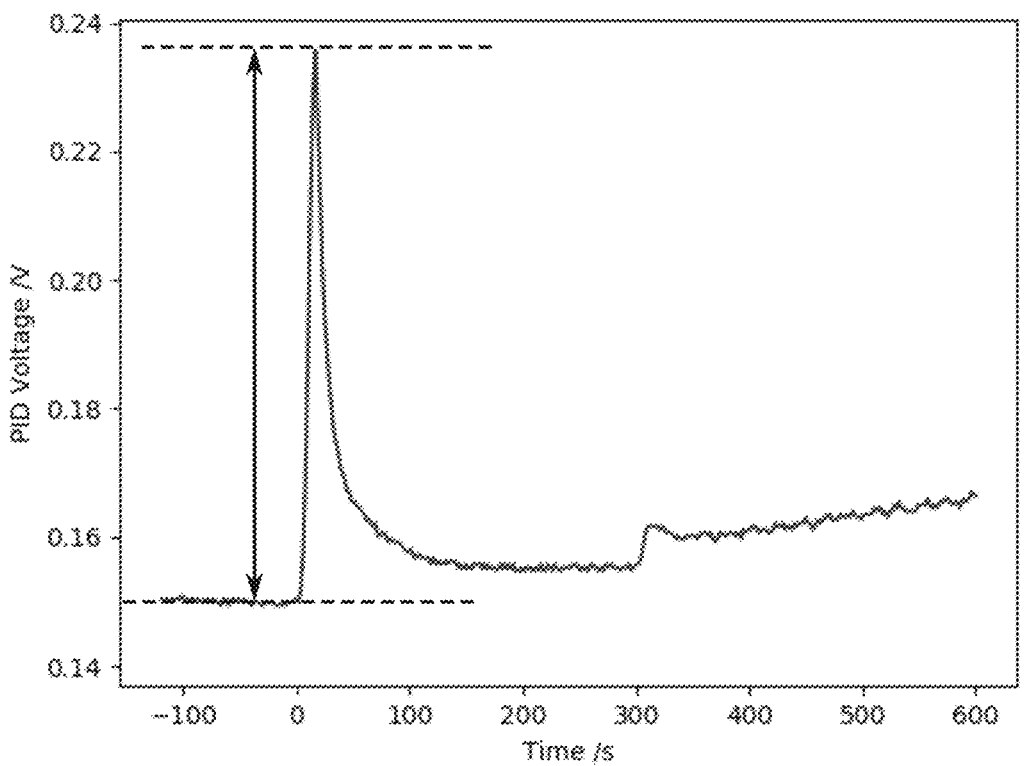
FIG. 6 shows a graph of first response as a function of time for a detector and a method according to an exemplary embodiment.

The first algorithm, as shown in FIG. 6, involves measuring the height of the peak which occurs when the temperature is increased. While conceptually simple and easy to implement, the transient nature of the peak makes it hard to measure at the highest value and means that multiple measurements may not be taken to reduce noise. The measurement may be taken as the difference between the value at the lower temperature (i.e. $T_0$) to the value at the peak at the higher temperature (i.e. $T_1$) or from the peak to the subsequent equilibrium value. The latter would avoid temperature dependent shifts in the PID output voltage, while the former should give more significant response (the VOC concentration at the lower temperature should be slightly suppressed due to VOCs depositing on the porous media, so the range of concentration should be higher). The latter would also give a more immediate response. In this work, the former is the definition of peak height used.

FIG. 6 shows a graph of first response as a function of time for a detector and a method according to an exemplary embodiment. In more detail, FIG. 6 shows an example of a VOC peak at the measure and check phases. The charge phase ends at time=0 s when the temperature is increased leading to a peak in the VOC concentration and the PID voltage. The temperature is then held constant until the check phase at time=300 s, when it is increased again. The double-headed arrow shows the definition of the peak height.

Figure 7:
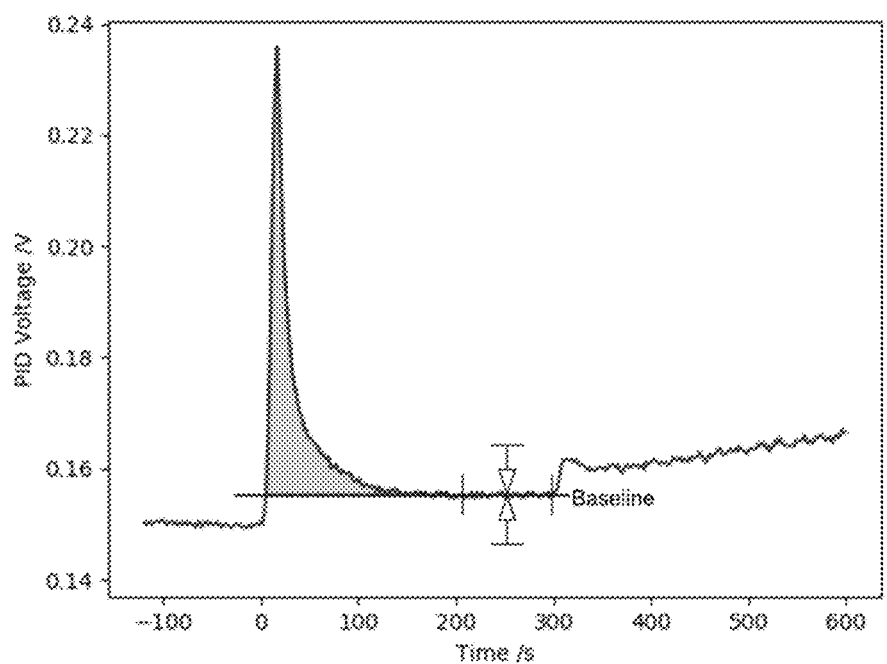
FIG. 7 shows a graph of first response as a function of time for a detector and a method according to an exemplary embodiment.

The second algorithm, as shown in FIG. 7, is to take the area under the PID voltage curve due to the evaporating VOCs. The area should be more closely related to the quantity of VOC evaporated than the peak height because it does not depend on all of the VOC being released at the same point in time. It also allows measurement over the duration of the peak which reduces the measurement noise compared to the single point in the height. It is better to use a linear fit for the baseline than a constant as there is a slow response to the temperature step which can cause an error at the low concentrations. FIG. 7 shows a graph of first response as a function of time for a detector and a method according to an exemplary embodiment. In more detail, FIG. 7 shows measurement of VOC peak area at the measure phase. A baseline is fitted to the second half of the period between two increases in temperature at time=0 s and time=300 s. The baseline is extrapolated under the peak at time=0 s. The area between this baseline and the peak is the peak area.

Temperature Effects

Figure 8:
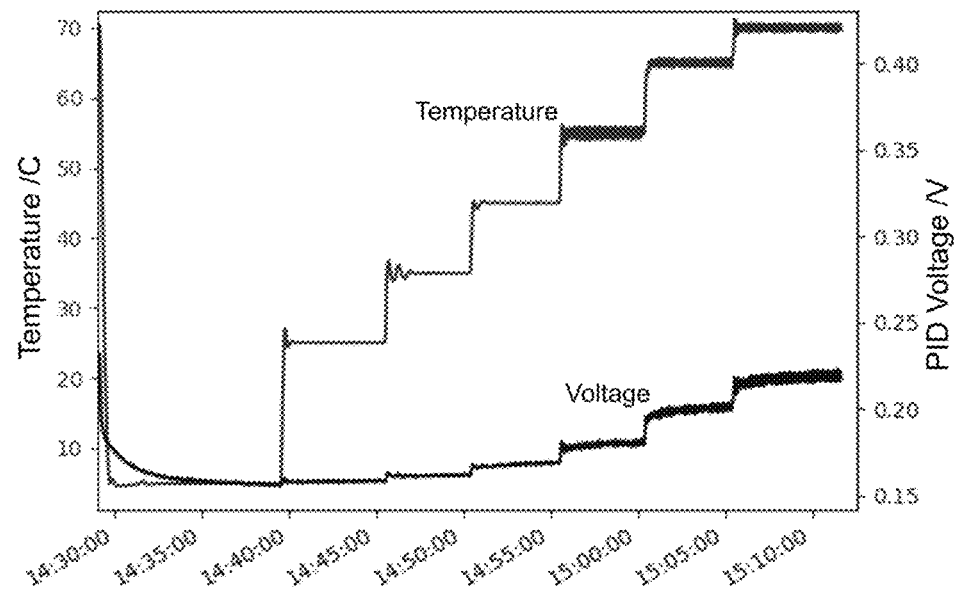
FIG. 8 shows a graph of temperature as a function of time and a corresponding graph of first response as a function of time for a first sorbent for a detector and a method according to an exemplary embodiment.
Figure 9:
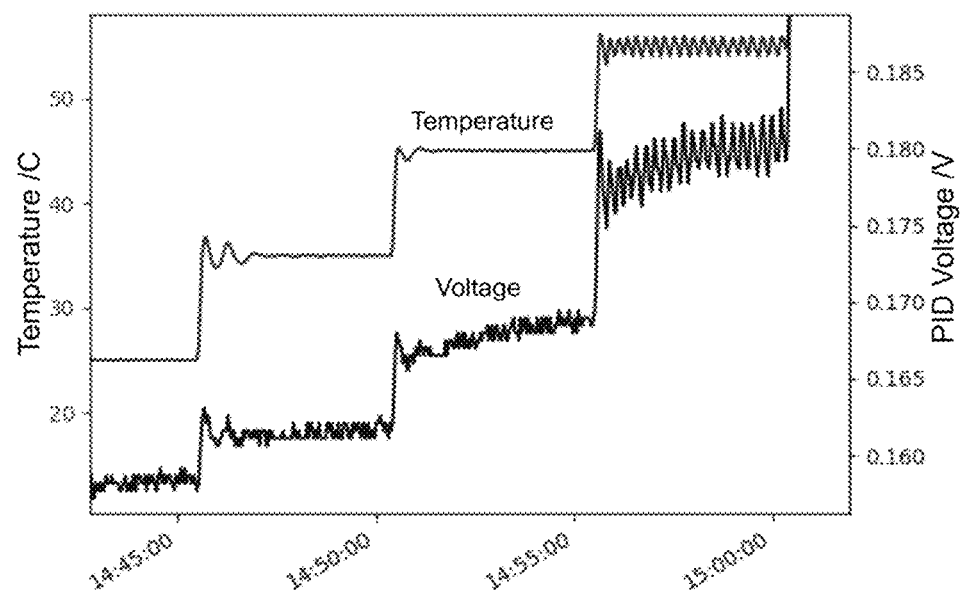
FIG. 9 shows a graph of temperature as a function of time and a corresponding graph of first response as a function of time for a first sorbent for a detector and a method according to an exemplary embodiment.
Figure 10:
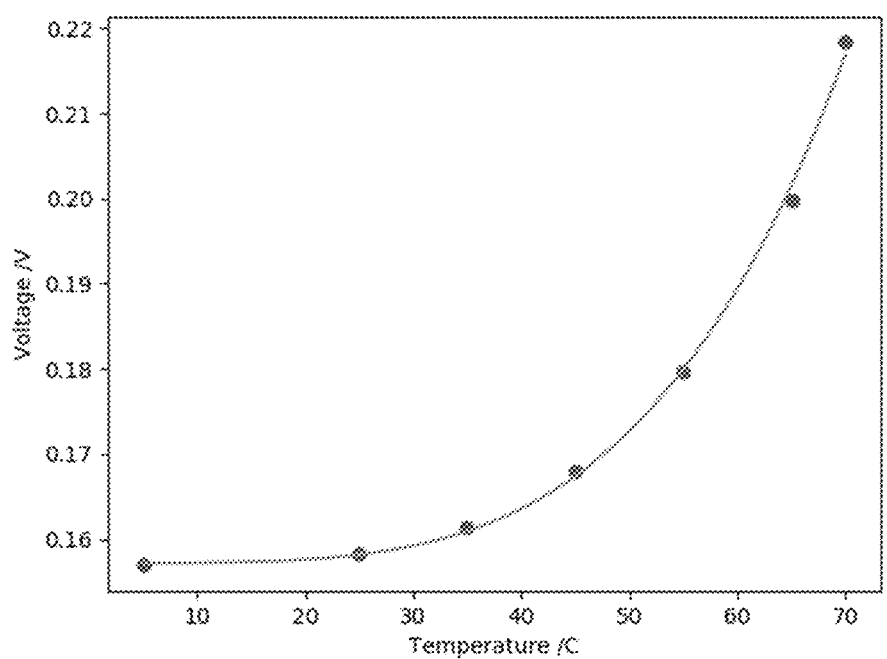
FIG. 10 shows a graph of first response as a function of temperature for a sensor for a detector and a method according to an exemplary embodiment.

The PID voltage has a dependence on temperature (FIG. 8 and FIG. 9). As the temperature increases, the PID voltage increases with approximately a quartic relationship with respect to temperature (FIG. 10).

There appear to be two time-constants involved in this relationship. First is a fast response with a time constant of the order of a few seconds. This can be seen in the mirroring of the overshoot and the oscillations which occur in the temperature in the PID voltage. The second is a slow response, of the order 5 minutes, where the PID voltage gradually shifts to a new equilibrium value following a step change in temperature.

The cause and the coupling mechanism are not known yet.

The temperature control is limited to about 80° C. at the top, so to ensure that the highest temperature was repeatable a maximum temperature of 70° C. was used. At temperatures above about 50° C. oscillations in the temperature with a time constant of a few seconds and an amplitude of about 1° C. were observed. To avoid seeing these in the measurement phase a measurement temperature of 40° C. was used. 40° C. is also lower than the bulk of the temperature dependent change in PID output voltage. The lower temperature of 5° C. was chosen as being low enough to get good deposition of the VOCs while being comfortably within the achievable range.

FIG. 8 shows a graph of temperature as a function of time and a corresponding graph of first response as a function of time for a first sorbent for a detector and a method according to an exemplary embodiment. In more detail, FIG. 8 shows a time-series showing porous silica temperature and PID voltage under a constant purge flow.

FIG. 9 shows a graph of temperature as a function of time and a corresponding graph of first response as a function of time for a first sorbent for a detector and a method according to an exemplary embodiment. In more detail, FIG. 9 shows an excerpt from FIG. 8 showing the PID voltage mirroring the overshoot and oscillations in the porous silica temperature. The slow time-constant response of a gradual shift to a new equilibrium voltage can also be seen, particularly at higher temperatures.

FIG. 10 shows a graph of first response as a function of temperature for a sensor for a detector and a method according to an exemplary embodiment. In more detail, FIG. 10 shows steady-state PID voltage V and temperature T under a constant purge flow.

The fitted line is a quartic of the form $V=aT^4+b$.

Results
Concentration of VOC

The effect of concentration on the system was measured for two different VOCs (isopropyl alcohol (IPA) and limonene) at 3 concentrations each. For each VOC and concentration, the steady state PID voltage at a fixed temperature was measured followed by temperature cycling of the porous media to measure the dynamic response. Because the zero-VOC voltage of the PID-AH was found to vary these measurements were also performed on the VOC-free carrier gas to establish the baseline performance. Details of the measurement steps, as shown in FIG. 11, are:

1. Change to a new gas mixture. The sensor is in the purge gas (99.99% $N_2$), so this gives time (15 minutes) for the new gas mixture to settle down.
2. Steady state (purge). Measure the PID voltage under the purge gas (99.99% $N_2$) at 40° C. 10-minute settling time followed by 5 minutes of measurements.
3. Steady state (sample). Measure the PID voltage under the sample gas at 40° C. 5-minute settling time followed by 5 minutes of measurements. The first analyte is carried in 99.99% $N_2$.
4. Clear. 10 minutes at 70° C. to get clear any residual VOCs from the porous silica, using the first analyte carried in 99.99% $N_2$. The aim of this step is to provide a consistent starting point for each test.
5. Charge. 10 minutes at 5° C. to absorb VOCs from the gas, using the first analyte carried in 99.99% $N_2$. The PID voltage will drop during this step for two reasons—first because the temperature is lower, and second because the porous silica is absorbing VOCs from the gas flow and hence lowering the VOC concentration in the chamber. Potentially, given long enough, the latter effect might decrease as the porous silica becomes saturated and stops absorbing further VOCs.
6. Measure. 5 minutes at 40° C. to see the response of the sensor, using the first analyte carried in 99.99% $N_2$. The porous silica releases the VOCs absorbed at the lower temperature leading to an increase in the VOC concentration in the chamber. This effect causes a peak in the PID voltage above the steady state level. The flow through the chamber gradually clears the excess concentration and the PID voltage returns to the steady state value.
7. Check. 70° C. for 5 minutes to see if any VOCs remained in the porous silica, using the first analyte carried in 99.99% $N_2$. Any remaining absorbed VOCs should be released at this point, so a pattern of a peak and relapse in the PID voltage (as seen in step 6) would indicate that the release of VOCs in step 6 was incomplete.
8. Repeat of 4-7 under purge gas (99.99% $N_2$) to check the background response of the system.

Figure 11:
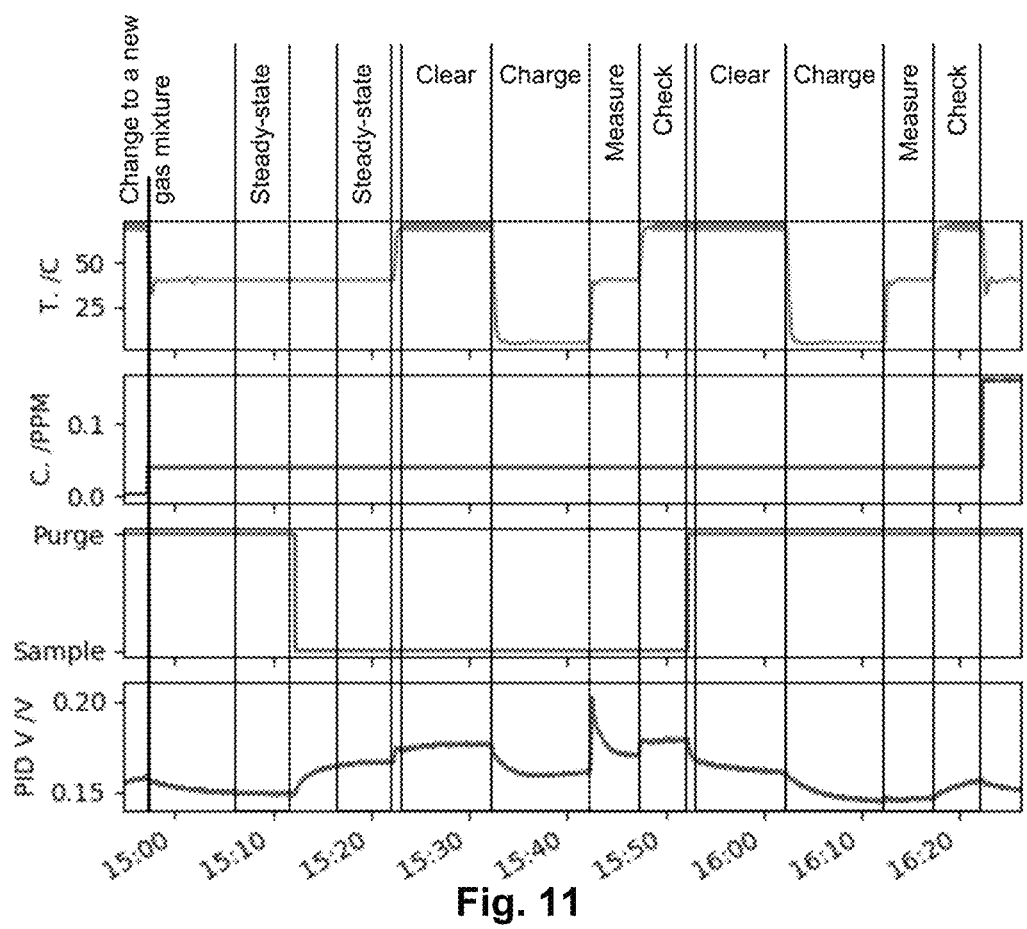
FIG. 11 shows a graph of temperature as a function of time and corresponding graphs of concentration of the first analyte, first gas and first response as a function of time for a detector and a method according to an exemplary embodiment.

FIG. 11 shows a graph of temperature as a function of time and corresponding graphs of concentration of the first analyte, first gas and first response as a function of time for a detector and a method according to an exemplary embodiment. In more detail, FIG. 11 shows system parameters and PID voltage illustrating the steps used to enhance the response of a PID with a porous media.

Figure 12:
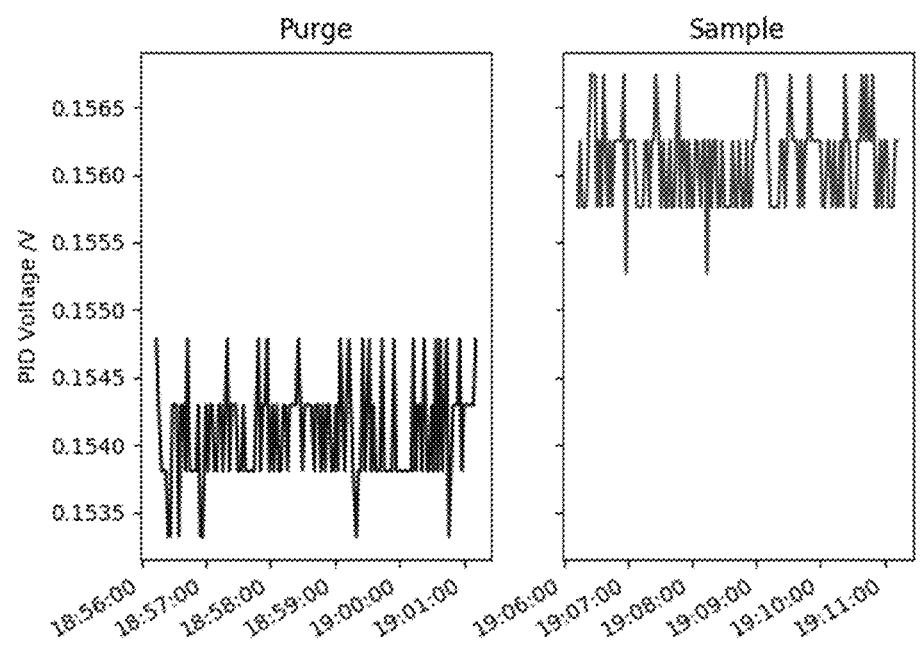
FIG. 12 shows a graph of first response as a function of time in absence of a first analyte and during exposure of the first analyte.

The steady-state PID voltage is shown in FIG. 12 for IPA at 0.0033 ppm. This concentration can be detected directly by the PID, though the measurement is approaching the quantisation of the ADC used to read the PID. Note that the difference between the sample reading and the VOC-free purge reading is less than the day-to-day variability in the VOC-free purge reading, so without the capability to compare to a purge gas this concentration would be hard to detect.

FIG. 12 shows a graph of first response as a function of time in absence of a first analyte and during exposure of the first analyte. In more detail, FIG. 12 shows steady-state PID voltage for IPA at 0.0033 ppm. The difference in voltage is only a few quantisation steps of the ADC.

Figure 13:
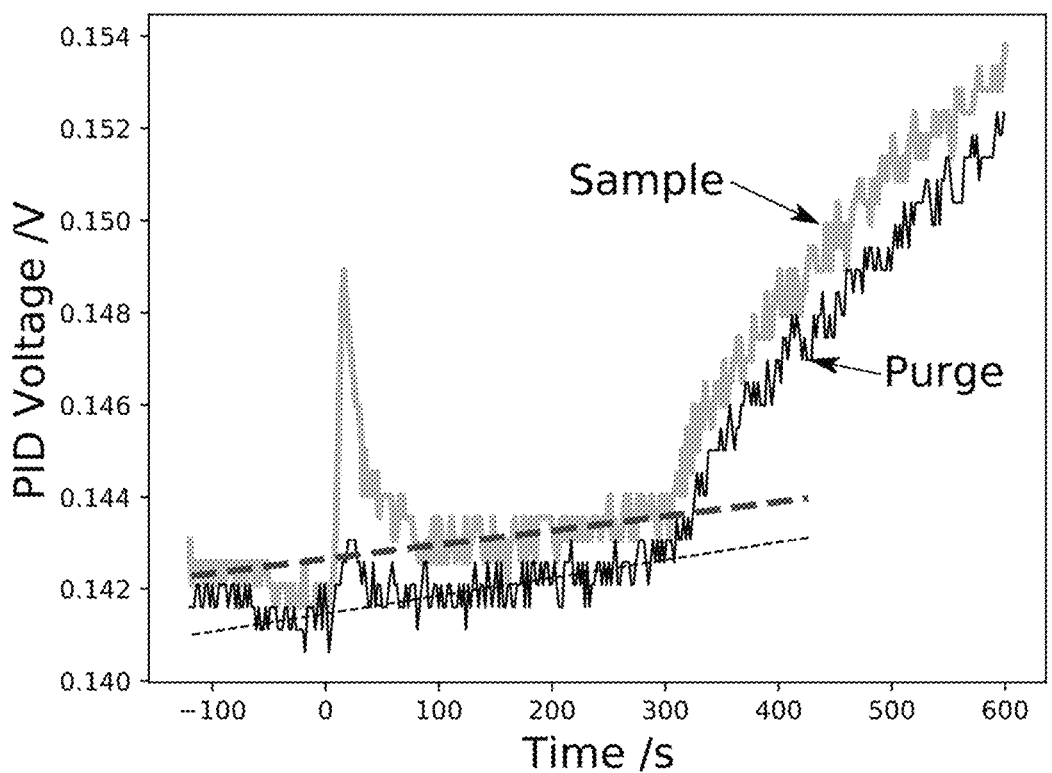
FIG. 13 shows a graph of first response as a function of time for a detector and a method according to an exemplary embodiment.

The transient voltage curves during the measure and check phases is shown in FIG. 13 for the same gas. Again, the response in the VOC-free purge gas is also shown. At the start of the measure phase (time=0 s) there is a step change in temperature from 5° C. to 40° C. and a corresponding peak in the PID voltage. This peak is higher (0.012 V) than the steady state change in voltage (0.002 V) and occurring at a known time is easier to detect. There is also a peak in the purge gas (0.005 V), probably due to residual VOCs not cleared from the porous silica in the clear phase. This gives a contribution to the peak height due to the VOCs of 0.008 V, which is 4 times the steady state response.

FIG. 13 shows a graph of first response as a function of time for a detector and a method according to an exemplary embodiment. In more detail, FIG. 11 shows the transient PID voltage for the measure (time=0 s) and check (time=300 s) phases for IPA at 0.033 ppm.

The baselines for calculating the peak area are also shown as dotted lines. Of note here are the slow time-constant effects which mean that the voltage is not in a steady state during any of these phases. This causes the baseline to be sloped rather than constant and reduces the error in measuring the peak area. This is typical of measurements at very low concentrations, while at higher concentrations the peak is much larger and these details are lost. The peak area here is 0.147 with the VOC, while the purge peak area is 0.042 (the units are proportional to volt-seconds with some scale factors associated with the measurement times), so a difference of 0.105, which is approximately 50 times the steady state response.

The signal to noise ratio of these measurements may depend, at least in part, on how the detector is used. The noise level for the measurement of the steady state voltage will be proportional to $\sqrt{1/t}$ where t is the measurement duration. The noise level for the peak height will be constant as this depends on just the one measurement point. The noise level for the peak area will depend on $\sqrt{1/t\_s}$ where t_s is the duration for which the peak exists. While this scaling initially seems to favour the steady state response, both peak measurements benefit from the increased signal magnitude compared to the steady state change. If the measurement duration for the steady state measurement is the same order of magnitude as the peak duration, then the noise levels for the peak area and the steady state are similar and the sensitivity or detection limit for these two methods can be taken approximately as the ratio of their signal strengths.

Figure 14:
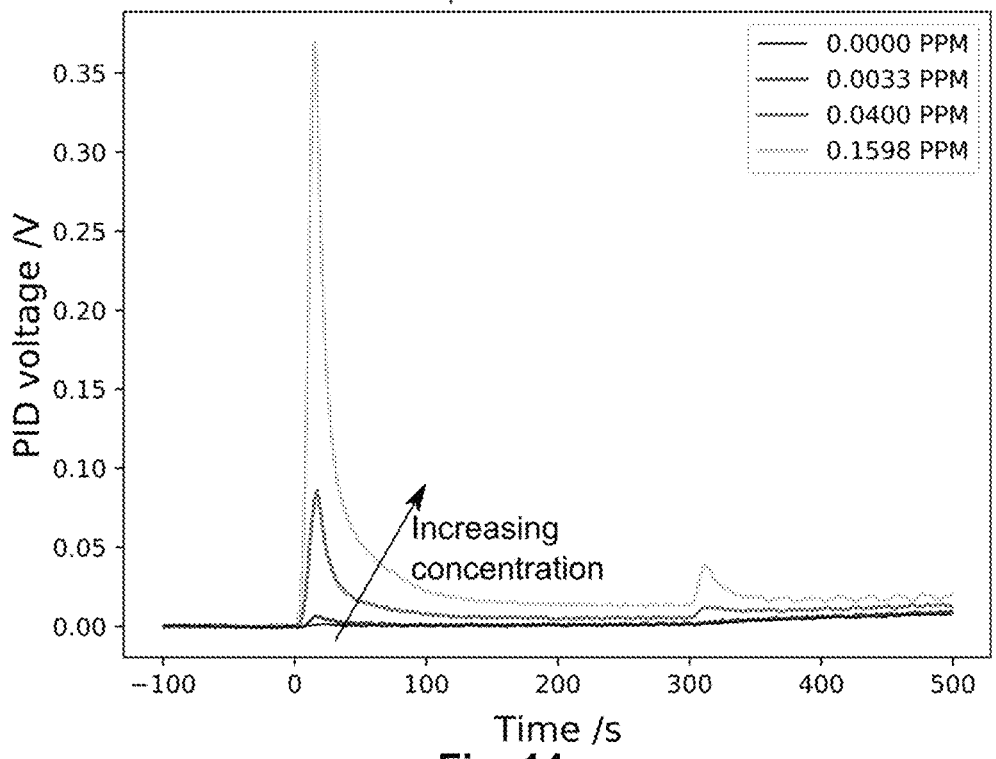
FIG. 14 shows a graph of first response as a function of time for three different concentrations of a first analyte for a detector and a method according to an exemplary embodiment.

All three concentrations of IPA and a purge sample are shown in FIG. 14. It is clear, that the peak at the measure phase grows with increasing concentration, and that it grows faster than the steady state voltage. It can also be seen that not all the VOC is being evaporated during the measure phase, and at the higher concentrations there is a noticeable peak developing at the check phase (at time=300 s) when the temperature is increased to 70° C.

FIG. 14 shows a graph of first response as a function of time for three different concentrations of a first analyte for a detector and a method according to an exemplary embodiment. In more detail, FIG. 14 shows the transient PID voltage curves for IPA at three concentrations and under purge. The voltage offset at t=0 s is removed from all traces so that the peaks may be compared.

Figure 15:
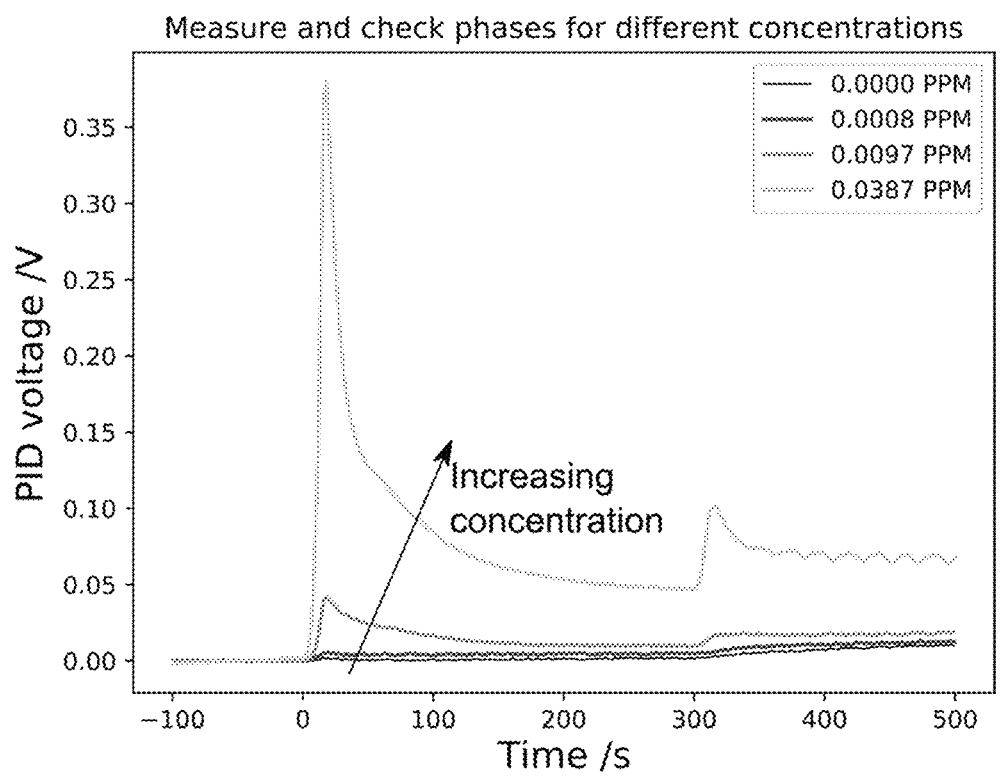
FIG. 15 shows a graph of first response as a function of time for three different concentrations of a first analyte for a detector and a method according to an exemplary embodiment.

The transient PID voltage curves for limonene are shown in FIG. 15. The ratio between the three concentrations is the same as between the concentrations of IPA, though the absolute levels are approximately 4 times lower. The same pattern of increasing peak height and area with concentration is present, and of a peak developing in the check phase at higher concentrations. The peak has a longer tail for limonene than for IPA, and at the lowest concentration (0.8 ppb) this makes fitting the baseline difficult.

FIG. 15 shows a graph of first response as a function of time for three different concentrations of a first analyte for a detector and a method according to an exemplary embodiment. In more detail, FIG. 15 shows the transient PID voltage curves for Limonene at three concentrations and under purge. The voltage offset at t=0 s is removed from all traces so that the peaks may be compared.

Figure 16:
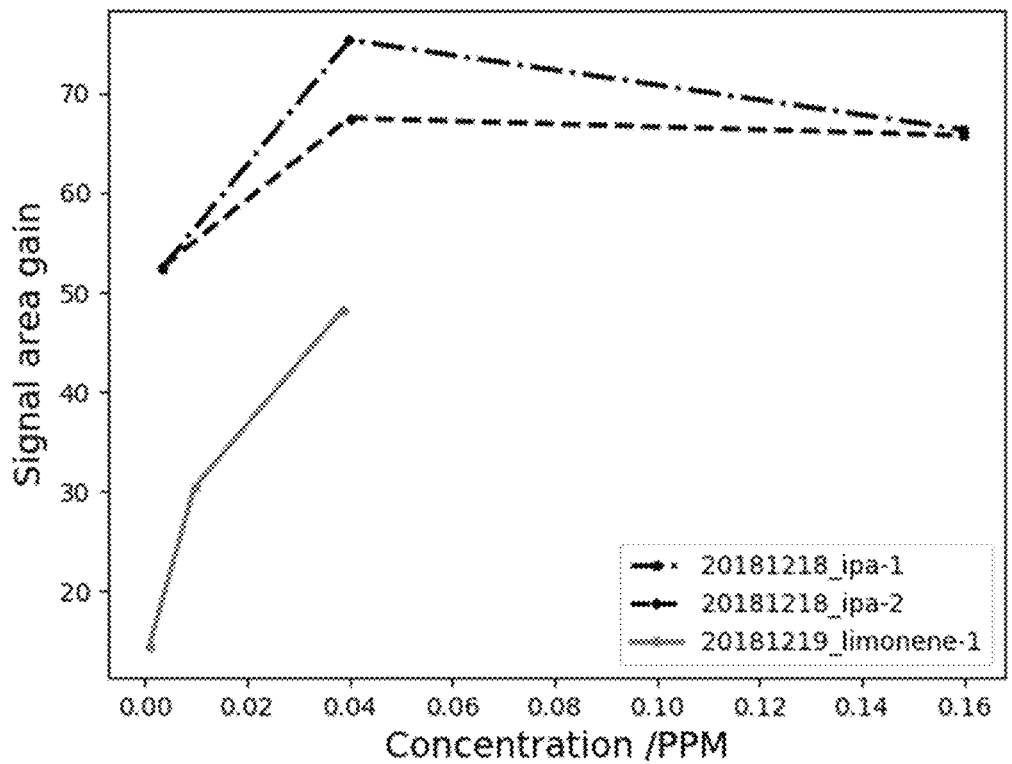
FIG. 16 shows a graph of sensitivity increase for a detector and a method according to an exemplary embodiment.
Figure 17:
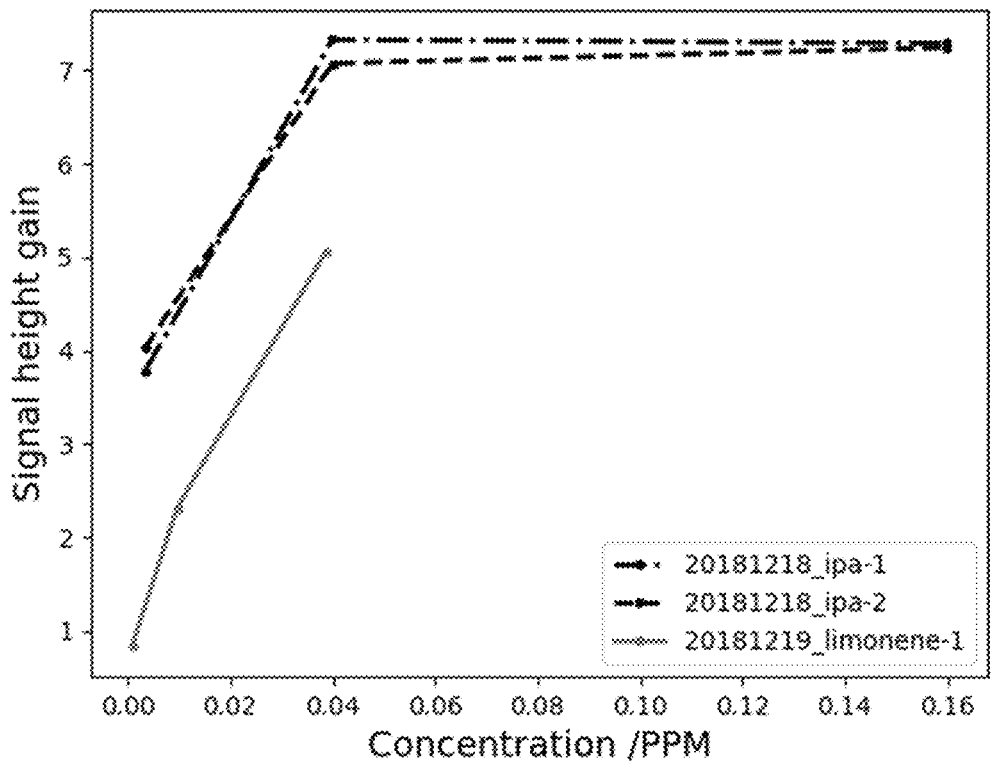
FIG. 17 shows a graph of sensitivity increase for a detector and a method according to an exemplary embodiment.

The gain for peak area and peak height compared to the steady state voltages are shown in FIG. 16 and FIG. 17 for two series of tests with IPA and one with limonene. Both measurements show the same trends—a high gain at the higher concentrations of IPA falling off at the lowest IPA concentration, and a gain reducing with reducing concentrations of limonene. While the gain is not constant as a function of concentration, calibration curves, optionally for each VOC of interest, may be generated for quantitative measurements. That the gain decreases at the lower concentrations means that the effectiveness in improving the detection threshold may be relatively limited.

FIG. 16 shows a graph of sensitivity increase for a detector and a method according to an exemplary embodiment. In more detail, FIG. 16 shows peak area gain as a function of concentration of the first analyte.

FIG. 17 shows a graph of sensitivity increase for a detector and a method according to an exemplary embodiment. In more detail, FIG. 17 shows peak height gain as a function of concentration of the first analyte.

Dwell Time

The effect of the dwell time during the charge phase was studied using IPA at a relatively high concentration (0.16 ppm). For each dwell time there was a clear phase (5 minutes), charge phase (for the required duration), measure phase (5 minutes) and check phase (5 minutes), as shown in FIG. 18.

Figure 18:
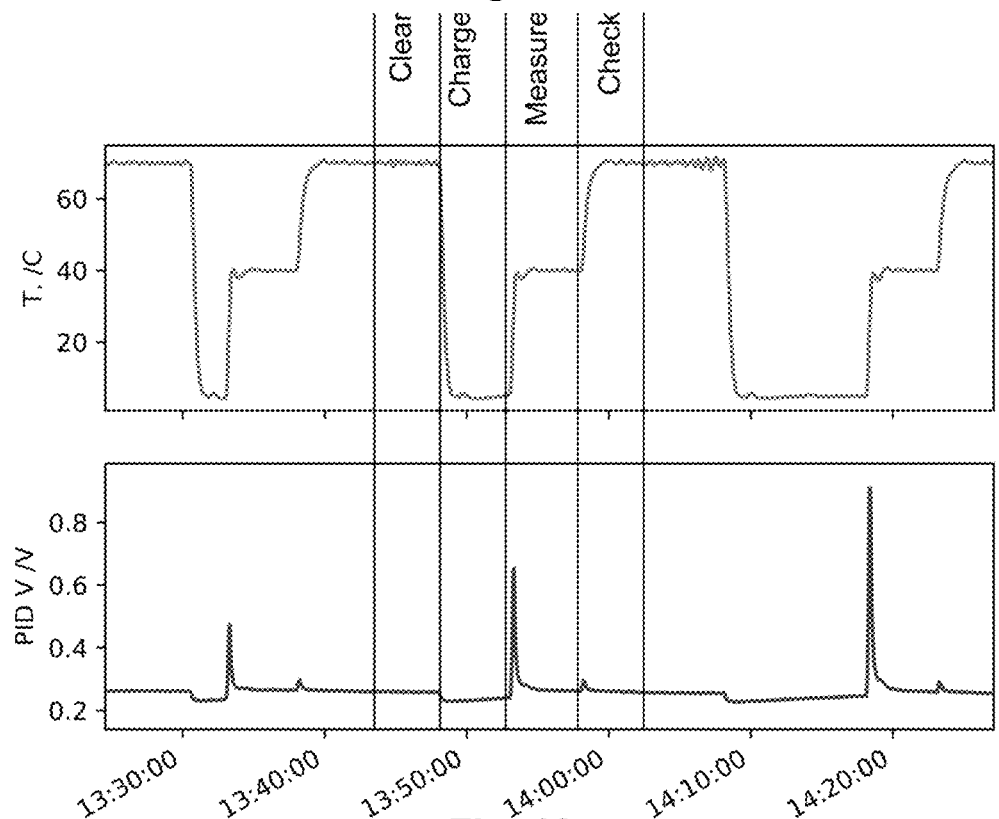
FIG. 18 shows a graph of temperature as a function of time and a corresponding graph of first response as a function of time for a detector and a method according to an exemplary embodiment.

FIG. 18 shows a graph of temperature as a function of time and a corresponding graph of first response as a function of time for a detector and a method according to an exemplary embodiment. In more detail, FIG. 18 shows Temperature profile and PID response for the dwell time tests.

Figure 19:
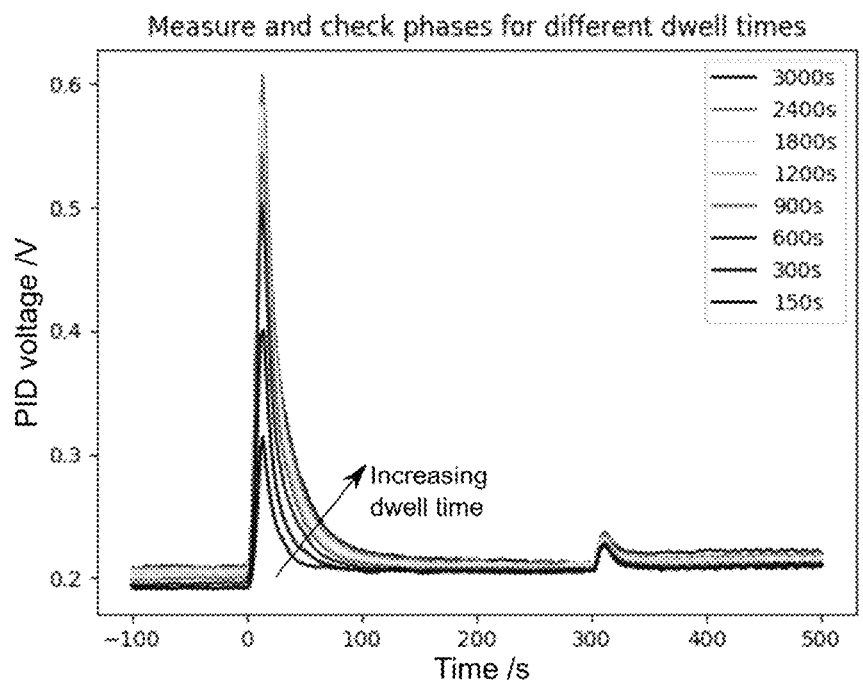
FIG. 19 shows a graph of first response as a function of time for a detector and a method according to an exemplary embodiment.

The transient PID voltage curves are shown in FIG. 19 for a range of dwell times. Both the peak height and the peak area can be seen to increase with longer dwell times.

Interestingly, the peak for the check phase does not seem to vary in size with dwell time, suggesting that this may be more complicated than residual VOCs being driven off at the higher temperature.

FIG. 19 shows a graph of first response as a function of time for a detector and a method according to an exemplary embodiment. In more detail, FIG. 19 shows the transient PID voltage curves for different dwell times. The start of the measure phase is at t=0 s, the start of the check phase is at t=300 s.

Figure 20:
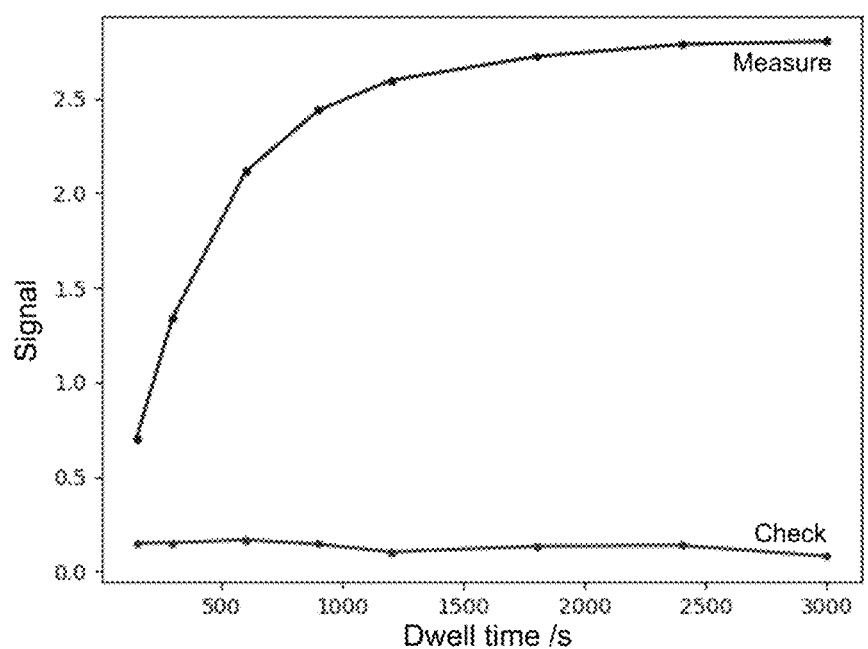
FIG. 20 shows a graph of first response as a function of dwell time for a detector and a method according to an exemplary embodiment.

Plotting the peak area as a function of dwell time shows that the measure phase peak does saturate as expected, with the knee in its response being at about 900 s (FIG. 20).

This would therefore be a good dwell time to use for getting the maximum sensitivity in the shortest time. It is likely that the saturation time will depend on the concentration so that lower concentrations will benefit from a longer dwell time. In this case the dwell time should be thought of as setting the measurement range.

FIG. 20 shows a graph of first response as a function of dwell time for a detector and a method according to an exemplary embodiment. In more detail, FIG. 20 shows peak area plotted against dwell time.

Temperature Ramps (VOC Classification)

Generally, in conventional detectors, the temperature is changed as quickly as possible, for example increased at 150° C./min or more, to achieve the largest possible peak response. In this work, the temperature going from the charge to the measure phase was ramped at a very much lower rate of just 10° C./min to allow the profile of the VOC evaporation to be measured. In these experiments a single cycle of clear (5 minutes), charge (10 minutes), measure and check (5 minutes) was performed. The measure cycle was extended by ramping the temperature from 5° C. to 40° C. at 10° C./min before holding for 5 minutes.

Figure 21:
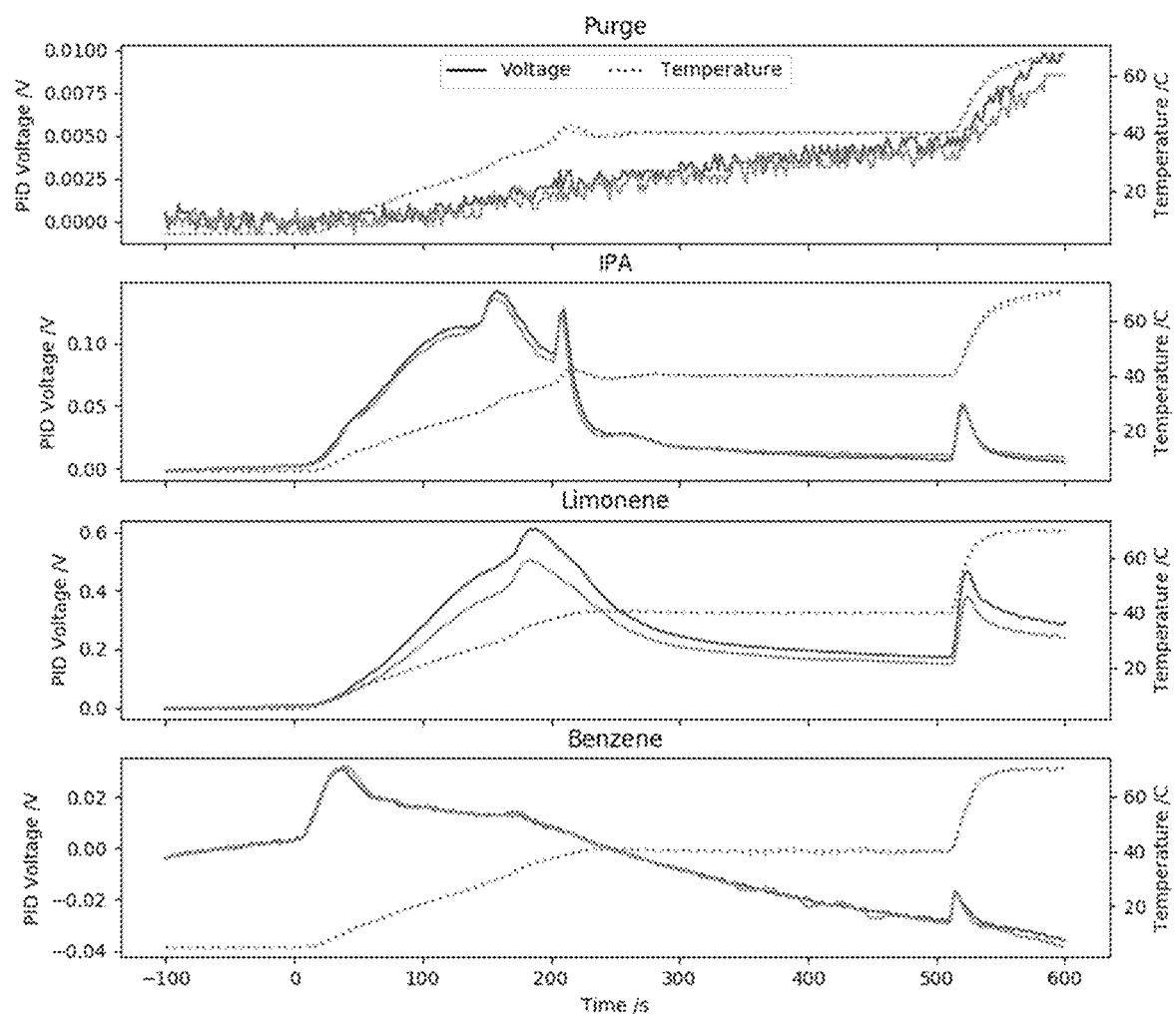
FIG. 21 shows a graph of first response as a function of time for $N_2$, IPA, limonene and benzene for a detector and a method according to an exemplary embodiment.

FIG. 21 shows a graph of first response as a function of time for $N_2$, IPA, limonene and benzene for a detector and a method according to an exemplary embodiment. In more detail, FIG. 21 shows the temperature profiles under purge (i.e. $N_2$), 0.16 ppm IPA, 0.039 ppm limonene and 1 ppm benzene. The dotted line shows temperature, the solid line shows PID voltage. The temperature is ramped from 5° C. to 40° C. in 3.5 minutes starting at time=0 s. At time=510 s, the temperature is stepped to 70° C. to see how much VOC remains on the sample. The voltage offset at t=0 s is removed from all traces. It is clear that IPA, limonene and benzene have very different traces compared to the purge gas. There are also some notable differences between IPA, limonene and benzene, in particular the initial peak in voltage at the start of the ramp for benzene and the sharp peak in voltage towards the end of the ramp for IPA. The PID responses have a large broad peak and smaller sharper peaks. The sharper peaks are due to the unstable temperature control (as indicated by the dashed line). Nevertheless, the results indicate that it should be possible to differentiate between these three VOCs from the shape of their response. That is, the respective first responses of IPA, limonene and benzene are characteristic first responses, respectively.

Figure 22:
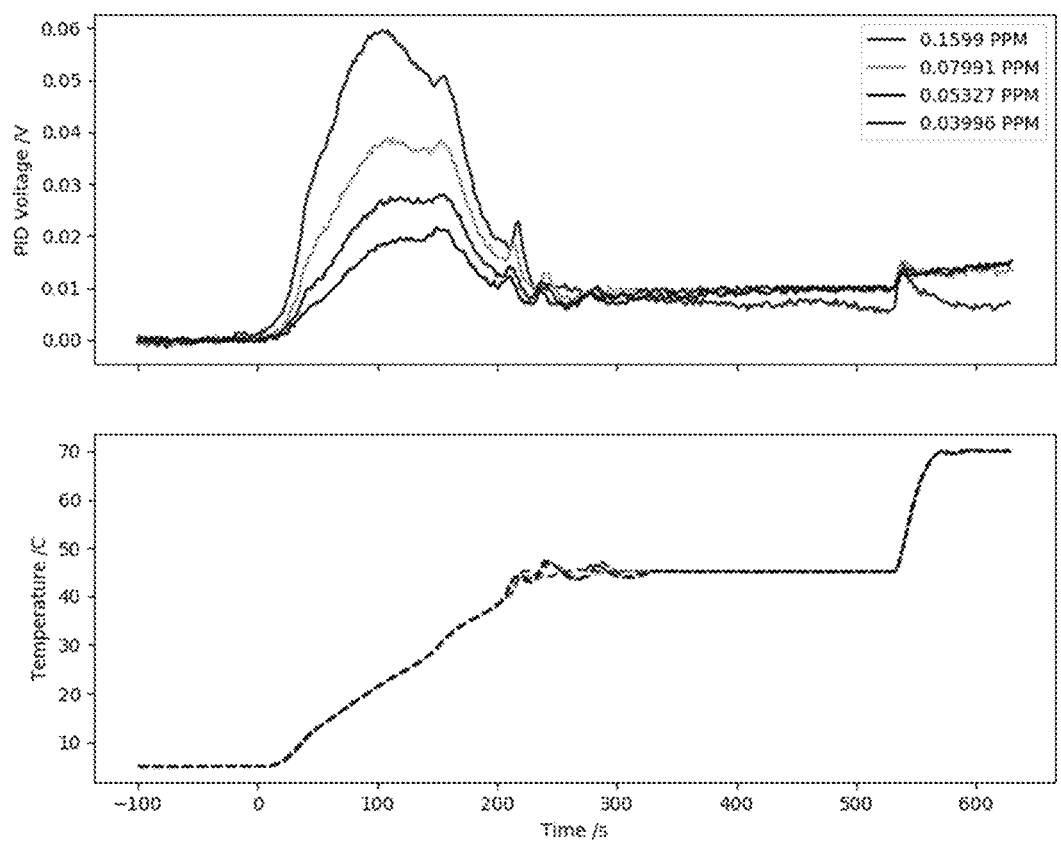
FIG. 22 shows a graph of temperature as a function of time and a corresponding graph of first response as a function of time for IPA at four different concentrations for a detector and a method according to an exemplary embodiment.

FIG. 22 shows a graph of temperature as a function of time and a corresponding graph of first response as a function of time for IPA at four different concentrations (0.03996 ppm, 0.05327 ppm, 0.02991 ppm and 0.1599 ppm) for a detector and a method according to an exemplary embodiment. The temperature is ramped from 5° C. to 40° C. in 3.5 minutes starting at time=0 s. At time=510 s, the temperature is stepped to 70° C. to see how much IPA remains on the sample. The voltage offset at t=0 s is removed from all traces. The shapes of the respective responses are similar (i.e. characteristic of IPA).

Figure 23:
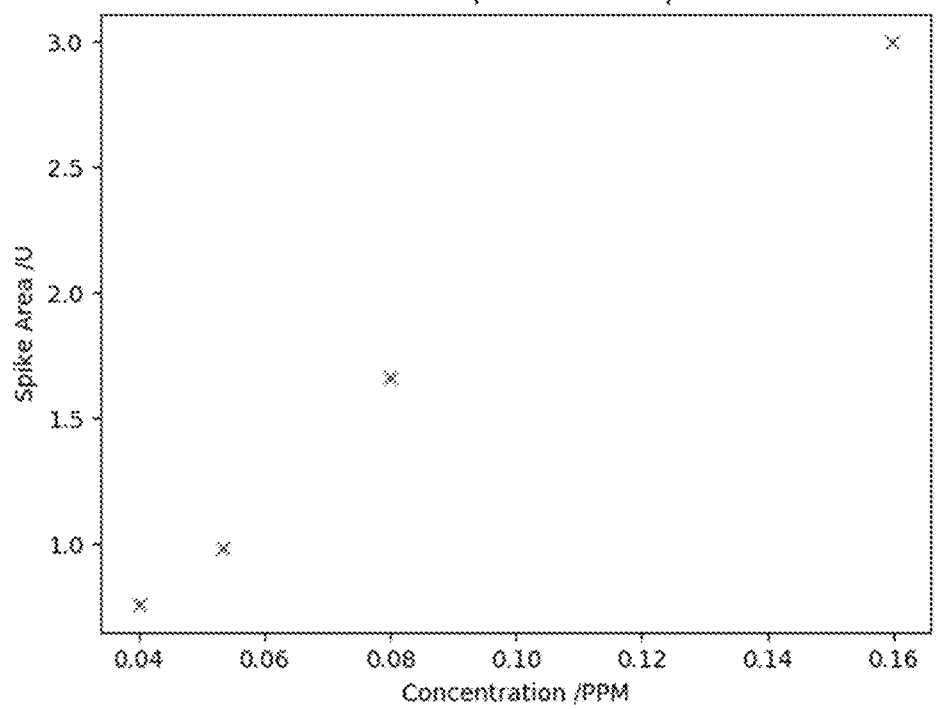
FIG. 23 shows a graph of first response as a function of concentration for IPA.
Figure 26:
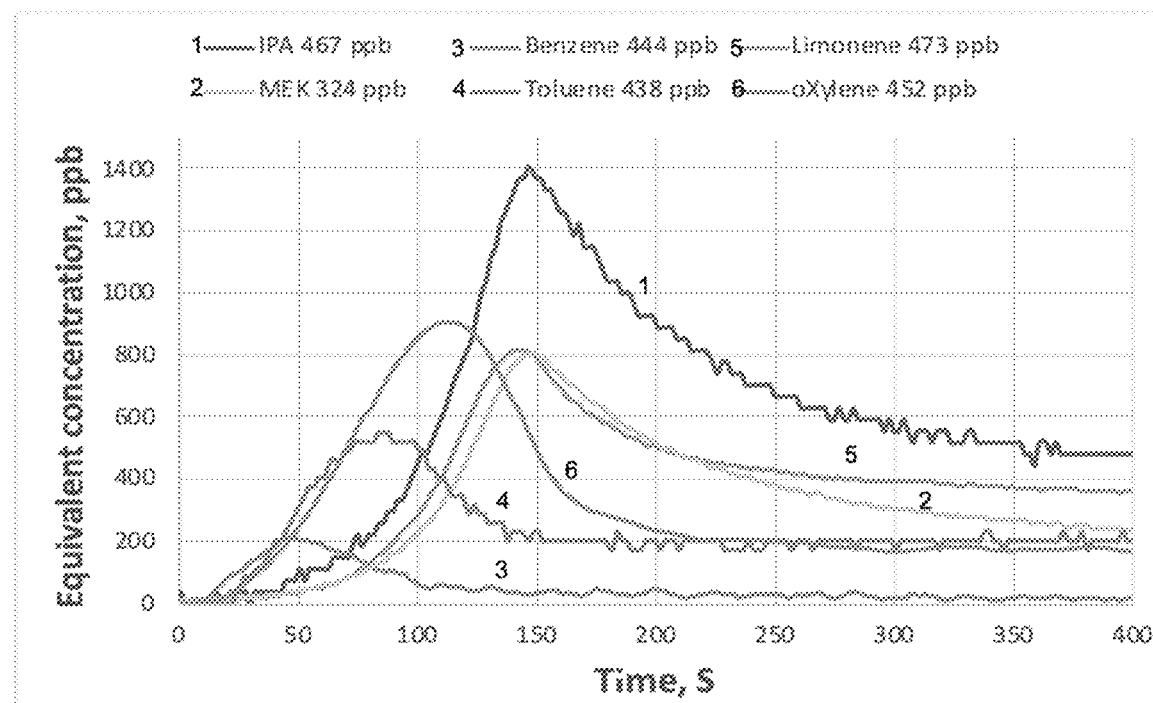
FIG. 26 shows a graph of equivalent concentration (ppb) as a function of time (s) for IPA, MEK, benzene, toluene, limonene and o-Xylene.

FIG. 23 shows a graph of first response as a function of concentration for IPA, for the peak areas of FIG. 22. The relationship between peak area and concentration is linear, thereby allowing quantitative determination of the concentration for a given peak area. FIG. 26 shows a graph of equivalent concentration (ppb) as a function of time (s) for IPA, MEK, benzene, toluene, limonene and o-Xylene. Particularly, FIG. 26 shows a graph of PID output voltage signal converted to concentration as a function of time. During desorption, the temperature was increased gradually from 5° C. to 70° C. Particularly, sorbing of the analytes was at 5°

C. for 300 s while desorption was by heating to 70° C. over 150 s. The flow rate of gas was kept constant at 50 mL/min. The different analytes desorb at different times and hence temperatures (i.e. the first response comprises and/or is a first characteristic response of a set of characteristic responses of the first analyte).

Figure 27:
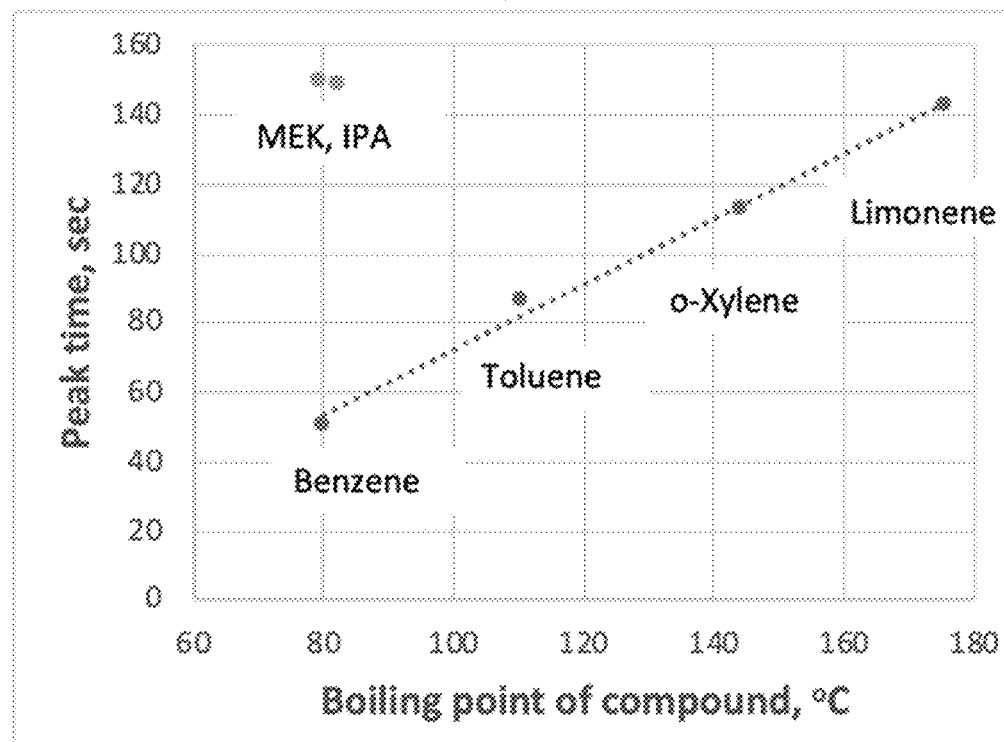
FIG. 27 shows a graph of peak time (s) as a function of boiling point (° C.) for IPA, MEK, benzene, toluene, limonene and o-Xylene.

FIG. 27 shows a graph of peak time (s) as a function of boiling point (° C.) for IPA, MEK, benzene, toluene, limonene and o-Xylene. Particularly, the four non-polar analytes (benzene, toluene, o-xylene and limonene) have similar affinities for the surface (i.e. the sorbent), and their desorption times and hence temperatures correlate, for example directly, linearly, with their respective boiling points. Methyl ethyl ketone (MEK) and isopropyl alcohol (IPA) more strongly interact with the surface, so desorb at a higher temperatures i.e. at later times.

Figure 28A:
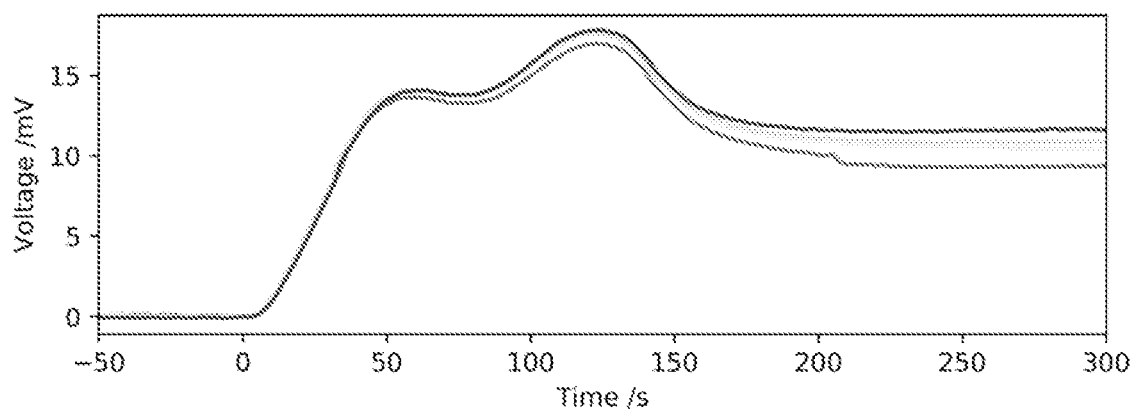
FIG. 28A shows a graph of temperature as a function of time.
Figure 28B:
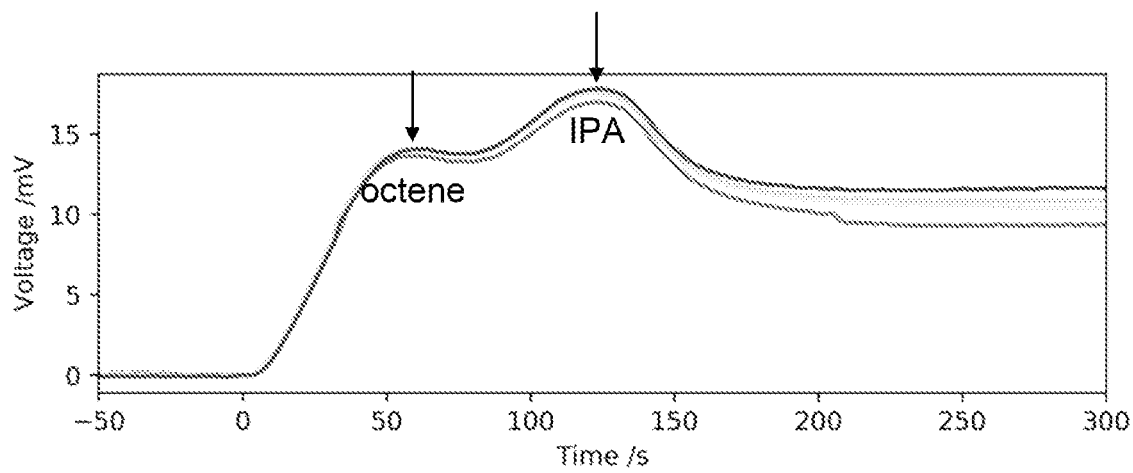
FIG. 28B shows a corresponding graph of first response as a function of time for a gaseous mixture of octene and IPA.

FIG. 28A shows a graph of temperature as a function of time; and FIG. 28B shows a corresponding graph of first response as a function of time for a gaseous mixture of octene and IPA. Here the temperature rate of 0.5 C/sec raising temperature from 5 to 70 C over 130 seconds. Particularly, FIG. 28B shows the PID response as a function of time after the detector has been exposed to a gaseous mixture of IPA and octene. The two peaks at lower and higher time correspond to octene and IPA, respectively. Three replicates are shown, demonstrating the reproducibility of the detector.

Experimental Summary

This technique has the ability to increase the response of a broadband VOC sensor by a factor up to 70 for the tested VOCs. While this does not translate to a 70 times improvement in the detection limit, since the gain appears to drop off at lower concentrations, even at very low concentrations, a gain of 20 times was observed. It is likely that the low concentration performance could be improved by a more detailed algorithm. Using the peak area rather than the peak height yields a factor 10 increase in the response, and use of a linear rather than a constant baseline in the peak area baseline improves the low concentration performance noticeably. This technique also removes the requirement for long-term stability of the sensor as the zero-VOC voltage is not required. Different VOCs have also been shown to have different temperature profiles for desorption. This enables classification (i.e. identification) of the analytes based on their respective profiles. It also highlights an issue (also seen during the concentration testing of limonene) that the choice of temperatures is not entirely arbitrary. To get the best performance out of the system the temperatures should be chosen to achieve as full desorption as possible.

Alternatives

Figure 24:
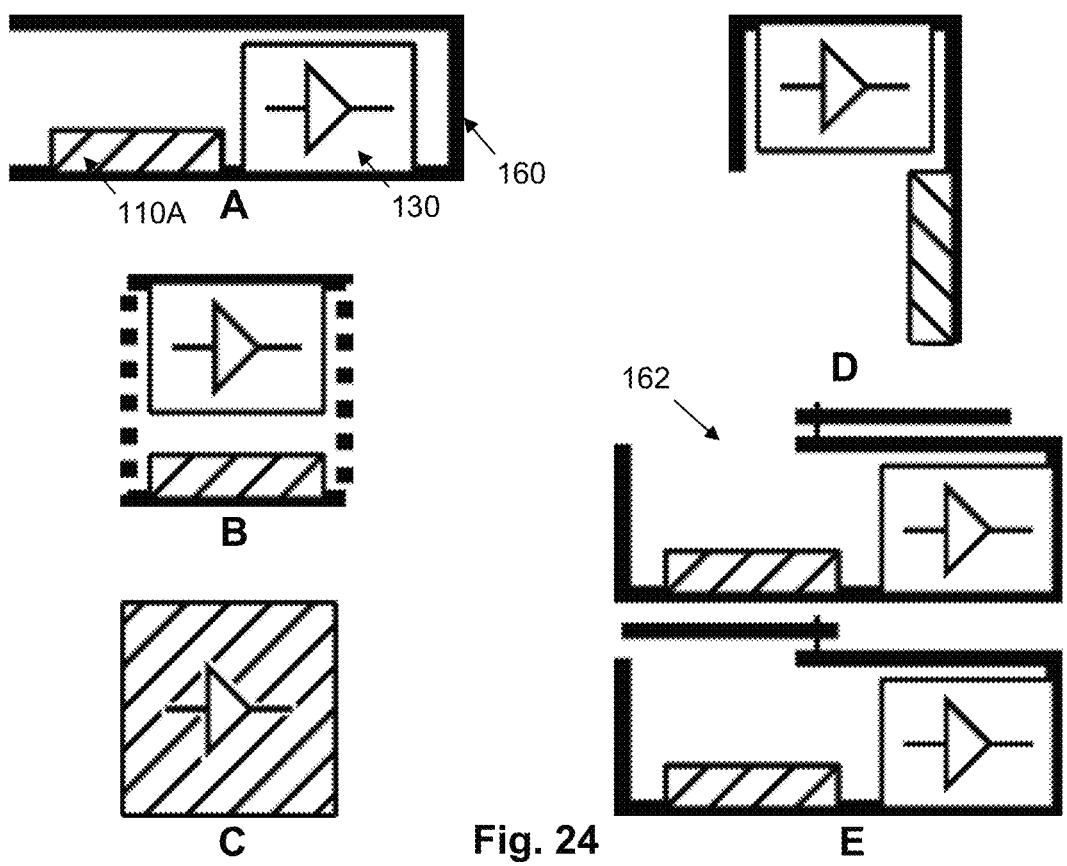
FIG. 24 schematically depicts alternative arrangements of the detector, according to exemplary embodiments.

FIG. 24 schematically depicts alternative arrangements of the detector, according to exemplary embodiments. The same schematic representations are used to represent the same features. FIG. 24A shows a first sorbent 110A and a sensor 130 arranged in a housing having one inlet (i.e. open end) only, thereby restricting flow of the first gas therein such that diffusional transport of the first analyte in the first gas dominates movement thereof, rather than flow of the first gas. FIG. 24B shows a first sorbent 110A and a sensor 130 having an open housing. FIG. 24C shows a first sorbent 110A and a sensor 130 closely bound (i.e. coupled) or fabricated on the same substrate. FIG. 24D shows a first sorbent 110A and a sensor 130 arranged in a semi-open housing oriented, in use, to promote convectional flow of the first gas. Note that if orientated correctly, when actively cooled air flow will draw sample from the environment to the first sorbent 110A, while when actively heated, the air flow will carry concentrated sample from the first sorbent 110A to the sensor 130. FIG. 24E shows a first sorbent 110A and a sensor 130 arranged in a housing 160 having a closeable inlet 162. This is a relatively simple arrangement which extends the high concentration measurement duration, since the inlet may be closed during measurement (i.e. sensing).

Figure 25:
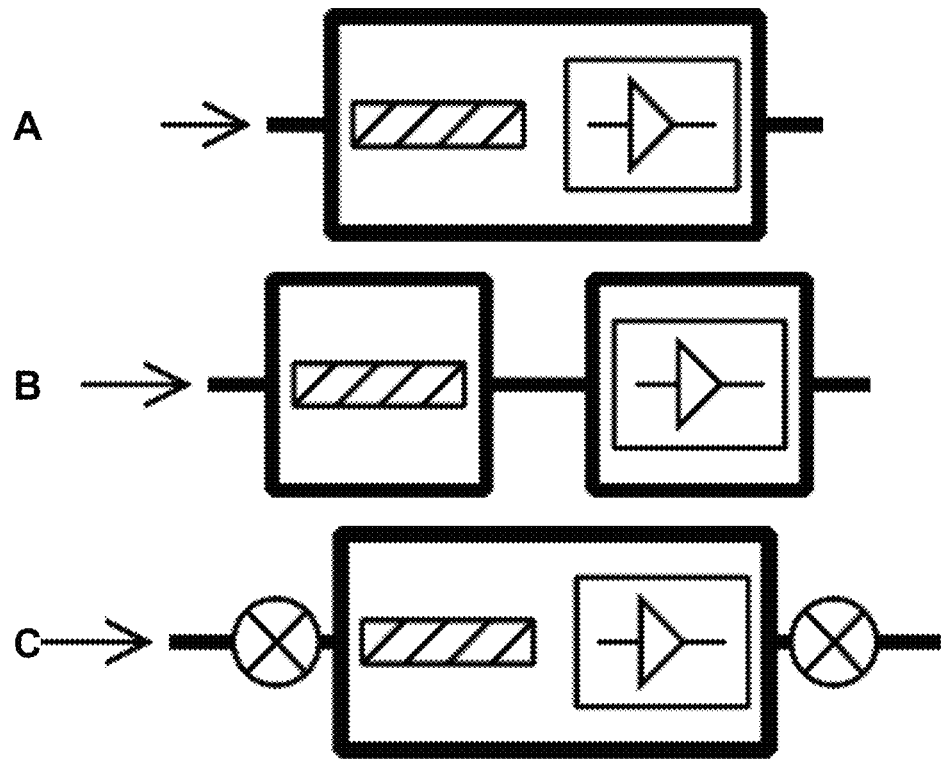
FIG. 25 schematically depicts alternative arrangements of the detector, according to exemplary embodiments.

FIG. 25 schematically depicts alternative arrangements of the detector, according to exemplary embodiments. The same schematic representations are used to represent the same features, as described with respect to FIG. 24.

FIG. 25A shows a first sorbent 110A and a sensor 130 arranged in a housing 160 having an inlet and an outlet, in fluid communication via a single chamber. The first sorbent 110A and the sensor 130 are in fluid communication with the chamber. Active flow of the first gas is through the chamber. Measurement can benefit from a non-constant flow rate if flow is controlled. FIG. 25B shows a first sorbent 110A and a sensor 130 arranged in a housing 160 having an inlet and an outlet, in fluid communication serially via a first chamber and a second chamber. The first sorbent 110A and the sensor 130 are arranged in the first chamber and in the second chamber, respectively. FIG. 25C shows a first sorbent 110A and a sensor 130 arranged in a housing 160 having an inlet and an outlet, in fluid communication via a single chamber. The first sorbent 110A and the sensor 130 are in fluid communication with the chamber. An inlet valve and an outlet valve are provided for the inlet and the outlet, respectively. In this way, repeat analysis may be performed and/or under different conditions.

Although a preferred embodiment has been shown and described, it will be appreciated by those skilled in the art that various changes and modifications might be made without departing from the scope of the invention, as defined in the appended claims and as described above.

In summary, the invention provides a detector for, and a method of, detecting analytes in gases. The detector comprises a sorbent for sorbing therein and/or thereon and/or desorbing therefrom, an analyte included in a gas exposed thereto, at a zeroth temperature, pressure ($T_0$, $P_0$), a controller arranged to change the zeroth temperature, pressure ($T_0$, $P_0$) to a first temperature, pressure ($T_1$, $P_1$) according to a first equation, to desorb and/or sorb at least some of the analyte; and a sensor arranged to sense at least some of the analyte and to output a response corresponding to the sensed analyte. The response comprises and/or is a characteristic response of the analyte.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims and drawings), and/or all of the steps of any method or process so disclosed, may be combined in any combination, except combinations where at most some of such features and/or steps are mutually exclusive.

Each feature disclosed in this specification (including any accompanying claims, and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims and drawings), or to any novel one, or any novel combination, of the steps of any method or process so disclosed.

The invention claimed is:

1. A detector for detecting analytes in gas-phase, comprising:
a first sorbent of a set of sorbents, wherein the first sorbent comprises and/or is a microporous and/or mesoporous dielectric or semiconducting material such as silica or silicon, a zeolite, activated carbon and/or a metal organic framework, MOF, for sorbing therein and/or thereon and/or desorbing therefrom, a first analyte of a set of analytes included in a first gas of a set of gases exposed thereto, at a zeroth temperature, pressure ($T_0$, $P_0$) of a set of temperatures, pressures (T, P), wherein the first gas is ambient air;
a cooler configured to cool the first sorbent to the zeroth temperature ($T_0$);
a controller configured to change the zeroth temperature, pressure ($T_0$, $P_0$) to a first temperature, pressure ($T_1$, $P_1$) of the set of temperatures, pressures (T, P) according to a first equation of a set of equations, to desorb and/or sorb at least some of the first analyte; and
a sensor configured to sense at least some of the first analyte and to output a first response of a set of responses corresponding to the sensed first analyte,
wherein:
the sensor comprises and/or is an optical detector, for example an IR or a UV detector and/or an ion spectrometer; and
the first response comprises and/or is a first characteristic response of a set of characteristic responses of the first analyte.

2. The detector according to claim 1, wherein the controller is configured to compare the first response with a set of reference responses.

3. The detector according to claim 2, wherein the controller is configured to match the first response with a first reference response of the set of reference responses.

4. The detector according to claim 1, wherein the controller is configured to change only the zeroth temperature ($T_0$) to the first temperature ($T_1$).

5. The detector according to claim 1, comprising a heater and/or cooler configured to heat and/or cool the first sorbent and/or the sorbed first analyte to the first temperature, pressure ($T_1$, $P_1$).

6. The detector according to claim 5, wherein the heater is thermally coupled to the first sorbent.

7. The detector according to claim 1, wherein the controller is configured to change the zeroth temperature, pressure ($T_0$, $P_0$) to the first temperature, pressure ($T_1$, $P_1$) according to a first survey equation of a set of survey equations, before changing the zeroth temperature, pressure ($T_0$, $P_0$) to the first temperature, pressure ($T_1$, $P_1$) according to the first equation.

8. The detector according to claim 1, comprising a pump configured to flow the first gas across and/or through the first sorbent.

9. The detector according to claim 1, wherein:
the first sorbent is for sorbing therein and/or thereon, a second analyte of the set of analytes included in the first gas of a set of gases exposed thereto, at the zeroth temperature, pressure ($T_0$, $P_0$);
the controller is configured to change the first temperature, pressure ($T_1$, $P_1$) to a second temperature, pressure ($T_2$, $P_2$) of the set of temperatures, pressures (T, P) according to a second equation of the set of equations, to desorb at least some of the sorbed second analyte from the first sorbent;
the detector is configured to detect at least some of the desorbed second analyte and to output a second response of the set of responses corresponding to the sensed second analyte; and
the second response comprises and/or is a first characteristic response of a set of characteristic responses of the second analyte.

10. The detector according to claim 1, wherein the detector is configured to obtain a first baseline response of a set of baseline responses at the zeroth temperature, pressure ($T_0$, $P_0$) and wherein the controller is configured to modify the first response based, at least in part, on the obtained first baseline response.

11. A method of detecting analytes in gas-phase, comprising:
exposing a first sorbent of a set of sorbents, wherein the first sorbent comprises and/or is a microporous and/or mesoporous dielectric or semiconducting material such as silica, a zeolite, activated carbon and/or a metal organic framework, MOF, to a first gas of a set of gases, at a zeroth temperature, pressure ($T_0$, $P_0$) of a set of temperatures, pressures (T, P), wherein the first gas is ambient air;
cooling the first sorbent to the zeroth temperature ($T_0$) and sorbing by the first sorbent, therein and/or thereon, a first analyte of a set of analytes included in the first gas;
desorbing and/or sorbing at least some of the first analyte by controlling a change from the zeroth temperature, pressure ($T_0$, $P_0$) to a first temperature, pressure ($T_1$, $P_1$) of the set of temperatures, pressures (T, P) according to a first equation of a set of equations; and
sensing, by a sensor, at least some of the first analyte and outputting a first response of a set of responses corresponding to the sensed first analyte,
wherein:
the sensor comprises and/or is an optical detector, for example an IR or a UV detector and/or an ion spectrometer; and
the first response comprises and/or is a first characteristic response of a set of characteristic responses of the first analyte.

12. The method according to claim 11, comprising comparing the first response with a set of reference responses.

13. The method according to claim 12, comprising matching the first response with a first reference response of the set of reference responses.

14. The method according to claim 11, comprising controlling only the change from the zeroth temperature ($T_0$) to the first temperature, pressure ($T_1$).

15. The method according to claim 11, comprising controlling only the change from the zeroth pressure ($P_0$) to the first pressure ($P_1$).

16. The method according to claim 11, comprising changing the zeroth temperature, pressure ($T_0$, $P_0$) to the first temperature, pressure ($T_1$, $P_1$) according to a first survey equation of a set of survey equations, before changing the zeroth temperature, pressure ($T_0$, $P_0$) to the first temperature, pressure ($T_1$, $P_1$) according to the first equation.

17. The method according to claim 11, comprising:
- sorbing, preferably adsorbing, by the first sorbent, therein and/or thereon, a second analyte of the set of analytes included in the first gas of a set of gases exposed thereto, at the zeroth temperature, pressure $(T_0, P_0)$;
- desorbing at least some of the sorbed, preferably adsorbed, second analyte from the first sorbent by changing the first temperature, pressure $(T_1, P_1)$ to a second temperature, pressure $(T_2, P_2)$ of the set of temperatures, pressures $(T, P)$ according to a second equation of the set of equations; and
- sensing at least some of the desorbed second analyte and outputting a second response of the set of responses corresponding to the sensed second analyte;
- wherein the second response comprises and/or is a first characteristic response of a set of characteristic responses of the second analyte.

18. The method according to claim 11, comprising obtaining a first baseline response of a set of baseline responses at the zeroth temperature, pressure $(T_0, P_0)$ and modifying the first response based, at least in part, on the obtained first baseline response.

19. The method according to claim 11, wherein the first analyte is selected from VOCs, explosive compounds, biohazards, chemical weapons, semi-volatile compounds, emission compounds and/or greenhouse gases.

20. The method according to claim 11, wherein the set of analytes comprises N analytes selected from VOCs, explosive compounds, biohazards, chemical weapons, semi-volatile compounds, emission compounds and/or greenhouse gases.

* * * * *

UNITED STATES PATENT AND TRADEMARK OFFICE
CERTIFICATE OF CORRECTION

| | | |
|---|---|---|
| PATENT NO. | : 12,270,784 B2 | Page 1 of 1 |
| APPLICATION NO. | : 18/538368 | |
| DATED | : April 8, 2025 | |
| INVENTOR(S) | : Tanya Hutter et al. | |

It is certified that error appears in the above-identified patent and that said Letters Patent is hereby corrected as shown below:

On the Title Page

Item [57], Line 2, delete "in described." and insert -- is described. --, therefor.

Signed and Sealed this
Eighth Day of July, 2025

Coke Morgan Stewart
*Acting Director of the United States Patent and Trademark Office*